US011814433B2

(12) United States Patent
Basilico et al.

(10) Patent No.: US 11,814,433 B2
(45) Date of Patent: Nov. 14, 2023

(54) COMBINATION OF ANTI-HGFR ANTIBODY AND HEGFR FOR THE TREATMENT OF A TUMOR AND/OR METASTASIS

(71) Applicant: Vertical Bio AG, Basel (CH)

(72) Inventors: Cristina Basilico, Pavarolo (IT); Elisa Vigna, Villarbasse (IT); Paolo Maria Comoglio, Arignano (IT)

(73) Assignee: Vertical Bio AG, Basel (CH)

( * ) Notice: Subject to any disclaimer, the term of this patent is extended or adjusted under 35 U.S.C. 154(b) by 244 days.

(21) Appl. No.: 16/982,330

(22) PCT Filed: Mar. 21, 2019

(86) PCT No.: PCT/IB2019/052307
§ 371 (c)(1),
(2) Date: Sep. 18, 2020

(87) PCT Pub. No.: WO2019/180658
PCT Pub. Date: Sep. 26, 2019

(65) Prior Publication Data

US 2021/0070868 A1 Mar. 11, 2021

(30) Foreign Application Priority Data

Mar. 22, 2018 (IT) ........................ 102018000003875

(51) Int. Cl.

| | |
|---|---|
| *C07K 16/28* | (2006.01) |
| *C07K 14/71* | (2006.01) |
| *A61P 3/00* | (2006.01) |
| *A61P 35/00* | (2006.01) |
| *A61K 38/17* | (2006.01) |
| *A61K 39/395* | (2006.01) |
| *A61K 39/00* | (2006.01) |
| *A61P 31/00* | (2006.01) |

(52) U.S. Cl.
CPC ........ *C07K 16/2863* (2013.01); *A61K 38/179* (2013.01); *A61K 39/39558* (2013.01); *A61P 31/00* (2018.01); *A61P 35/00* (2018.01); *C07K 14/71* (2013.01); *A61K 2039/505* (2013.01); *C07K 2317/52* (2013.01); *C07K 2317/522* (2013.01); *C07K 2317/55* (2013.01); *C07K 2317/565* (2013.01); *C07K 2317/622* (2013.01); *C07K 2317/73* (2013.01); *C07K 2317/76* (2013.01); *C07K 2319/00* (2013.01)

(58) Field of Classification Search
None
See application file for complete search history.

(56) References Cited

FOREIGN PATENT DOCUMENTS

| | | | |
|---|---|---|---|
| RU | 2384331 | 12/2009 | |
| WO | 2007/090807 | 8/2007 | |
| WO | WO-2007090807 A1 * | 8/2007 | ......... C07K 16/2863 |
| WO | 2014/108829 | 7/2014 | |

OTHER PUBLICATIONS

Michieli et al (Targeting the tumor and its microenvironment by a dual-function decoy Met receptor, Cancer Cell, vol. 6, Jul. 2004, pp. 61-73). (Year: 2004).*

Modica, C, et al., "Vertical Inhibition of Met by Dual Decoy/ Antibody Strategy," 2nd EACR-OECI Conference, Abstr. 36, Mar. 13, 2017.

Michieli, P. et al., "Targeting the Tumor and its Microenvironment by a Dual-Function Decoy Met Receptor," Cancer Cell, vol. 6, No. 1, Jul. 1, 2004.
International Search Report and Written Opinion of the ISA for PCT/IB2019/52307, dated Jun. 21, 2019, 13 pages.
Petrelli et al., "Ab-induced ectodomain shedding mediates hepatocytes growth factor receptor down-regulation and hampers biological activity", Proceedings of the National Academy of Sciences (PNAS), vol. 103, No. 13, Mar. 28, 2013, pp. 5090-5095.
Tiran et al., "A Novel Recombinant Soluble Splice Variant of Met Is a Potent Antagonist of the Hepatocyte Growth Factor/Scatter Factor-Met Pathway", Clinical Cancer Research, Clinical Cancer Research, vol. 14, No. 14, Jul. 15, 2008, pp. 4612-4621.
Pacchiana et al., "Monovalency Unleashes the Full Therapeutic Potential of the DN-30 Anti-Met Antibody", Journal of Biological Chemistry, vol. 285, No. 46, Nov. 12, 2010, pp. 36149-36157.

(Continued)

*Primary Examiner* — Laura B Goddard
*Assistant Examiner* — Sarah A Alsomairy
(74) *Attorney, Agent, or Firm* — NIXON & VANDERHYE, PC

(57) ABSTRACT

An anti-HGFR antibody fragment in combination with an extracellular portion of human HGFR for use in the treatment of a patient suffering from a tumor and/or metastasis, wherein: (i) the anti-HGFR antibody fragment has only one paratope able to bind to an epitope of the extracellular portion of human HGFR and has antagonist activity towards HGFR, (ii) the extracellular portion of human HGFR is capable of binding to HGF in a stable manner and contains at least one amino acid mutation at the epitope recognized by the anti-HGFR antibody fragment to prevent binding of the anti-HGFR antibody fragment thereto, and (iii) the anti-HGFR antibody fragment and the extracellular portion of human HGFR are suitable for administration to the patient are suitable for administration to the patient (a) in a protein form or (b) in a nucleic acid form.

27 Claims, 12 Drawing Sheets

Specification includes a Sequence Listing.

(56) References Cited

OTHER PUBLICATIONS

Basilico et al., "Targeting the MET oncogene by concomitant inhibition of receptor and ligand via an antibody-"decoy" strategy : Vertical inhibition of the HGF/MET axis", International Journal of Cancer, vol. 143, No. 7, Apr. 25, 2018, pp. 1774-1785.
Xiaoying Chen et al. "Fusion Protein Linkers: Property, Design and Functionality", Adv Drug Deliv Rev. Oct. 15, 2013; 65(10), 32 pages.
Michele Orlando, "Modification of proteins and low molecular weight substances with hydroxyethyl starch (HES)", Dissertation, Justus-Liebig-Universität Gießen, 2003, 191 pages.
Yumi Maeda et al., "Engineering of Functional Chimeric Protein G-*Vargula* Luciferase", Analytical Biochemistry 249, Article No. AB972181, 1997, pp. 147-152.
Cristina Basilico et al., "Targeting the MET oncogene by concomitant inhibition of receptor and ligand via an antibody-"decoy" strategy", International Journal of Cancer, 143, 2018, pp. 1774-1785.

\* cited by examiner

A

B

A

| | VEHICLE | MvDN30 | K842E | COMBO |
|---|---|---|---|---|
| Tot. Flux (P/s x $10^8$) | 4.17 ± 0.78 | 4.06 ± 1.44 | 3.95 ± 1.18 | 2.70 ± 0.68 |

B

C

A

B

C

| | K842E_scMvDN30 | | | scMvDN30_K842E | | | Combo |
|---|---|---|---|---|---|---|---|
| | L60 | L45 | L134 | L60 | L45 | L134 | |
| IC50 (nM) | 4330,67 | 6535,68 | 4969,85 | 8919,07 | 4990,27 | 3530,98 | 662,20 |

COMBINATION OF ANTI-HGFR ANTIBODY AND HEGFR FOR THE TREATMENT OF A TUMOR AND/OR METASTASIS

This application is the U.S. national phase of International Application No. PCT/IB2019/052307 filed 21 Mar. 2019, which designated the U.S. and claims priority to IT Patent Application No. 102018000003875 filed 22 Mar. 2018, the entire contents of each of which are hereby incorporated by reference.

FIELD OF THE INVENTION

The disclosure concerns a novel combination of therapeutic agents for the treatment of a tumor and/or metastasis, preferably metastasis.

BACKGROUND OF THE INVENTION

Metastatic spreading is based on the ability of cancer cells to disrupt cell-to-cell interactions, migrate through the extracellular matrix, survive and proliferate in tissues other than their site of origin. The physiological counterpart of this complex program—known as 'invasive growth'—is at the basis of embryogenesis and accounts for wound healing and organ regeneration during adult life. Invasive growth is tightly regulated by specific extracellular signals, one of which is Hepatocyte Growth Factor (HGF), the ligand for the receptor encoded by MET oncogene. In conditions of aberrant activation, HGF/MET signaling drives tumor onset, progression and metastasis in a broad spectrum of human malignancies. In a minority of events, MET behaves as a 'driver' oncogene and tumor cells are dependent on constitutive MET signaling for growth and survival ('MET addiction'). This condition relies on the presence of genetic lesions, mostly increased gene copy number or—less frequently—mutations[2] that result in constitutive ligand-independent receptor activation. In this context, treatment with MET inhibitors is highly effective, inducing block of cell proliferation and cell cycle arrest in vitro and inhibition of tumor growth in vivo. The co-expression of ligand and receptor within the same cell is another strategy exploited by cancer to achieve continuous MET activation, and has been described mainly in non-epithelial human cancers, such as osteosarcomas, glioblastomas and multiple myelomas. In most cases, however, aberrant MET activation in tumors originates from receptor over-expression, due to transcriptional upregulation of the wild-type gene, triggering cancer cell sensitization to ligand stimulation[3]. In the latter case, MET signaling—which results in pro-invasive and anti-apoptotic responses—is exploited by cancer cells as a strategy to bypass stress conditions and boosts the malignant phenotype ('MET expedience'[6]). In the absence of specific genetic lesions, MET is not strictly necessary for tumor growth, but the presence of the ligand sustains receptor activation, enhancing the malignant phenotype. Finally, MET behaves as a functional marker of cancer 'stem-progenitor' cells in glioblastomas[8], and supports the 'stem' phenotype in colorectal and breast cancers[12,15]. Moreover, it has been shown that stromal-derived HGF sustains the WNT self-renewal pathway of colorectal cancer stem cells and promotes proliferation of colon cancer initiating cells, triggering resistance to anti-EGFR therapy[27].

A number of strategies targeting MET or HGF—either small molecule inhibitors, antibodies or recombinant proteins—have been designed and are currently under investigation. Among them, the MvDN30 antibody is a monovalent chimeric Fab fragment that binds to the extracellular domain of MET, inducing proteolytic cleavage ('shedding') of the receptor from the cell surface[21, 28]. DecoyMET is a recombinant soluble receptor encompassing the whole extracellular region of MET; it binds HGF with high affinity and inhibits ligand-driven biological activities in vitro and in vivo when expressed by lentiviral vector technology[17] or as Fc-fusion protein[7,26]. As in the majority of biological systems, hitting a single element of a signal transduction chain unlikely results in complete shut-off of the response. Thus, in the case of MET, every molecule will never achieve 100% inhibition, leaving residual activity sensitive to HGF stimulation.

SUMMARY OF THE INVENTION

The object of this disclosure is to provide novel combination of anti-tumor agents useful in the treatment of oncologic patients.

According to the invention, the above object is achieved thanks to the subject matter recalled specifically in the ensuing claims, which are understood as forming an integral part of this disclosure.

The present invention provides an anti-Hepatocyte Growth Factor Receptor (HGFR) antibody fragment in combination with an extracellular portion of human HGFR for use in the treatment of a patient suffering from a tumor and/or metastasis, preferably metastasis, wherein:

(i) the anti-HGFR antibody fragment has only one paratope able to bind to an epitope of the extracellular portion of human HGFR and has antagonist activity towards HGFR, (ii) the extracellular portion of human HGFR is capable of binding to Hepatocyte Growth Factor (HGF) in a stable manner and contains at least one amino acid mutation within the epitope recognized by the anti-HGFR antibody fragment to prevent binding of the anti-HGFR antibody fragment thereto, and (iii) the anti-HGFR antibody fragment and the extracellular portion of human HGFR are suitable for administration to the patient (a) in a protein form or (b) in a nucleic acid form.

BRIEF DESCRIPTION OF THE DRAWINGS

The invention will now be described in detail, purely by way of illustrative and non-limiting example, with reference to the attached figures, wherein.

(A) Comparison of the aminoacid sequences of the third and fourth IPT domains of human, mouse, rat and dog MET. Residues that are changed exclusively in the mouse sequence are highlighted in in bold, white on black background, aminoacids that are changed also (or only) in the rat or dog sequences are highlighted in bold. Only the IPT-3/IPT-4 boundaries are shown. (B) DecoyMET receptors carrying single aminoacid substitutions were incubated with the DN30 antibody. The complexes were immunoprecipitated with protein A—that binds to the antibody- and revealed with HRP-conjugated streptactin—that binds to the strep-tag in the decoy (left panel). 30 µl of normalized supernatants used for the immunoprecipitation were run on SDS PAGE to verify decoyMET receptors loading (right panel). (C) ELISA binding analysis. DN30 mAb was in liquid phase, wild-type decoyMET or decoyMET$^{K842E}$ in solid phase. Antibody binding was detected using an HRP-conjugated anti-mouse antibody. OD, optical density at 450 nm. Each point is the mean of values in triplicate±SD.

Figure 2:
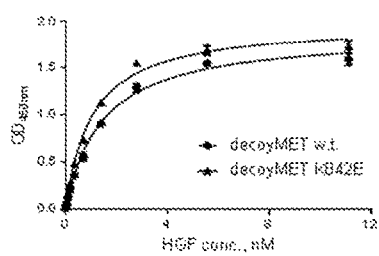
Figure 2:
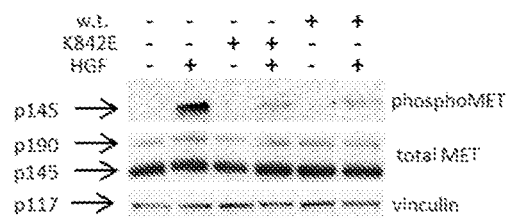

FIG. 2. DecoyMET$^{K842E}$ binds HGF at high affinity and inhibits HGF-induced MET phosphorylation.

(A) ELISA binding analysis. Wild-type decoyMET or decoyMET$^{K842E}$ were in solid phase; increasing concentrations of HGF were added in liquid phase. HGF binding was detected using a biotinylated anti-HGF antibody. Each point is the mean of values in triplicate±SD. (B) HGF-induced MET phosphorylation. A549 cells were incubated with wild-type decoyMET or decoyMET$^{K842E}$ (2 μM) and stimulated with HGF (50 ng/ml). Total cell lysates were immunoblotted with anti-phosphoMET (upper panel), anti-MET antibodies (middle panel) or with anti-vinculin antibodies (lower panel). p145, mature form of MET; p190, single-chain precursor of MET; p117, vinculin.

Figure 3:
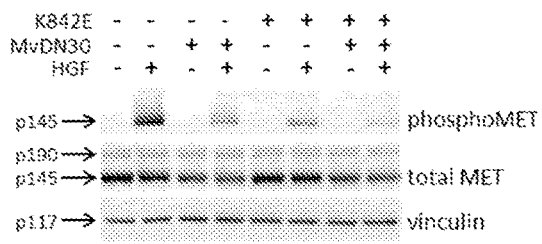
Figure 3:
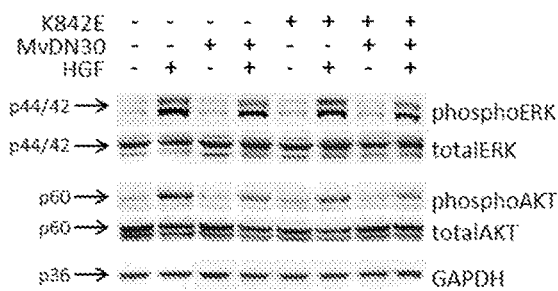
Figure 3:
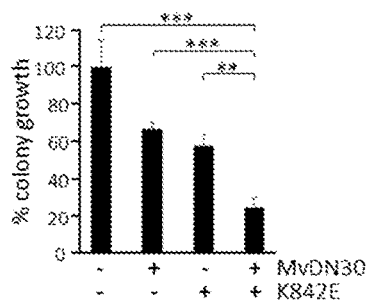
Figure 3:
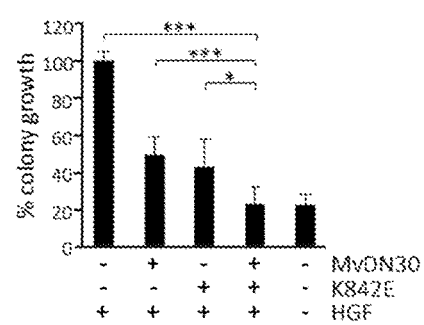
Figure 3:
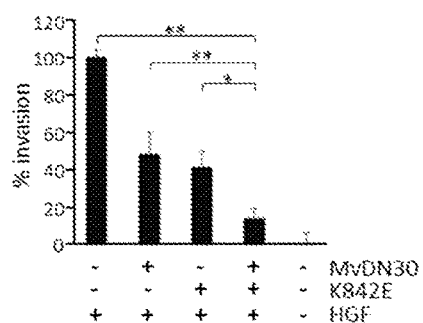
Figure 3:
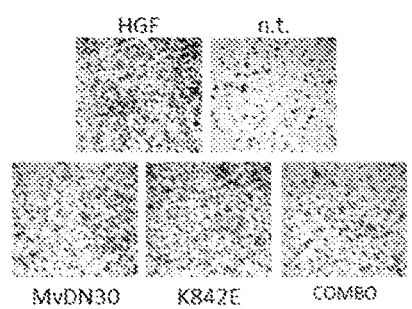

FIG. 3. MvDN30 and DecoyMET$^{K842E}$ cooperate in reducing HGF-induced MET phosphorylation and MET-driven biological activities.

(A) HGF-induced MET phosphorylation. A549 human lung adenocarcinoma cells were incubated with 2 μM decoyMET$^{K842E}$, 125 nM MvDN30 or the combination of the two, and stimulated or not with 50 ng/ml HGF. Total cell lysates were immunoblotted with anti-phosphoMET (upper panel), anti-MET antibodies (middle panel) or anti-vinculin (lower panel). p145, mature form of MET; p190, single-chain precursor of MET; p117, vinculin. (B) HGF-induced ERK and AKT phosphorylation. A549 human lung adenocarcinoma cells were incubated with 500 nM MvDN30, 2 μM decoyMET$^{K842E}$ or the combination of the two, and stimulated or not with 100 ng/ml HGF. Total cell lysates were immunoblotted with anti-phosphoERK, anti-ERK, anti-phosphoAKT, anti-AKT, anti-GAPDH. p42/44, ERK; p60, AKT; p36, GAPDH. (C) Anchorage-independent growth sustained by autocrine HGF stimulation. U87-MG human glioblastoma cells, expressing both HGF and MET proteins, were treated with 0.5 μM MvDN30 or 1 μM decoyMET$^{K842E}$, alone or in combination. Graph represents percentage of average colony growth for each treatment compared to the untreated control. (D) Anchorage-independent growth sustained by paracrine HGF stimulation. A549 cells were stimulated with 30 ng/ml HGF and treated with 1 μM MvDN30 or 1 μM decoyMET$^{K842E}$, alone or in combination. Graph represents percentage of average colony growth for each treatment compared to the HGF-stimulated control. (E) Transwell invasion assay. HPAF-II human pancreatic adenocarcinoma cells were stimulated with 12.5 ng/ml HGF and treated with 0.5 μM MvDN30 or 1 μM decoyMET$^{K842E}$, alone or in combination. Graph represents the percentage of invasion in comparison to the HGF-stimulated control. Right panel, one representative image/group of the cells migrated through the matrigel layer. n.t., not treated cells. Magnification, 200×. Each point is the mean of values in triplicate±SD. *=P 0.001; =P 0.01; *=P 0.05.

Figure 4:
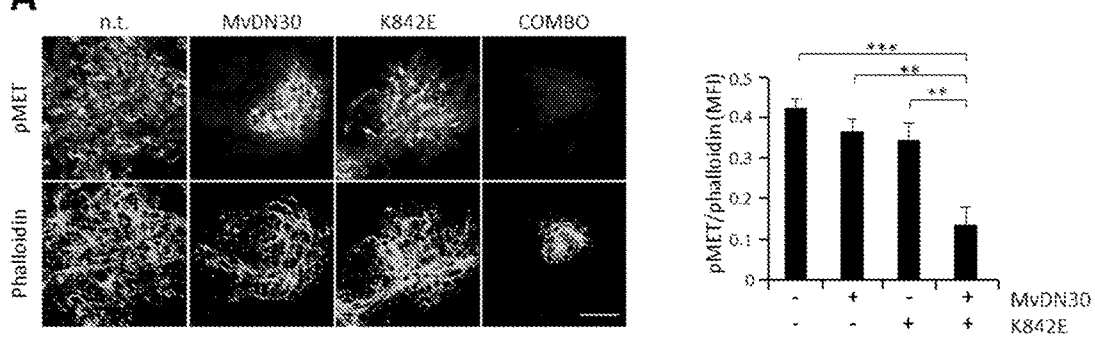
Figure 4:
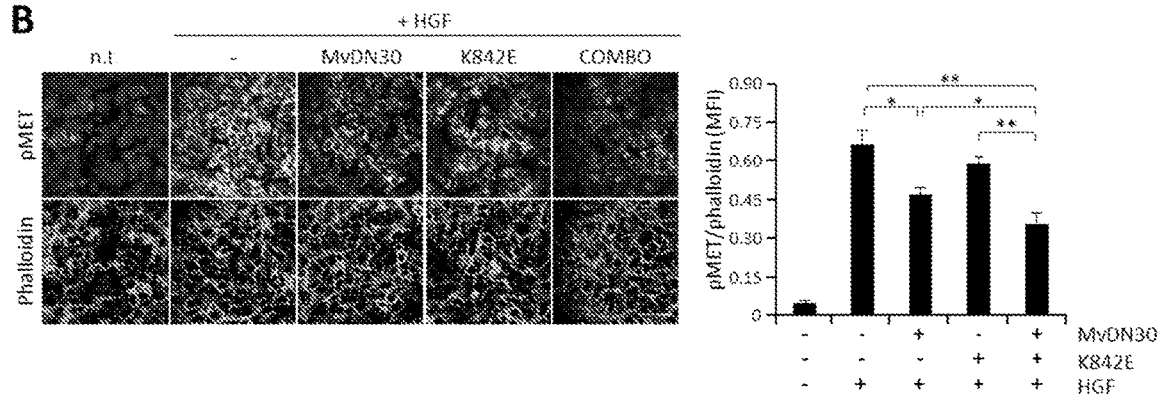
Figure 4:
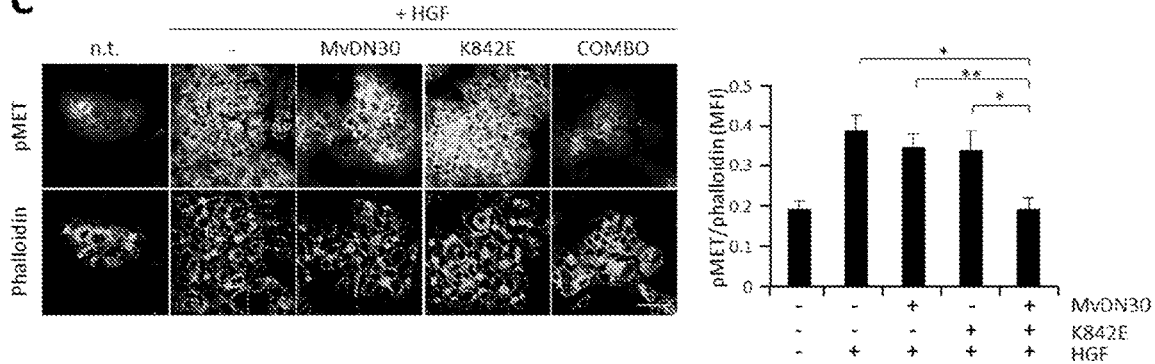

FIG. 4. MvDN30 and decoyMET$^{K842E}$ in combination inhibit HGF-dependent MET phosphorylation.

U87MG (A), A549 (B) and HPAF-II (C) cells were treated with MvDN30, decoyMET$^{K842E}$ or the combination of the two (COMBO). HPAF-II and A549 cells were stimulated or not with HGF; n.t., not treated cells. Left panels: representative confocal sections showing anti-phosphoMET (top rows) and phalloidin (bottom rows). Graphs on the right report the Mean Fluorescence Intensity (MFI) of phospho-MET, background subtracted and normalized on phalloidin. Each point is the mean of 5 values±SEM. Bar is 50 μm. *=P≤0.001; =P=0.01; *=P≤0.05.

Figure 5:
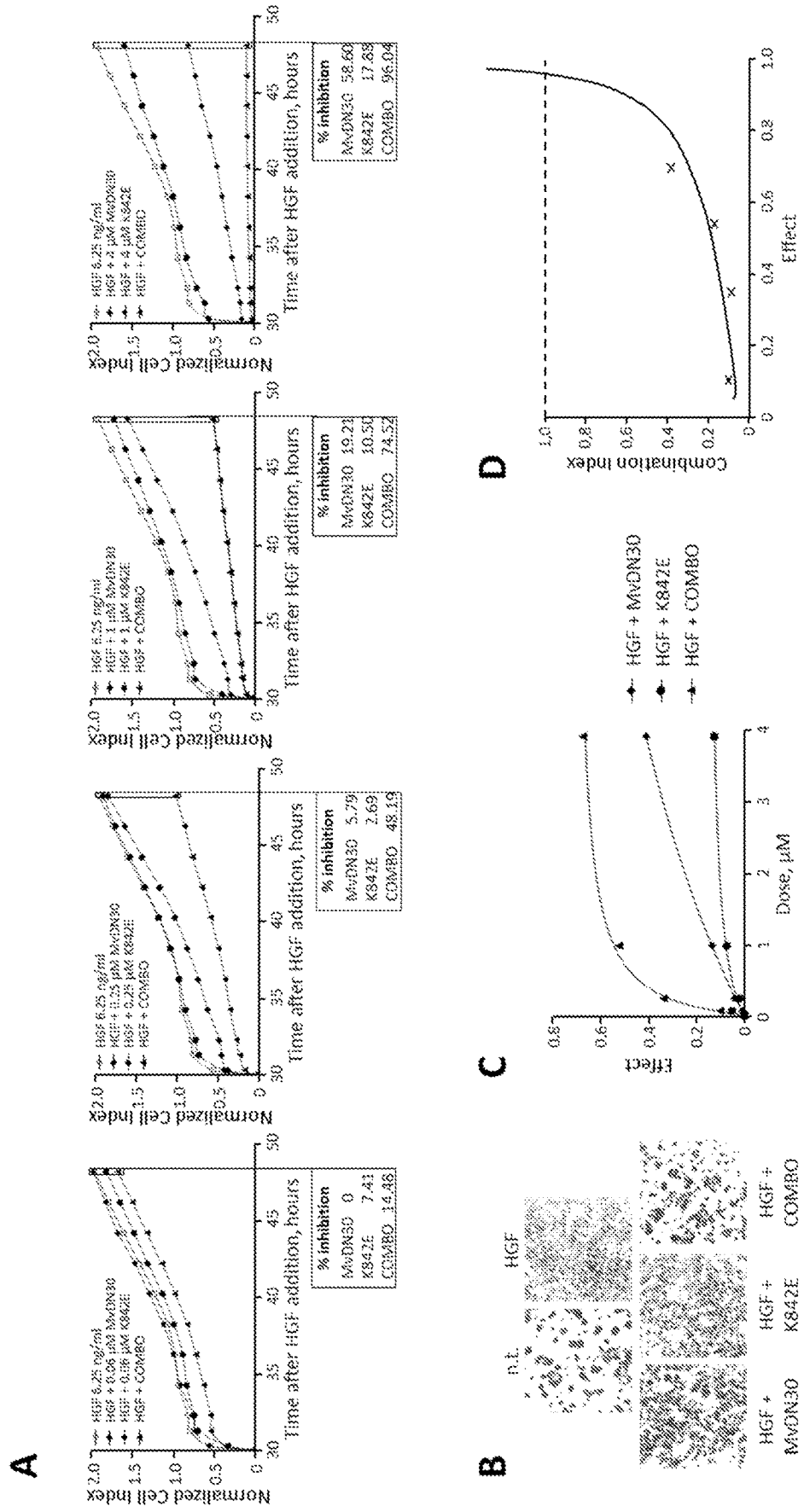

FIG. 5. MvDN30 and DecoyMET$^{K842E}$ synergize to inhibit HGF-dependent cell scattering.

(A) Analysis of cell motility. HPAF-II cells were pre-incubated with different concentrations (0.06, 0.25, 1 or 4 μM) of MvDN30 or decoyMET$^{K842E}$, alone or in 1:1 combination, and then stimulated with 6.25 ng/ml HGF. Cell scattering was monitored in real time using an X-CELLigence RICA device and is expressed as Normalized Cell Index. Each graph refers to one treatment concentration. (B) Representative images of HPAF-II cells pre-incubated with 1 μM MvDN30 or 1 μM decoyMET$^{K842E}$, alone or in combination, and then stimulated with 6.25 ng/ml HGF. n.t., not treated cells. (C) Cell motility curve. Effect=Cell index values measured at the end of the experiment for each dose of treatment, normalized on the values obtained with HGF alone and expressed as [1-x]. (D) Drug combination analysis. Values from the cell motility curve were elaborated with the Calcusyn software to calculate the Combination Index (CI) for each concentration of MvDN30 and decoyMET$^{K842E}$. CI=1, cooperation; CI<1, synergism; CI>1, antagonism.

Figure 6:
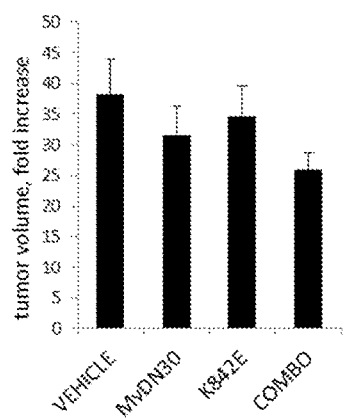
Figure 6:
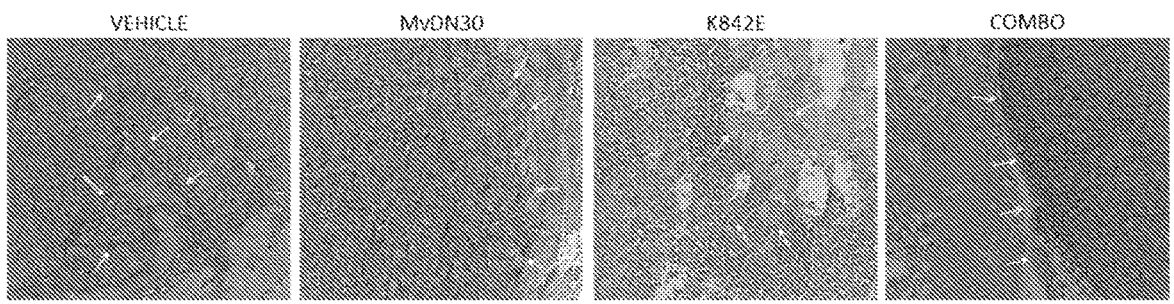

FIG. 6. MvDN30 and decoyMET$^{K842E}$ in combination reduce the invasive phenotype of subcutaneous U87-MG tumors.

U87-MG cells were injected subcutaneously in NOD-SCID mice. When the tumors reached a volume of 80-100 mm$^3$, mice were stratified in four homogeneous groups: VEHICLE (n=10); MvDN30 (n=9); K842E (n=9); the combination of the two (n=10). (A) Tumor volume at sacrifice, expressed as fold increase. Each bar is the mean of the group±SEM. (B) Histochemical analysis of tumor burden. Representative images of hematoxylin-eosin stained tumor sections. Arrows point to the boundary between the tumor and the surrounding tissue. Magnification 100×.

Figure 7:
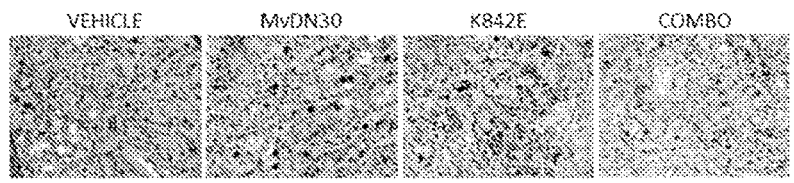
Figure 7:
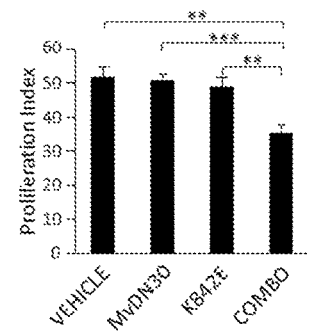
Figure 7:
Figure 7:
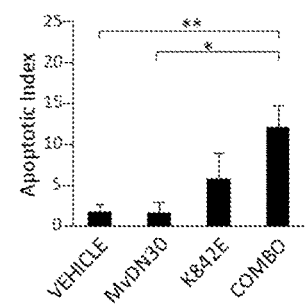

FIG. 7. Effect of MvDN30 or decoyMET$^{K842E}$, alone and in combination, on the proliferation and apoptosis of pancreatic cancer cells injected orthotopically in hHGF-Ki mice.

Luciferase-expressing HPAF-II cells were injected in the pancreas of hHGF-Ki mice and stratified into four homogeneous groups: VEHICLE (n=10), MvDN30 (n=6), decoyMET$^{K842E}$ (n=6), the combination of the two (n=6). (A) Tumor bioluminescence detected by IVIS Spectrum. Numbers indicate the average values of total flux of bioluminescence (photons/second×10$^8$) of each experimental group±SEM. (B) Analysis of tumor cell proliferation measured by Ki67 immunohistochemistry. Left panel, representative images of each experimental group. Magnification, 200×. Graph on the right reports average values obtained by the analysis of five images per tumor±SEM. Proliferation Index is calculated as Ki67 positive cells/total number of cells. (C) Analysis of tumor cell apoptosis measured by cleaved Caspase-3 immunofluorescence. Left panel, representative images of each experimental group. Bar is 50 μm. Graph on the right reports average values obtained by the analysis of 8 images per tumor±SEM. Apoptotic index is calculated as cleaved Caspase-3 positive cells/total number of cells. Bar is 50 μm. *=P value<0.001; =P value<0.01; *=P value<0.05.

Figure 8:
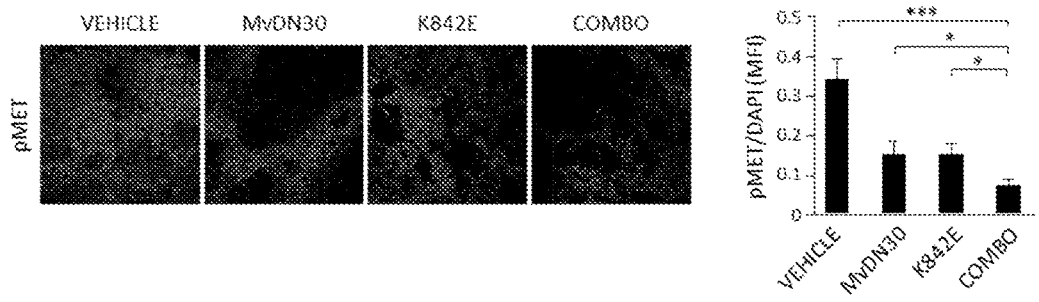
Figure 8:
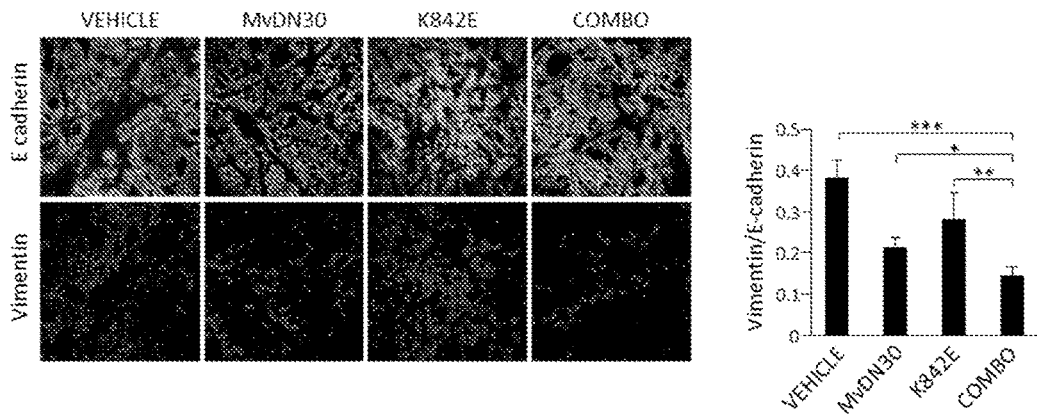
Figure 8:
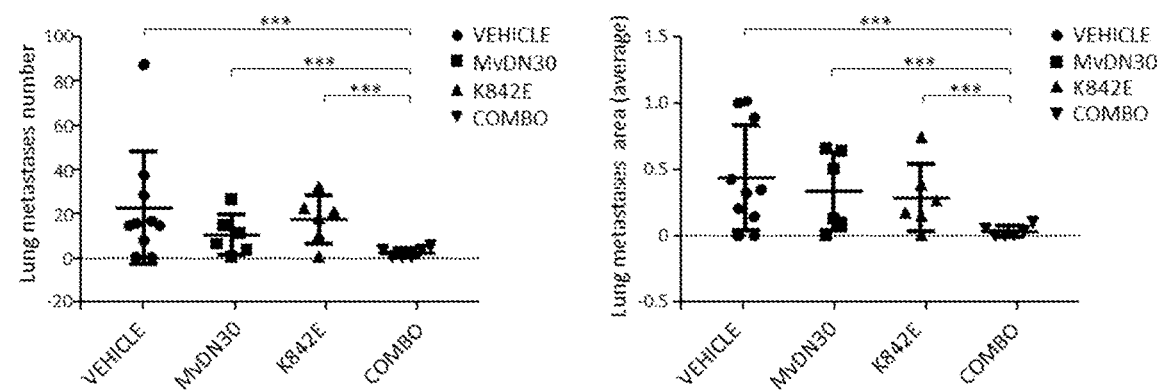

FIG. 8. MvDN30 and DecoyMET$^{K842E}$ reduce MET phosphorylation and metastatic dissemination of pancreatic cancer cells in hHGF-Ki mice.

Luciferase-expressing HPAF-II cells were injected in the pancreas of hHGF-Ki mice and stratified into four homogeneous groups: VEHICLE (n=10), MvDN30 (n=6), decoyMET$^{K842E}$ (n=6), the combination of the two (n=6). (A) PhosphoMET status within tumors measured by immunofluorescence. Left panel, representative confocal sections of each experimental group showing anti-phosphoMET. Graph on the right reports the Mean Fluorescence Intensity (MFI) of phosphoMET, background subtracted and normalized on DAPI. Each point is the mean of 12 values±SEM. Bar is 50 μm. (B) Evaluation of the EMT phenotype of HPAF-II tumors by immunofluorescence analysis of E-cadherin and vimentin expression. Left panel, representative images of each experimental group. Anti-E-cadherin (top row), anti-vimentin (lower row). Bar is 50 μm. Graph on the right reports average values obtained by the analysis of 6 images per each tumor±SEM. EMT phenotype is expressed as Vimentin/E-cadherin ratio. (C) Metastatic nodules in the lungs evaluated by histochemical HE staining. Graph on the left: number of metastatic lesions; each point represents the number of lesions scored for each mouse.

Graph on the right: area of metastatic lesions; each point represents the average area of metastases measured for each mouse. Ten slides/mouse were analyzed; metastatic lesions were scored and their area quantified with ImageJ. *=P≤0.001; =P≤0.01; *=P≤0.05.

Figure 9:
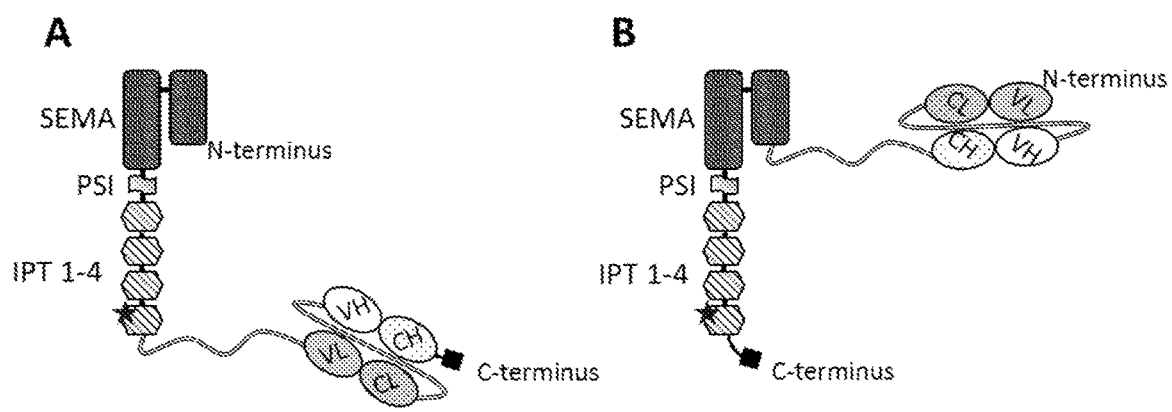

FIG. 9. Schematic representation of one embodiment of the fusion proteins containing an anti-HGFR antibody fragment and an extracellular portion of human HGFR.

(A) Draw of a molecule generated by the in frame fusion of decoyMET$^{K842E}$ at the N-terminal and scMvDN30 at the C-terminal. (B) Draw of a molecule generated by the in frame fusion of scMvDN30 at the N-terminal and decoyMET$^{K842E}$ at the C-terminal. Between the two moiety a linker has been inserted. The sequence of the linker can be selected from the ones listed in (C). SEMA, PSI, IPT 1-4 are the regions of decoyMET. The star in the IPT 4 represents the mutation K→E at position 842. The anti-HGFR antibody fragment is constituted by two chains jointed by a second linker. VL, variable light region; CL, constant light region; VH, variable heavy region; CH, constant heavy region. The black square represents the Strept-His TAGs included in the recombinant protein for purification/detection purpose.

Figure 10:
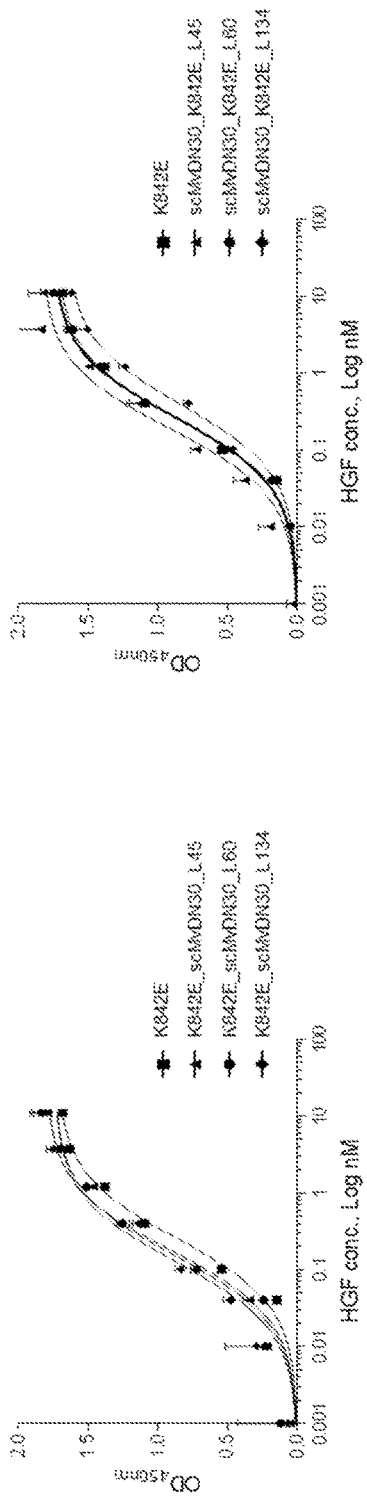
Figure 10:
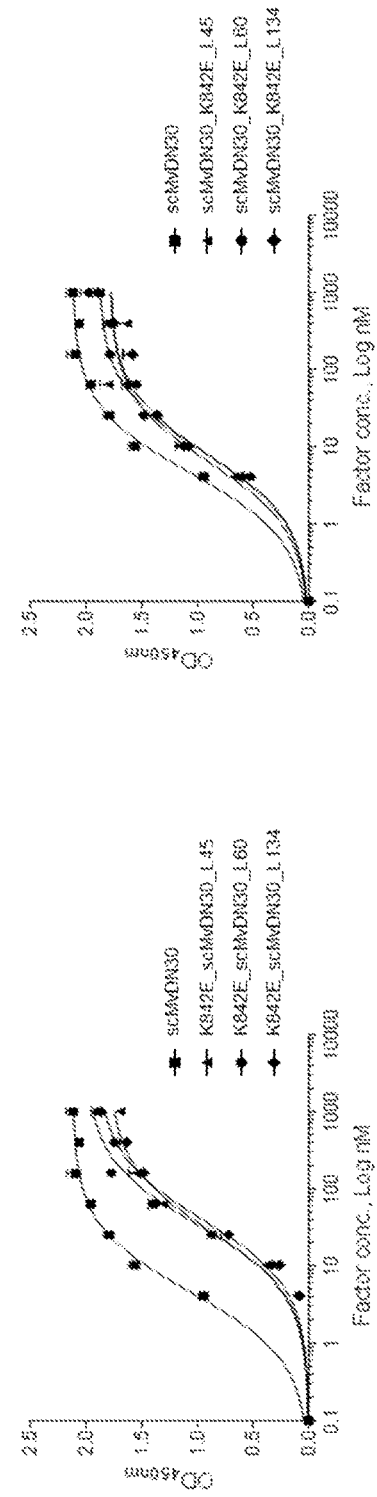

FIG. 10. Binding analysis of the fusion proteins containing an anti-HGFR antibody fragment and an extracellular portion of human HGFR to MET or to HGF.

(A) Binding analysis to HGF by ELISA. Left panel, binding of the fusion proteins containing decoyMET$^{K842E}$ at the N-terminal and scMvDN30 at the C-terminal. Right panel, binding of the fusion proteins containing scMvDN30 at the N-terminal and decoyMET$^{K842E}$ at the C-terminal. The fusion proteins or decoyMET$^{K842E}$ (positive control) were in solid phase. Increasing concentrations of HGF were added in liquid phase. HGF binding was detected using a biotinylated anti-HGF antibody. Each point is the mean of values in triplicate±SD. (B) Binding analysis to MET by ELISA. Left panel, binding of the fusion proteins containing decoyMET$^{K842E}$ at the N-terminal and scMvDN30 at the C-terminal. Right panel, binding of the fusion proteins containing scMvDN30 at the N-terminal and decoyMET$^{K842E}$ at the C-terminal. Wild-type decoyMET was in solid phase and increasing concentrations of the different fusion proteins were in liquid phase; as positive control scMvDN30 was included in the assay. Antibody binding was detected using an HRP-conjugated anti-human k chain antibody. OD, optical density at 450 nm. Each point is the mean of values in triplicate±SD.

Figure 11:
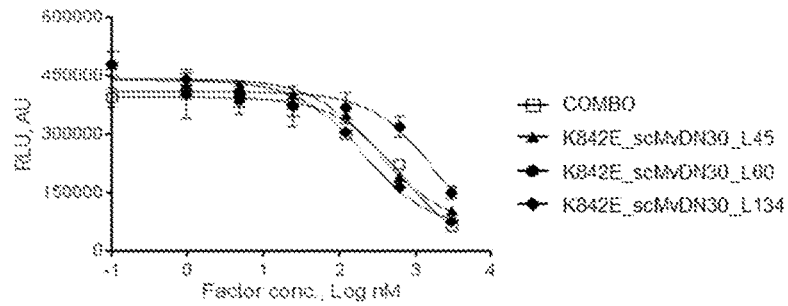
Figure 11:
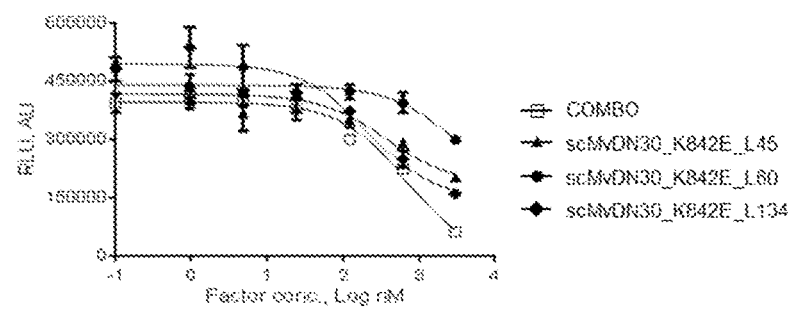

FIG. 11. Inhibition of tumor cell growth upon treatment with the fusion proteins containing an anti-HGFR antibody fragment and an extracellular portion of human HGFR.

(A) Growth of EBC-1 lung carcinoma cells treated with increasing concentrations of the fusion proteins containing decoyMET$^{K842E}$ at the N-terminal and scMvDN30 at the C-terminal. (B) Growth of EBC-1 lung carcinoma cells treated with increasing concentrations of the fusion proteins containing scMvDN30 at the N-terminal and decoyMET$^{K842E}$ at the C-terminal. As positive control equimolar combinations of scMvDN30 and decoyMET$^{K842E}$ (Combo) were included in the assay. Cells were analyzed after 3 days of treatment. Samples are in triplicates, bars represent SD. (C) Table showing $IC_{50}$ values for each fusion protein calculated as the average value from at least three independent experiments, in comparison to the inhibitory activity exerted by MvDN30/decoyK842E in combination.

Figure 12:
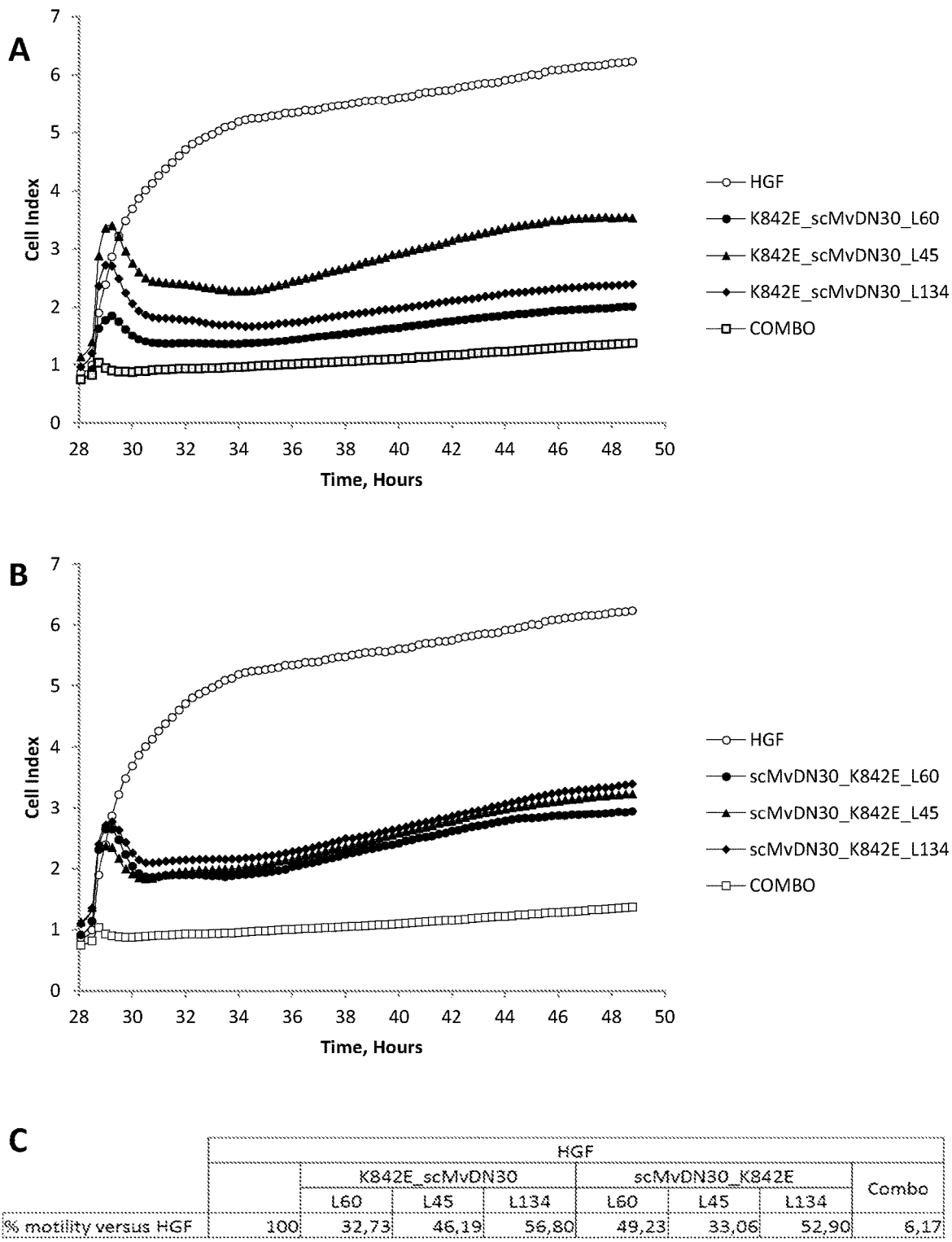

FIG. 12. Inhibition of tumor cell motility upon treatment with the fusion proteins containing an anti-HGFR antibody fragment and an extracellular portion of human HGFR.

HPAF-II cells were pre-incubated with the different fusion proteins (3 μM) and then were stimulated with 6.25 ng/ml HGF. Cell scattering was monitored in real time using an X-CELLigence RTCA device and is expressed as Normalized Cell Index. Samples were in triplicates. (A) Cells treated with the fusion proteins containing decoyMET$^{K842E}$ at the N-terminal and scMvDN30 at the C-terminal. (B) Cells treated with the fusion proteins containing scMvDN30 at the N-terminal and decoyMET$^{K842E}$ at the C-terminal. As positive control equimolar combinations of scMvDN30 and decoyMET$^{K842E}$ (COMBO) were included in the assay. (C) Table showing the percentage of cell motility calculated as the average value from two independent experiments, versus the cells treated with HGF.

Figure 13:
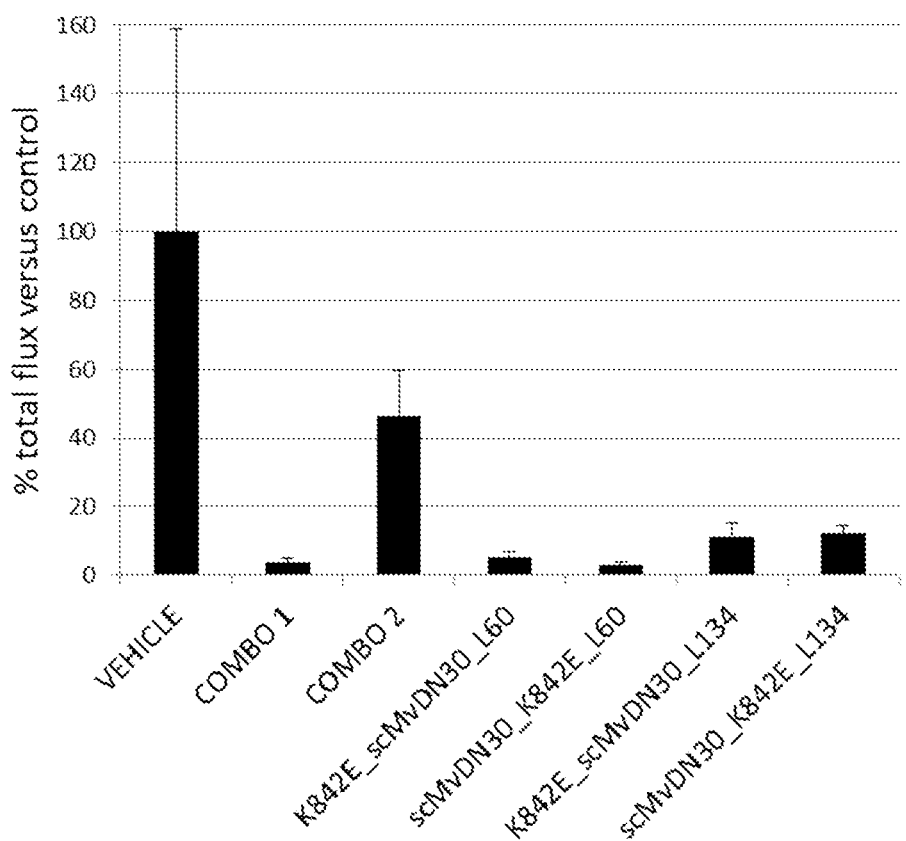

FIG. 13. Fusion proteins containing an anti-HGFR antibody fragment and an extracellular portion of human HGFR reduce metastatic dissemination of pancreatic cancer cells in hHGF-Ki mice.

Luciferase-expressing Capan-1 cells were injected in the pancreas of hHGF-Ki mice and stratified into seven homogeneous groups: VEHICLE (n=14), decoyMET$^{K842E}$ and scMvDN30 in 1:1 combination (two groups), and four groups to test different fusion proteins, containing either decoyMET$^{K842E}$ at the N-terminal and scMvDN30 at the C-terminal or containing scMvDN30 at the N-terminal and decoyMET$^{K842E}$ at the C-terminal. Two different linkers (L60 and L134) were analyzed. COMBO 1 (n=4): MvDN30 delivered 7× week and decoyMET$^{K842E}$ delivered 2× week; COMBO 2 (n=6): MvDN30 delivered 4× week and decoyMET$^{K842E}$ delivered 2× week; K842E scMvDN30 L60 (n=4); scMvDN30 K842E L60 (n=5); K842E scMvDN30 L134 (n=5); K842E scMvDN30 L134 (n=6). All the fusions were delivered 2× week. (A) Table showing the number of mice carrying liver metastasis versus total mice analyzed. Mice were considered positive when bioluminescence detected in the liver by IVIS Spectrum was higher than $10^5$ photons/second. (B) Graph showing the percentage of bioluminescence detected by IVIS Spectrum in the liver of each experimental group versus vehicle treated group.

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The instant disclosure concerns a novel combination of therapeutic agents for the treatment of a tumor and/or metastasis.

The present invention relies on the idea that a higher therapeutic robustness in the treatment of tumors and/or metastasis, preferably metastasis, can be achieved by targeting both HGF and HGFR. The experimental data witnessed herein actually show that vertical inhibition of the MET/HGF axis effectively hinders tumor cell growth, motility and invasion in vitro and significantly reduces metastatic spreading in vivo, providing a combined targeted therapy in a broad spectrum of cancers expressing wild-type MET.

In an embodiment, the present invention concerns an anti-Hepatocyte Growth Factor Receptor (HGFR) antibody fragment in combination with an extracellular portion of human HGFR for use in the treatment of a patient suffering from a tumor and/or metastasis, preferably metastasis, wherein:

(i) the anti-HGFR antibody fragment has only one paratope able to bind to an epitope of the extracellular portion of human HGFR and has antagonist activity towards HGFR, (ii) the extracellular portion of human HGFR is capable of binding to Hepatocyte Growth Factor (HGF) in a stable manner and contains at least one amino acid mutation within the epitope recognized by the anti-HGFR antibody fragment to prevent binding of the anti-HGFR antibody fragment thereto, and (iii) the anti-HGFR antibody fragment and the extracellular portion of human HGFR are suitable for administration to the patient (a) in a protein form or (b) in a nucleic acid form.

In a preferred embodiment, the patient subject to the therapeutic treatment with the combination therapy herein disclosed carries a wild-type MET oncogene (i.e. he/she does not carry genetic alterations in the MET oncogene).

In one or more embodiments, the anti-HGFR antibody fragment contains one light chain variable domain (VL) and one heavy chain variable domain (VH), wherein the light chain and heavy chain variable domains are non-human or humanized, and wherein the light chain variable domain (VL) contains Complementary Determining Regions (CDRs) having the amino acid sequences set forth in SEQ ID No.: 1 to 3, and the heavy chain variable domain (VH) contains CDRs having the amino acid sequences set forth in SEQ ID No.: 4 to 6.

In a further embodiment, the anti-HGFR antibody fragment further contains one human light chain constant domain (CL) and one human heavy chain CH1 constant domain (CH1), the light chain variable domain (VL) being fused to the human light chain constant domain (CL) in the N- to C-terminal direction (thus generating a VL-CL light chain), the heavy chain variable domain (VH) being fused to the human heavy chain CH1 constant domain in the N- to C-terminal direction (thus generating a VH-CH1 heavy chain). In a preferred embodiment, the VL-CL light chain contains, preferably consists of, an amino acid sequence as set forth in SEQ ID No.: 7, and the VH-CH1 heavy chain contains, preferably consists of, an amino acid sequence as set forth in SEQ ID No.: 8.

In different embodiments encompassed by the present invention, the anti-HGFR antibody fragment is in a nucleic acid form. In such a case, the anti-HGFR antibody fragment is encoded by a first and a second nucleic acid molecule, wherein:

(i) the first nucleic acid molecule encodes one light chain variable domain (VL) containing CDRs having the nucleic acid sequences set forth in SEQ ID No.: 9, 10 and 11, and wherein the light chain is non-human or humanized; and (ii) the second nucleic acid molecule encodes one heavy chain variable domain (VH) containing CDRs having the nucleic acid sequences set forth in SEQ ID No.: 12, 13 and 14, and wherein the heavy chain is non-human or humanized.

In a further preferred embodiment, the anti-HGFR antibody fragment is encoded by a first and a second nucleic acid molecule, wherein:

(i) the first nucleic acid molecule encodes (a) one light chain variable domain (VL) containing CDRs having the nucleic acid sequences set forth in SEQ ID No.: 9, 10 and 11, wherein the light chain is non-human or humanized, and (b) one human light chain constant domain (CL) in the 5'- to 3'-terminal direction (i.e. a VL-CL light chain); and (ii) the second nucleic acid molecule encodes (a) one heavy chain variable domain (VH) containing CDRs having the nucleic acid sequences set forth in SEQ ID No.: 12, 13 and 14, wherein the heavy chain is non-human or humanized, and (b) one human heavy chain CH1 constant domain (CH1) in the 5'- to 3'-terminal direction (i.e. a VH-CH1 heavy chain).

In a preferred embodiment, the first nucleic acid molecule (encoding the VL-CL light chain) contains, preferably consists of, a nucleic acid sequence as set forth in SEQ ID No.: 15, and the second nucleic acid molecule (encoding the VH-CH1 heavy chain) contains, preferably consists of, a nucleic acid sequence as set forth in SEQ ID No.: 16.

In a further embodiment encompassed by the present invention, the anti-HGFR antibody fragment is an anti-HGFR single-chain Fab fragment. The anti-HGFR single-Fab fragment contains, preferably consists of, an amino acid sequence as set forth in SEQ ID No.: 17 or the anti-HGFR single-Fab fragment is encoded by a nucleic acid molecule containing, preferably consisting of, a nucleic acid sequence as set forth in SEQ ID No.: 18.

In one or more embodiments, the present invention provides for the extracellular portion of human HGFR containing the SEMA, PSI, IPT-1, IPT-2, IPT-3 and IPT-4 domains.

In a preferred embodiment, the extracellular portion of human HGFR contains, preferably consists of, an amino acid sequence as set forth in SEQ ID No.: 19, wherein one or more of the amino acids between position 797 and position 875 of SEQ ID No.: 19 are mutated. According to the present disclosure, the extracellular portion of human HGFR has a sequence mutated according to the knowledge concerning the anti-HGFR antibody and HGF binding sites on HGFR, in a way that the antibody do not interact with the HGFR, while HGF retains its binding ability to the extracellular portion of human HGFR. In a further preferred embodiment, the extracellular portion of human HGFR has the sequence as set in SEQ ID No.: 20.

In a further embodiment encompassed by the present invention, the extracellular portion of human HGFR is in form of a nucleic acid molecule, wherein the nucleic acid molecule contains, preferably consists of, the nuclei acid sequence as set forth in SEQ ID No.: 21 wherein one or more of the nucleic acids between position 2391 and position 2625 of SEQ ID No.: 21 are mutated. According to the present disclosure, the nucleic acid molecule encodes an extracellular portion of human HGFR having a sequence mutated according to the knowledge concerning the anti-HGFR antibody and HGF binding sites on HGFR, in a way that the antibody do not interact with the HGFR, while HGF retains its binding ability to the extracellular portion of human HGFR. In a further preferred embodiment, the nucleic acid molecule encoding the mutated extracellular portion of human HGFR has the sequence as set in SEQ ID No.: 22.

In different embodiments encompassed by the present invention, the anti-HGFR antibody fragment is conjugated by means of a linker to the extracellular portion of human HGFR in the N- to C-terminal direction, thus generating an anti-HGFR antibody fragment-linker-extracellular portion of human HGFR fusion protein. Alternatively, the extracellular portion of human HGFR is conjugated by means of a linker to the anti-HGFR antibody fragment in the N- to C-terminal direction thus generating an extracellular portion of human HGFR-linker-anti-HGFR antibody fragment fusion protein.

In different embodiments encompassed by the present invention, the nucleic acid molecule encoding the anti-HGFR antibody fragment is linked by means of a nucleic acid molecule encoding a linker to the nucleic acid molecule encoding the extracellular portion of human HGFR in the 5'- to 3'-terminal direction, thus encoding an anti-HGFR antibody fragment-linker-extracellular portion of human HGFR fusion protein. Alternatively, the nucleic acid molecule encoding the extracellular portion of human HGFR is linked by means of a nucleic acid molecule encoding a linker to the nucleic acid molecule encoding the anti-HGFR antibody fragment in the 5'- to 3'-terminal direction, thus encoding an extracellular portion of human HGFR-linker-anti-HGFR antibody fragment fusion protein.

The instant invention therefore provides for a fusion protein comprising in the N- to C-terminal direction:

(i) an anti-HGFR antibody fragment, a linker, and an extracellular portion of human HGFR; or (ii) an extracellular portion of human HGFR, a linker, and an anti-HGFR antibody fragment.

In a preferred embodiment, the fusion protein as defined above contains, preferably consists of, an amino acid sequence selected from any one of SEQ ID No.: 23 to 28.

The instant invention therefore encompasses nucleic acid molecules encoding a fusion protein comprising in the N- to C-terminal direction:

(i) an anti-HGFR antibody fragment, a linker, and an extracellular portion of human HGFR; or (ii) an extracellular portion of human HGFR, a linker, and an anti-HGFR antibody fragment.

In a preferred embodiment, the nucleic acid molecule encoding the fusion protein as defined above contains, preferably consists of, a nucleic acid sequence selected from any one of SEQ ID No.: 29 to 34.

In a further embodiment, the present disclosure concerns a pharmaceutical product comprising, in a single bottle or in two bottles, (a) an anti-Hepatocyte Growth Factor Receptor (HGFR) antibody fragment and a pharmaceutically acceptable vehicle, and (b) an extracellular portion of human HGFR and a pharmaceutically acceptable vehicle, wherein:

(i) the anti-HGFR antibody fragment has only one paratope able to bind to an epitope of the extracellular portion of human HGFR and has antagonist activity towards HGFR, (ii) the extracellular portion of human HGFR is capable of binding to Hepatocyte Growth Factor (HGF) in a stable manner and contains at least one amino acid mutation within the epitope recognized by the anti-HGFR antibody fragment to prevent binding of the anti-HGFR antibody fragment thereto, (iii) the anti-HGFR antibody fragment and the extracellular portion of human HGFR are either in a protein form or in a nucleic acid form.

The pharmaceutical product therefore comprises the anti-HGFR antibody fragment and the extracellular portion of human HGFR having the features, alone or in any respective combination, disclosed above.

In one aspect, the invention provides a method of treating a tumor and/or metastasis in a subject, said method comprising administering to the subject an effective amount of an anti-HGFR antibody fragment in combination with an extracellular portion of human HGFR, whereby said condition is treated.

In one aspect, the invention provides a method of inhibiting the growth of a cell that expresses HGFR, said method comprising contacting said cell with an anti-HGFR antibody fragment in combination with an extracellular portion of human HGFR of the invention thereby causing an inhibition of growth of said cell.

In one aspect, the invention provides a method of therapeutically treating a mammal having a cancerous tumor and/or metastasis, said method comprising administering to said mammal an effective amount of an anti-HGFR antibody fragment in combination with an extracellular portion of human HGFR, thereby effectively treating said mammal.

In one aspect, the invention provides a method for treating a cell proliferative disorder, said method comprising administering to a subject in need of such treatment an effective amount of an anti-HGFR antibody fragment in combination with an extracellular portion of human HGFR, thereby effectively treating or preventing said cell proliferative disorder.

In one aspect, the invention provides a method of therapeutically treating a tumor and/or metastasis in a mammal, wherein the growth of said tumor is at least in part dependent upon a growth potentiating effect of the system HGFR/HGF, as the consequence of either an increase in cell proliferation, a protection from apoptosis, or both. Said method comprises contacting a tumor cell with an effective amount of an anti-HGFR antibody fragment in combination with an effective amount of an extracellular portion of human HGFR of the invention, thereby effectively treating said tumor and/or metastasis.

The tumor, that can be effectively treated with the combination therapy of the present invention, are selected from breast, colorectal, lung, colon, pancreatic, prostate, ovarian, cervical, central nervous system, renal, hepatocellular, bladder, gastric, head and neck tumor cell, papillary carcinoma (e.g. the thyroid gland), melanoma, lymphoma, myeloma, glioma/glioblastoma (e.g. anaplastic astrocytoma, multiforme glioblastoma, anaplastic oligodendroglioma, anaplastic oligodendroastrocytoma), leukemia cell, sarcoma, rhabdomyosarcoma, or a tumor from a cancer of Unknown Primary origin (CUP).

In one embodiment, a cell that is therapeutically targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell. In a further embodiment, a cell that is targeted in a method of the invention is a HGFR expressing cell belonging to the microenvironment sustaining the tumor and/or the metastasis.

The therapeutic methods of the invention can further comprise additional treatment steps. For example, in one embodiment, the therapeutic method further comprises a step wherein a targeted tumor cell and/or tissue is exposed to a radiation treatment or a chemotherapeutic treatment. In a further embodiment, a targeted tumor cell and/or tissue is treated, in addition to an anti-HGFR antibody fragment in combination with an extracellular portion of human HGFR of the invention, with molecules specifically hitting other targets relevant in the maintenance of the transformed phenotype (i.e. anti-EGFR molecules).

The expression "antagonist activity" of the anti-HGFR antibody fragment as used herein refers to the antibody that is able to quench the intracellular signaling elicited in a cell upon HGFR activation. The antagonistic activity of the said antibody can be measured by the evaluation of the HGFR level of expression and/or phosphorylation by conventional techniques such as western blot, immunofluorescence, immunohistochemistry, ELISA, cytofluorimeter analysis or any other method that includes the use of an antibody that recognize specifically HGFR, or the HGFR residues $Tyr^{1234-1235}$ if phosphorylated (ie the major phosphorylation site of $MET^9$, or the HGFR residues $Tyr^{1349/1356}$ if phosphorylated (ie the docking site of $MET^{22}$.

As used herein, the expression "the extracellular portion of human HGFR is capable of binding to human HGF in a stable manner" means that the extracellular portion of human HGFR binds to HGF with a calculated Kd not higher than 100 nM.

The expression "the extracellular portion of human HGFR contains at least one amino acid mutation at the epitope recognized by the anti-HGFR antibody fragment", as used herein, means the presence of one or more mutations (i.e. aminoacid substitutions and/or deletions and/or insertions) within the extra-cellular portion of HGFR, able to induce a modification within the extra-cellular portion of HGFR that prevents the engagement of the above region by the antibody variable domains. The skilled man in view of his common general knowledge (represented i.a. by the possibility to generate a cDNA including a single nucleotide change in a given DNA sequence using specific primers during DNA duplication see Maniatis T. Molecular cloning: A laboratory manual Cold Spring Harbor Laboratory (1982)) does not need further details about the realization of a mutated form of the extracellular portion of human HGFR retaining the ability to bind to human HGF but not to the anti-HGFR antibody fragment.

The present invention must not therefore be interpreted as encompassing only the mutated extra-cellular portion of human HGFR as disclosed herein (i.e. SEQ ID No.: 8), since the skilled man in view of the common general knowledge can produce further mutated versions of the extra-cellular portion of human HGFR having SEQ ID No.: 19 that prevent the bind of the anti-HGFR antibody thereto.

As used herein, the term "single-chain Fab fragment" refers to a single polypeptide encoding for VL, CL, VH, CH1 domains of an antibody, wherein VL and CL can be positioned at the N-terminus of the said polypeptide and joined to the VH and CH1 domains by a flexible linker or VH and CH1 domains can be positioned at the N-terminus of the said polypeptide and linked to VL and CL domains by a flexible linker.

The terms "SEMA", "PSI", "IPT-1", "IPT-2", "IPT-3" and "IPT-4" refer to the HGFR domains constituting the extracellular region of HGFR. Such domains names belong to the common general knowledge of a skilled man as represented i.a. by[4, 13]. SEMA domain is a protein interacting module in common to semaphorins and plexins encompassing the region comprised between aminoacids 25-516 of MET (SEQ ID No.: 19); PSI is a domain in common with plexins, semaphorins, integrins encompassing the region comprised between aminoacids 519-561 of MET (SEQ ID No.: 19); the IPT domain—repeated four times—is a region Immunoglobulin Like in common with plexins and transcription factors, encompassing the region comprised between amino acids 563-934 of MET (SEQ ID No.: 19. In detail IPT repeat 1 covers the amino acid positions 563-656 of SEQ ID No.: 19, IPT repeat 2 covers the amino acid positions 657-740 of SEQ ID No.: 19, IPT repeat 3 covers the amino acid positions 741-837 of SEQ ID No.: 19, IPT repeat 4 covers the amino acid positions 838-934 of SEQ ID No.: 19.

The fusion proteins disclosed herein can be easily manufactured either in the form of proteins or in the form of nucleic acid molecules encoding the fusion proteins by a skilled man in view of the common general knowledge of the field related to the recombinant DNA technology, as represented i.a. by Maniatis T. Molecular cloning: A laboratory manual Cold Spring Harbor Laboratory (1982). As example the following standard procedure can be followed: (i) synthesis of the corresponding cDNA sequence, (ii) insertion of the cDNA into a plasmid suitable for expression in mammalian by conventional recombinant DNA methods, (iii) transient or stable transfection with the above mentioned plasmid of a mammalian cell line, (iv) collection of the culture supernatant, (v) purification by affinity chromatography of the fusion protein. The linkers used to conjugate the two protein sequences, i.e. the anti-HGFR antibody fragment and the extracellular portion of human HGFR, can have different length and/or aminoacid composition, being flexible, rigid or a combination of flexible and rigid regions. The linkers employed in the production of the fusion proteins can be selected from, but not limited to, any one of the amino acid sequences as set forth in SEQ ID No.: 35, 36 and 37. The linkers employed in the production of the nucleic acid molecules encoding the fusion proteins can be selected from, but not limited to, any one of the nucleic acid sequences as set forth in SEQ ID No.: 38, 39 and 40.

In the following the instant invention will be exemplified by referring to a combination of the anti-HGFR antibody fragment containing the CDRs of SEQ ID No.: 1 to 6 belonging to the DN30 monoclonal antibody disclosed in WO 2007/090807 and the extracellular portion of HGFR containing the SEMA, PSI, IPT-1 to IPT-4 domains, briefly named in the following DecoyMET.

The present inventors unexpectedly discovered that monovalent DN30 antibody fragment (MvDN30) and DecoyMET, used in combination, allow dual targeting of ligand and receptor, acting simultaneously on MET-expressing cancer cells and on HGF-secreting tumor stroma and exerting a synergistic effect in the treatment of tumors and/or metastasis.

Pharmacological inhibition of the MET tyrosine kinase receptor in oncogene 'addicted' cancer cells extinguishes cell proliferation and invasion. Accordingly, patients with MET amplified advanced NSCLC, metastatic gastric or esophageal cancer respond to anti-MET therapy[5, 14, 19]. On the other hand, cancer cells without MET genetic alterations exploit the 'physiological' program triggered by the oncogene as an 'expedient' to boost the malignant phenotype[6]. 'Expedience' requires stimulation of wild-type MET by its ligand HGF. In this respect, the contribution of tumor microenvironment to cancer progression and metastasis is becoming increasingly relevant, as experimental evidences suggest that the malignant phenotype does not develop in a strictly cell-autonomous way, but in a rather complex interplay between cancer cells and host stroma. The tumor microenvironment is a significant source of HGF, secreted by stromal cells of mesenchymal origin as an inactive precursor (proHGF). The latter is stored in the extracellular matrix, thanks to its avidity for heparansulfates, and is activated by specific proteases produced either by tumor or stromal cells. Therefore, an excess of biologically active ligand is readily available for binding the MET receptor and triggers the invasive growth signaling cascade in 'non-addicted' cells. The data provided herein show that in conditions of MET 'expedience', a concomitant intervention hitting both sides of the MET/HGF axis results in improved inhibitory activity. Simultaneous targeting was achieved combining a monovalent MET antibody, MvDN30, with a recombinant soluble receptor, decoyMET$^{K842E}$. The data provided herein indicate that there is no redundancy in targeting the same pathway with complementary tools. The two inhibitors were selected on the basis of their mechanisms of action: the antibody induces the physical removal of MET from the cell surface by 'shedding' of the ectodomain. The latter is released in the extracellular environment and acts as 'decoy' for HGF. Exogenous supply of recombinant decoyMET reinforces the HGF-sequestering activity of the endogenous decoyMET generated by MvDN30. To enable the concomitant use of MvDN30 and decoyMET, a modified soluble receptor was generated (decoyMET$^{K842E}$), deficient in MvDN30 interaction but endowed with high affinity binding properties to HGF. The two agents in combination cooperate in a variety of cancer cells, reducing the effective therapeutic dose. Moreover this 'dual strategy' displays a strong synergistic effect, potentially exerting a superior anti-tumor efficacy. MET expression in a subpopulation of stem/progenitor cancer cells has been defined as MET 'inherence', i.e. the physiologic (inherent) HGF-induced intracellular response activated in cancer stem cells—in the absence of genetic lesions—responsible for resistance to targeted therapies, such as Epidermal Growth Factor Receptor (EGFR) inhibitors in colorectal cancer. The notion linking cancer stem cells and resistance to conventional therapies is largely accepted, and the role of microenvironmental HGF in maintaining the stem phenotype of MET-expressing progenitor cells is becoming more and more established. An effective anti-MET treatment, as the combination of MvDN30 and decoyMET$^{K842E}$, represents a therapeutic support to blunt cancer stem cells and to oppose the onset of resistance to targeted therapies.

The role of host microenvironment is difficult to investigate in mouse xenografts due to the limited cross-reactivity between murine stromal-derived factors and specific targets on human cancer cells. This is particularly significant in the case of the HGF/MET system, because murine HGF does not activate human MET. The development of genetically modified mouse strains expressing the Knocked-in human HGF gene (hHGF-Ki mice) circumvented this problem. In this transgenic model, it is shown that concomitant targeting of environmental HGF and its receptor on cancer cells may be an effective therapeutic strategy to hinder malignant progression and metastasis.

Xenografts of pancreatic adenocarcinoma are characterized by precocious metastatic dissemination, occurring very early during tumor development, and are sustained by an abundant stromal compartment. Recently, HGF secreted by pancreatic stellate cells was identified as a factor playing a relevant function in tumor-stroma interaction in this type of malignancy. In an orthotopic mouse model of human pancreatic adenocarcinoma grafted in hHGF-Ki mice, MvDN30 and decoyMET$^{K842E}$ in combination slightly delayed tumor growth, as expected in a model of 'expedience' where MET is not the driver oncogene. On the other hand, the combo treatment proved to be very effective in reducing the metastatic spread, suggesting a possible therapeutic application in non-addicted cancer cells featuring wild-type MET. Epidemiological data show that only 2-3% of epithelial cancers rely on MET oncogenic addiction, either because of gene amplification, rearrangement or mutation[29]. For this reason, a number of clinical trials—addressing unselected populations of cancer patients—failed. On the other hand, the vast majority of carcinomas exploit ligand-dependent wild-type MET activation to unleash the invasive metastatic phenotype in response to hypoxia, ionizing radiation or chemotherapy. Thus these findings suggest that a large cohort of patients—currently unfit to MET targeted therapy due to the absence of a specific genetic lesion—should benefit from treatments encompassing a dual antibody-decoy strategy, that allows optimal blockade of the HGF-driven MET signaling.

Therapeutic compositions comprising the active ingredients of the instant invention, i.e. an anti-HGFR antibody fragment and an extracellular portion of human HGFR, can be prepared either as a single preparation containing the two active ingredients mixed together or as separate preparations, one containing an anti-HGFR antibody fragment and the other an extracellular portion of human HGFR. The active ingredients are prepared for storage by mixing the active ingredient(s) having the desired degree of purity with physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers; antioxidants; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates; chelating agents; sugars; salt-forming counter-ions; metal complexes and/or nonionic surfactants. The formulations disclosed herein may also contain other active compound(s) as necessary for the particular indication being treated, preferably those with complementary activities that do not adversely affect the therapeutic activity of the anti-HGFR antibody fragment and of the extracellular portion of human HGFR. Such molecules are suitably present in combination in amounts that are effective for the purpose intended.

The active ingredient(s) may also be entrapped in microcapsules prepared by means of techniques disclosed i.a. in Remington's Pharmaceutical Sciences 16th edition, Osol, A. Ed. (1980).

The formulations to be used for in vivo administration must be sterile.

Sustained-release preparations may be prepared. Suitable examples of sustained-release preparations include semipermeable matrices of solid hydrophobic polymers containing the active ingredients of the invention, which matrices are in the form of shaped articles, e.g. films, or microcapsule.

The active ingredients of the invention can be used either alone or in combination with another antibody, chemotherapeutic agent(s) (including cocktails of chemotherapeutic agents), other cytotoxic agent(s), anti-angiogenic agent(s), cytokines, and/or growth inhibitory agent(s). Such combined therapies noted above include combined administration (where the two or more agents are included in the same or separate formulations), and separate administration, in which case, administration of the antibody of the invention can occur prior to, and/or following, administration of the adjunct therapy or therapies.

The active ingredients of the present invention (and adjunct therapeutic agent(s)) are administered by any suitable means, including parenteral, subcutaneous, intraperitoneal, intrapulmonary, and intranasal, and, if desired for local treatment, intralesional administration. The active ingredients of the instant invention can be suitably administered by pulse infusion, particularly with declining doses of the active ingredients. Dosing can be by any suitable route, e.g. by injections, such as intravenous or subcutaneous injections, depending in part on whether the administration is brief or chronic. The active ingredients of the invention can be also delivered by gene transfer by mean of viral vectors (i.e. lentiviral vectors), administered locally or systemically or by mean of cell therapy, i.e. delivery by intravenous of local injection of human cells genetically modified by viral vectors transduction (i.e. lentiviral vectors) to express an anti-HGFR antibody fragment and an extracellular portion of human HGFR.

The active ingredients of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The active ingredients of the invention need not be, but may optionally be formulated with one or more agents currently used to prevent or treat the disorder in question. The effective amount of such other agents depends on the amount of active ingredients of the invention present in the formulation, the type of disorder or treatment, and other factors discussed above. These are generally used in the same dosages and with administration routes as used hereinbefore or about from 1 to 99% of the heretofore employed dosages.

For the treatment of disease, the appropriate dosage of the active ingredients of the invention (when used alone or in combination with other agent(s) such as chemotherapeutic agent(s)) will depend on the type of disease to be treated, the severity and course of the disease, whether the active ingredients are administered for preventive or therapeutic purposes, the patient's clinical history and response to the active ingredients of the invention are duly taken into consideration, and at the discretion of the attending physician.

The antibody fragment is suitably administered to the patient at one time or over a series of treatments. Depending on the type and severity of the disease, about 1 mg/kg to 15 mg/kg of antibody is an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. One exemplary dosage of the antibody fragment would be in the range from about 0.05 mg/kg to about 20 mg/kg. Thus, one or more doses of about 0.5 mg/kg, 2.0 mg/kg, 4.0 mg/kg or mg/kg (or any combination thereof) may be administered to the patient. Such doses may be administered intermittently, e. g. every week or every three weeks (e. g. such that the patient receives from about two to about twenty, e. g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays. The extracellular portion of human HGFR must be delivered at the same time of the antibody fragment and must be dosed in proportion to the antibody fragment, preferentially but not limited to, the molar ratio 1:1 antibody fragment:decoyMET, depending on the type and severity of the disease.

Results

Site-Directed Mutagenesis of the DN30-Binding Epitope in decoyMET

Figure 1:
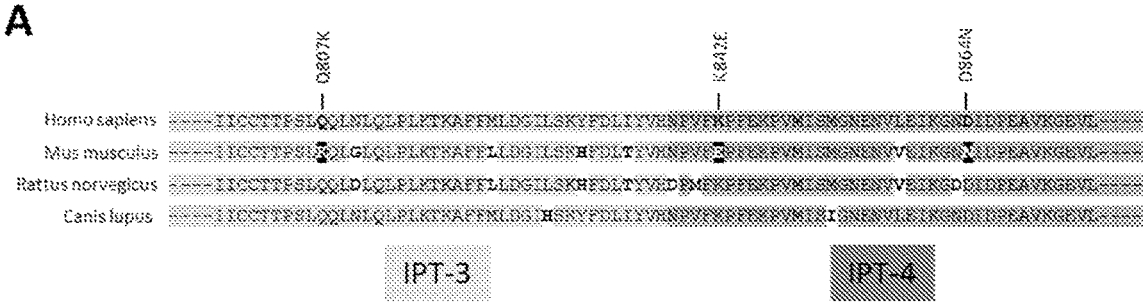
FIG. 1. Generation of a mutated decoyMET receptor that does not bind the DN30 antibody.
Figure 1:
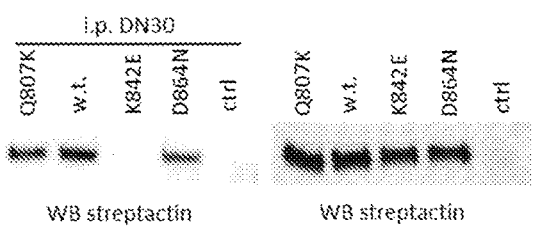
Figure 1:
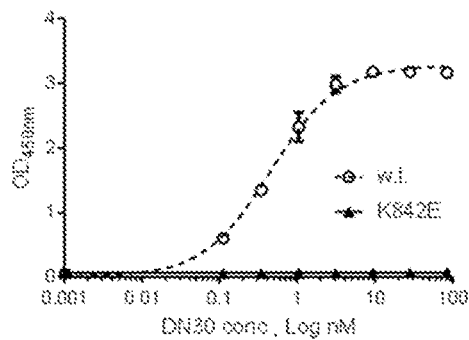

To exploit the activity of MvDN30 antibody and decoyMET in combination, it is mandatory to prevent interaction between the two molecules that would result in mutual neutralization. It has been shown previously that MvDN30 recognizes an epitope within the IPT-4 domain of MET extracellular region at the boundary with the IPT-3 domain[28]. Former studies showed that the parental DN30 antibody, that binds the human receptor with picomolar affinity, also interacts with dog and rat MET[11,23], while it does not cross-react with mouse[21]. Upon alignment of the IPT-3 and IPT-4 aminoacid sequences of the above-mentioned mammalian species, a number of residues were identified that are selectively changed in the mouse (FIG. 1A). To test if human-to-mouse swapping of single aminoacid residues could impair antibody binding, soluble receptors carrying point mutations in the IPT 3-4 domain were generated and tested against the DN30 antibody. Substitution of lysine 842 with glutamic acid generated decoyMET$^{K842E}$, a modified soluble receptor not recognized anymore by the antibody, while all other mutations did not affect the interaction (FIG. 1B). The inability of the antibody to interact with decoyMET$^{K842E}$ was confirmed in ELISA assays, performed with affinity-purified decoys in solid phase and DN-30 antibody in liquid phase (FIG. 1C). Hence, substitution of a basic amino acid at position 842 with an acidic residue resulted in critical perturbation of the binding site, hampering decoyMET$^{K842E}$-antibody interaction.

DecoyMET$^{K842E}$ Binds HGF with High Affinity

The present inventors then investigated if the K842E amino acid substitution interferes with binding of HGF. In ELISA binding assays, the affinity constant of decoyMET$^{K842E}$ for HGF ($K_d \times 1.04 \pm 0.05$ nM) was superimposible with the $K_d$ of $1.44 \pm 0.07$ nM measured for the wild-type decoyMET (FIG. 2A). Finally, the inhibitory activity of decoyMET$^{K842E}$ was tested in an HGF-induced MET phosphorylation assay. As shown in FIG. 2B, wild-type decoyMET and decoyMET$^{K842E}$ inhibited HGF-dependent MET phosphorylation in A549 lung cancer cells with comparable potency. Thus, the K842E substitution does not interfere with the formation of a stable complex with HGF, and leaves the inhibitory activity of the decoy unaffected.

MvDN30 and DecoyMET$^{K842E}$ Cooperate in Inhibition of MET Phosphorylation and Downstream Biological Responses To assess the inhibitory activity elicited by concomitant targeting of the ligand and the receptor on MET signal transduction, MET phosphorylation was tested in the presence of MvDN30 and decoyMET$^{K842E}$, either alone or in combination. To this end, A549 cells, expressing a wild-type MET receptor, were stimulated with nanomolar concentrations of HGF and MET activation was measured by phosphoMET antibodies. Both molecules displayed inhibitory activity, and the combination of the two was more efficient (FIG. 3A). Analysis of downstream signaling transducers confirmed that the combination achieved the most effective inhibition of ERK and AKT activation (FIG. 3B).

On the biological ground, MvDN30 and decoyMET$^{K842E}$ in combination strongly inhibited anchorage-independent colony growth, in cellular models of both autocrine or paracrine HGF stimulation. In the former, U87-MG glioblastoma cells—displaying very efficient colony growth in soft agar due to a MET/HGF autocrine loop-were inhibited by 75% when MvDN30 and decoyMET$^{K842E}$ were used in combination, while colony growth inhibition never exceeded 40% when the two molecules were used as single agents (FIG. 3B). Likewise, the combo treatment completely blocked the formation of A549 soft agar colonies induced by nanomolar concentrations of exogenously-administered HGF, while MvDN30 and decoyMET$^{K842E}$ alone achieved a partial though significant inhibition of colony growth (65% and 74%, respectively, FIG. 3C). Similar results were obtained in invasion assays performed in Matrigel-coated chambers: MvDN30 and decoyMET$^{K842E}$ in combination reduced HGF-driven invasion of HPAF-II human pancreatic adenocarcinoma cells by 85%, while as single agents achieved only 59% and 52% inhibition, respectively (FIG. 3D). In all these biological systems, MvDN30 and decoyMET$^{K842E}$ combination impaired MET phosphorylation more efficaciously than the single treatments (FIG. 4).

To assess if the effect of the two inhibitors is additive or synergistic, a quantitative motility assay was performed. HPAF-II human pancreatic adenocarcinoma cells, expressing wild-type MET, were induced to scatter by HGF. Cell scattering was quantified by measuring the variations of electrical impedance of cell-covered electrodes (X-CELLigence Real Time Cell Analyzer). The two molecules in combination reduced HGF-dependent cell scattering in dose-dependent fashion, starting inhibition at 250 nM and achieving complete blockage in the micromolar range (FIGS. 5 A and B). The Cell Index values measured at the end of the experiment (time=48 h) were normalized on HGF (FIG. 5C) and elaborated with the CalcuSYN software to assess synergism (FIG. 5D): for all concentrations examined, the calculated Combination Index (CI) was well below 0.5 (CI=0.1, 0.09, 0.17 and 0.38 for 0.06, 0.25, 1 and 4 µM, respectively), indicating that MvDN30 and decoyMET$^{K842E}$ display a synergistic behavior[10].

MvDN30 and DecoyMET$^{K842E}$ Attenuate the Invasive Phenotype and Reduce Metastatic Spread The inhibitory activity of MvDN30 and decoyMETK842E in combination was assessed in vivo in mouse models of ligand-driven MET stimulation.

The U87-MG glioblastoma xenograft tumor model of autocrine HGF stimulation was investigated. Cells were injected subcutaneously in NOD-SCID mice; when tumors reached a volume of 80-100 mm³, mice were stratified in homogeneous groups and randomly assigned to 4 treatment arms: Vehicle, MvDN30, decoyMET$^{K842E}$ or the combination of the two. After 22 days of treatment, mice were sacrificed and primary tumors excised for histological examination. While the combo treatment induced only a marginal inhibition of growth (FIG. 6A), reduction of phenotypic hallmarks of tumor invasion was observed (FIG. 6B).

The combo treatment was also challenged in a paracrine model of HGF stimulation. As previously reported, mouse HGF does not activate the human MET receptor[24, 30]. Hence, to test the inhibitory activity of decoyMET$^{K842E}$ in xenografts of human tumors, we exploited a transgenic SCID mouse where the mouse HGF gene was replaced by the human gene (hHGF-Ki)[20]. Human pancreatic adenocarcinoma cells (HPAF-II) were labeled by transduction with the luciferase gene and injected orthotopically in the pancreas of hHGF-Ki mice. Engraftment was checked by analysis of total body luminescence; mice were stratified into homogeneous groups on the basis of bioluminescence values, and randomly assigned to 4 treatment groups: VEHICLE, MvDN30, decoyMET$^{K842E}$ or the combination of the two. Tumor growth was monitored by total body luminescence (FIG. 7A). At sacrifice, 5 weeks after cell injection, tumors were excised and analyzed for MET phosphorylation, proliferation, apoptosis and vimentin/E-cadherin expression (markers of epithelial-mesenchimal transition). Concurrently, lungs were collected for histochemical evaluation of metastatic nodules. The phosphorylated status of MET at Tyrosines 1234-1235 was inhibited by either agents, and the combo treatment elicited a dramatic effect (FIG. 8A). As expected in this model of MET oncogene 'expedience' (i.e. expression of wild-type MET), proliferation as well as apoptosis were modestly affected, and only by the combo treatment (FIGS. 7B and C). Analysis of the ratio between vimentin and E-cadherin showed that the combination treatment pushed cancer cells towards a more epithelial phenotype (FIG. 8B). Accordingly, concomitant administration of MvDN30 and decoyMET$^{K842E}$ significantly inhibited MET-driven metastatic dissemination to the lung (FIG. 8C).

Generation of a Panel of Fusion Proteins Containing an Anti-HGFR Antibody Fragment and an Extracellular Portion of Human HGFR To generate a single cDNA encoding the fusion proteins containing an anti-HGFR antibody fragment and an extracellular portion of human HGFR the present inventors first designed a single chain MvDN30 (ScMvDN30), introducing a linker between the light chain (VL-CL) and the heavy chain (VH-CH1). The linker was flexible, rich in glycine/serine residues and had a length that allowed preferentially the generation of monomeric molecules, constituted by the association of antibody light and heavy chains belonging to the same polypeptide and not from separated polypepdites thus generating dimers and/or multimers. The preferred amino acid sequence of the linker is reported in SEQ ID No.: 36; the corresponding nucleotide sequence is reported in SEQ ID No.: 39. Then ScMvDN30 cDNA was fused in frame with Decoy MET$^{K842E}$. Two groups of fusion proteins has been generated: i) decoyMET$^{K842E}$ was located at the N-terminal and ScMvDN30 at the C-terminal, and ii) scMvDN30 was located at the N-terminal and decoyMet$^{K842E}$ at the C-terminal. To guarantee a high grade of freedom to the entire structure the present inventors introduced a second linker between the two moieties. Three different linkers, modified in amino acid composition and/or length, has been employed: i) L45: a rigid linker of 45 amino acids constituted of two repeats of a sequence rich in alanine and charged residues, SEQ ID No.: 35, the corresponding nucleotide sequence is reported in SEQ ID No.: 38; ii) L60, a flexible linker rich in glycine/serine residues of 60 amino acids SEQ ID No.: 36, the corresponding nucleotide sequence is reported in SEQ ID No.: 39; iii) L134, a combination of flexible and rigid regions of 134 amino acids SEQ ID No.:37, the corresponding nucleotide sequence is reported in SEQ ID No.: 40. A schematic representation of the fusion proteins is reported in FIG. 9.

Fusion Proteins Containing scMvDN30 at the N-Terminal and decoyMET$^{K842E}$ at the C-Terminal Bind with High Affinity Both MET and HGF.

The present inventors investigated by ELISA assays if the new generated fusion proteins maintained the ability of binding both HGF and MET. All the fusion proteins interacted with HGF with an affinity superimposable with the one of decoyMET$^{K842E}$ (FIG. 10A), while the fusion proteins containing scMvDN30 at the C-terminal recognized MET with a lower affinity with respect to the fusions with the antibody located at the N-terminal. The Kd values measured for this latter group of molecules were comparable to the one measured for scMvDN30 alone (FIG. 10B).

The Fusion Proteins Efficiently Inhibited Tumor Cell Growth.

The present inventors assessed the inhibitory properties of the fusion proteins measuring cell growth impairment after three days of treatment in comparison with scMvDN30 combined with decoyMET$^{K842E}$ at equimolar ratio. All the fusion proteins displayed inhibitory properties in a dose-dependent manner. In the reported experiment the fusions with L60 linker were less potent than the other molecules, while L45 and L134 proteins displayed an activity similar to scMvDN30-decoyMET$^{K842E}$ in combination (FIG. 11).

The Fusion Proteins Efficiently Inhibited HGF-Induced Cell Motility.

To assess the effect of the fusion proteins in inhibiting HGF-driven cell motility the present inventors performed the quantitative motility assay with the X-CELLigence Real Time Cell Analyzer using as model the HPAF-II human pancreatic adenocarcinoma cells treated with HGF. All the fusions were able to reduce HGF-dependent cell scattering (FIG. 12).

The Fusion Proteins Reduced Metastatic Spread More Potently than MvDN30 and DecoyMET$^{K842E}$ in Combination The inhibitory activity the fusion proteins was assessed in vivo in the hHGF-Ki SCID mouse model. Human pancreatic adenocarcinoma cells (Capan-I) were labeled by transduction with the luciferase gene and injected orthotopically in the pancreas of the mice. Engraftment was checked by analysis of total body luminescence; mice were stratified into homogeneous groups on the basis of bioluminescence values, and treated with the fusion proteins including the linkers L60 or L134. As references MvDN30 and decoyMET$^{K842E}$ in 1:1 combination and vehicle were included in the experimental groups. At sacrifice, 5 weeks after cell injection, livers were excised and analyzed by IVIS Spectrum to score metastasis. Concomitant administration of MvDN30 and decoyMET$^{K842E}$ significantly inhibited MET-driven metastatic dissemination to the liver; a high efficacy was scored if MvDN30 administration was done daily (COMBO 1 group), while the therapeutic response was significantly reduced if less frequent administrations were applied (COMBO 2 group). This limitation was not scored in the mice treated with the fusion proteins. In fact all of them reduced metastatic dissemination to the liver with high efficacy, even if the delivery was done twice a week (FIG. 13).

Material and Methods

Cell Culture

A549 human lung adenocarcinoma cells, HPAF-II and Capan-1 human pancreatic adenocarcinoma cells, and U87-MG human glioblastoma cells were obtained from ATCC/LGC Standards S.r.l. (Sesto San Giovanni, Italy); EBC-1 human lung carcinoma cells were from the Japanese Collection of Research Bioresources. All the cells were cultured as suggested by the supplier. All cell cultures were tested for *mycoplasma* contamination.

Generation, Expression and Purification of the Anti-HGFR Antibody Fragment

The cDNAs encoding the light chain (VL-CL) and the heavy chain (VH-CH1) of the anti-HGFR antibody fragment able to the recognize an epitope of the extracellular portion of HGFR were generated by gene synthesis performed in outsourcing by Invitrogen GeneArt Gene Synthesis (ThermoFisher) according to the sequences reported in SEQ ID No.: 7 and SEQ ID No.: 8. Antibody fragments were produced by transient transfection of HEK-293T cells with pcDNA3.1 plasmids (cat. #V79020 Invitrogen Corporation, Camarillo, CA) expressing cDNAs encoding for the light chain (VL-CL) and the heavy chain (VH-CH1). Transfected cells were starved for three days and cell culture supernatants containing the soluble receptors were collected. Purification of the recombinant proteins was done by affinity chromatography using HisTrap HP columns (cat. #17524701 GE Healthcare, Freiburg, Germany) according to manifacturer's instructions. Large-scale protein production and purification were performed by U-Protein Express BV (Utrecht, The Netherlands).

Generation, Expression and Purification of Mutated MET Ectodomains cDNA sequences of human MET ectodomains (decoyMET) carrying single aminoacid substitutions were generated using the QuickChange II Site-Directed Mutagenesis Kit (cat. #200524 Agilent Technologies, Santa Clara, CA), following the instruction of the manufacturer. The procedure requires the design of sense and antisense oligonucleotides, that include the desired point mutation. The following oligos has been employed:

```
- mutation K842E:
sn.
                              (SEQ ID No.: 41)
5'-gtacataatcctgtgtttgagccttttgaaaagccagtg-3' as.
                              (SEQ ID No.: 42)
5'-cactggcttttcaaaaggctcaaacacaggattatgtac-3'

- mutation Q807K:
sn.
                              (SEQ ID No.: 43)
5'-ccactccttccctgaaacagctgaatctgcaactcc-3' as.
                              (SEQ ID No.: 44)
5'-ggagttgcagattcagctgtttcagggaaggagtgg-3'

- mutation D864N:
sn.
                              (SEQ ID No.: 45)
5'-ctggaaattaagggaaataatattgaccctgaagcagttaaa gg-3' as.
                              (SEQ ID No.: 46)
5'-cctttaactgcttcagggtcaatattatttcccttaatttcc ag-3'.
```

Engineered soluble receptors were produced by transient transfection of HEK-293T cells with pcDNA3.1 plasmids (cat. #V79020 Invitrogen Corporation, Camarillo, CA) expressing cDNAs encoding for wild-type decoyMET or decoyMET mutants. Transfected cells were starved for three days and cell culture supernatants containing the soluble receptors were collected. Purification of the recombinant proteins was done by affinity chromatography using HisTrap HP columns (cat. #17524701 GE Healthcare, Freiburg, Germany) according to manifacturer's instructions. Large-scale protein production and purification were performed by U-Protein Express BV (Utrecht, The Netherlands).

MET Phosphorylation Assays

Serum-starved A549 were incubated for 24 h with 125 nM MvDN30 or 2 µM decoyMET$^{K842E}$, alone or in combination, and then stimulated with 50 ng/ml HGF (cat. #294-HG-025 R&D Systems) for 2 h at 4° C. Total cellular lysates were analyzed by Western blot using the following primary antibodies: anti-MET phospho-Tyr$^{1234/1235}$ (D26, cat. #3077 Cell Signaling Technology, Beverly, MA); anti-MET (3D4, cat. #08-1366 Invitrogen Corporation); anti-vinculin (clone hVIN-1, cat. #V9131 Sigma Life Science, Saint Louis, MO). Anti-mouse IgG1 (cat. #JI115035003) and anti-rabbit IgG (cat. #JI111035003) HRP-conjugated secondary antibodies were from Jackson ImmunoResearch. (West Grove, PA).

ELISA Binding Assays

For analysis of the interaction between decoyMET and the DN30 mAb, affinity-purified soluble receptors (wild-type decoyMET or decoyMET$^{K842E}$, 100 ng/well) were immobilized on ELISA plates and increasing concentrations of the antibody (0-100 nM) were added in liquid phase. Binding was revealed using HRP-conjugated anti-mouse antibodies (cat. #NA931 GE Healthcare). For analysis of the interaction between and the fusion proteins, affinity-purified decoyMET wild type (100 ng/well) was immobilized on ELISA plates and increasing concentrations of the fusion proteins or scMvDN30 (0-1000 nM) were added in liquid phase. Binding was revealed using HRP-conjugated anti-human k chain antibody (cat. #A7164 Sigma-Aldrich). For analysis of decoyMET or fusion proteins binding to HGF, soluble receptors (100 ng/well) were immobilized on ELISA plates and incubated with increasing concentrations of HGF (0-11 nM) in solution. Binding was detected using the anti-HGF biotinylated antibody (cat. #BAF294 R&D Systems) and revealed with HRP-conjugated streptavidin (cat. #RPN 1231 GE Healthcare).

Colorimetric assay was quantified by the multi-label plate reader VICTOR-X4 (Perkin Elmer Instruments INC., Whaltman, MA). Data were analyzed and fit using Prism software (GraphPad).

In Vitro Biological Assays

For anchorage-independent growth assays, cells were suspended in the appropriate culture medium supplemented with 2% FBS and 0.5% Seaplaque agarose (cat. #50100 BMA, Rockland, ME), and seeded in 48-well plates (500 cells/well) on top of 1% agarose. Fresh medium containing the treatments was supplied twice weekly. A549 cells were treated with 1 µM MvDN30 or 1 µM decoyMET$^{K842E}$, alone or in combination, in the presence of 30 ng/ml HGF. U87-MG cells were treated with 0.5 µM MvDN30 or 1 µM decoyMET$^{K842E}$, alone or in combination. Colonies were stained with tetrazolium salts (cat. #101380 Sigma-Aldrich) after 12 days of culture. Colony growth was determined using Metamorph software (Molecular Devices, Sunnyvale, CA). For cell invasion assays, HPAF-II cells (1.5×10$^5$/well) were suspended in serum-free culture medium in the presence of 0.5 µM MvDN30 or 1 µM decoyMET$^{K842E}$, alone or in combination, and seeded on the upper compartment of transwell chambers pre-coated with 30 µg/well of Matrigel Matrix (cat. #354234 Corning Incorporated, NY). Culture medium supplemented with 2% FBS and 12.5 ng/ml HGF was added to the lower compartment of the chamber. After 24 h, cells on the upper side of the transwell filters were mechanically removed, while cells migrated through the membrane were fixed with 11% glutaraldehyde (cat. #340855 Sigma-Aldrich) and stained with 0.1% Crystal Violet (cat. #C3886 Sigma-Aldrich). Cell invasion was quantified with Image-J software. For cell scattering assays, HPAF-II cells (8000/well) were seeded in 96-well plates in complete culture medium. After 6 h, increasing concentrations (0-4 µM) of MvDN30 or decoyMET$^{K842E}$, alone or in 1:1 combination, were added. After additional 24 h, cells were stimulated with 6.25 ng/ml HGF for 20 h. Cells were fixed with 11% glutaraldehyde and stained with 0.1% Crystal Violet). For real-time cell motility assay, HPAF-II cells were seeded in E-plates (8000/well; Roche Diagnostics, Mannheim, Germany) and treated as above; when applied, the fusion proteins were tested at a concentration of 3 µM. Electrical impedance was monitored continuously for 48 h, with data recording every ten minutes, using a X-Celligence RICA device (Roche Diagnostic). Values are expressed as cell index normalized at the instant of HGF addition.

For anchorage-dependent cell growth, EBC-1 cells were seeded 2000 cells/well in a 96 well plate in 5% FBS culture medium. After 24 hrs, medium was replaced with a fresh one with 5% FBS plus the molecules to be tested (increasing concentrations—from 0,001 to 3 µM). Cell viability was evaluated after 72 hrs using the CellTiter-Glo (cat. #G7573 Promega Corp., Madison, WI), according to the manufacturer's instructions. Chemoluminescence was detected with VICTOR X4.

Immunofluorescence

Immunofluorescence analysis on tumor cells and tissues was performed as described[16,25]. Staining was done with an anti-MET phospho-Tyr$^{1234/1235}$ primary antibody (D26) and revealed by Alexa Fluor 555-conjugated secondary antibody (cat. #A31570 Thermo Fisher Scientific). Cells were counterstained with 488-conjugated phalloidin (cat. #A12379 Thermo Fisher Scientific). All images were captured with a Leica TCS SP5 AOBS confocal laser-scanning microscope (Leica Microsystems). Immunofluorescence acquisition settings were kept constant within each cell line or tumor tissue. Mean Fluorescence Intensity (MFI) was evaluated with ImageJ software, measuring the mean pixel intensity in each channel, background subtracted. For cell lines, phosphoMET MFI was normalized on phalloidin, while for tumors all the signals were normalized on DAPI.

In Vivo Experiments

All animal procedures were performed according to protocols approved by Ethical Committee for animal experimentation of the Fondazione Piemontese per la Ricerca sul Cancro and by Italian Ministry of Health. NOD-SCID mice were purchased from Charles River (Calco, Italy); hHGF-Ki SCID mice) were obtained from AVEO Pharmaceuticals, Cambridge, MA U87-MG cells were injected subcutaneously (2×10$^6$/ mouse) in the right flank of female NOD-SCID mice. Tumor growth was monitored by caliper measurement twice weekly. Tumor volume was calculated using the formula: V=4/3 π (x/2) (y/2) (z/2), where x, y and z are height, width and depth of the tumor mass. When the tumors reached a volume of 80-100 mm$^3$ (day 0), mice were stratified in four homogeneous groups and treated twice weekly by intratumor injection with: vehicle (n=10); MvDN30, 12.5 µg (n=9); K842E, 125 µg (n=9); the combination of the two (n=10). After 22 days of treatment, mice were sacrificed and tumors were excised and embedded in paraffin for histological analysis. Tumor volume fold increase was calculated as the ratio between the value at day 22 and the value at day 0.

HPAF-II or Capan-1 cells were transduced with 100 ng/ml p24 of lentiviral vectors carrying the luciferase gene under the control of the CMV promoter as described[1]. Luciferase-expressing HPAF-II cells ($10^4$/mouse) were injected in the pancreas of 4- to 6-week-old female hHGF-KI SCID mice. After two days, mice were injected intraperitoneally with XenoLight D-Luciferin (150 mg/kg; cat. #122799 Perkin Elmer), stratified into homogeneous groups on the basis of the bioluminescence signal using an IVIS Spectrum CT apparatus (Perkin Elmer), and randomly assigned to 4 treatment arms: vehicle (n=10); MvDN30 (10 mg/kg, n=6); decoyMET$^{K842E}$ (10 mg/kg, n=6); MvDN30+ decoyMET$^{K842E}$ (10+10 mg/kg, n=6). Treatments were administered daily (MvDN30) or every two days (decoyMET$^{K842E}$) by intraperitoneal injection. At sacrifice, after five weeks of treatment, tumors and lungs were explanted. Tumors were embedded in paraffin or OCT and processed for immunohistochemical or immunofluorescence analysis, respectively. Proliferation of tumor cells was determined using a monoclonal anti-Ki67 antibody (MIB-1, cat. #M724001-2 Agilent Technologies) as previously described[18]. Lungs were processed for histochemical analysis and micrometastases were evaluated by light microscopy on paraffin-embedded, HE-stained non sequential sections. For each mouse, ten slides were analyzed; metastatic lesions were scored and their area quantified with ImageJ software.

Luciferase-expressing Capan-1 ($10^6$/mouse) were injected in the pancreas of 4- to 6-week-old female hHGF-Ki SCID mice. Mice stratification was performed as above. Treatment arms: Vehicle (n=14), MvDN30 and decoyMET$^{K842E}$ in combination (10+10 mg/kg; group 1, n=4; group 2 n=6), scMvDN30_K842E_L60 (10 mg/kg; n=5), K842E scMvDN30_L60 (10 mg/kg; n=4), scMvDN30_K842E_L134 (10 mg/kg; n=6), K842E_scMvDN30_L134 (10 mg/kg; n=5). Treatments were administered daily (MvDN30) or every two days (decoyMET$^{K842E}$ and recombinant fusion proteins) by intraperitoneal injection. After five weeks of treatment, animals were sacrificed and livers were collected to measure bioluminescence signals by IVIS spectrum. Mice were considered metastasis positive when bioluminescence detected in the liver by IVIS Spectrum was higher than $10^5$ photons/second.

Statistical Analysis

Average, standard deviation (SD) and standard error of the mean (SEM) were calculated using Microsoft Office Excel 2010 software (Microsoft Corporation, Redmond, Washington). To calculate $K_d$ values, data from ELISA assays were analyzed and fitted according to nonlinear regression, one site binding hyperbola curve, using GraphPad Prism software (GraphPad Software, San Diego, California). To calculate $IC_{50}$ values, data from proliferation assays were analyzed and fitted according to nonlinear regression, sigmoidal dose-response curve, using GraphPad Prism software. Statistical significance was determined using a two-tailed Student's t test. All experiments were repeated at least three times (biological replicates). The in vivo experiments were repeated two times. Figures show one representative experiment.

REFERENCES

1 Amendola M, Venneri M A, Biffi A, Vigna E, Naldini L. Coordinate dual-gene transgenesis by lentiviral vectors carrying synthetic bidirectional promoters. Nat Biotechnol 2005; 23: 108-116.

2 Bertotti A, Burbridge M F, Gastaldi S, Galimi F, Torti D, Medico E et al. Only a subset of Met-activated pathways are required to sustain oncogene addiction. Sci Signal 2009; 2: er11.

3 Blumenschein G R, Mills G B, Gonzalez-Angulo A M. Targeting the hepatocyte growth factor-cMET axis in cancer therapy. J Clin Oncol 2012; 30: 3287-3296.

4 Bork P, Doerks T, Springer T A, Snel B. Domains in plexins: links to integrins and transcription factors. Trends Biochem Sci 1999; 24: 261-263.

5 Catenacci D V, Henderson L, Xiao S Y, Patel P, Yauch R L, Hegde P et al. Durable complete response of metastatic gastric cancer with anti-Met therapy followed by resistance at recurrence. Cancer Discov 2011; 1: 573-579.

6 Comoglio P M, Giordano S, Trusolino L. Drug development of MET inhibitors: targeting oncogene addiction and expedience. Nat Rev Drug Discov 2008; 7: 504-516.

7 Coxon A, Rex K, Meyer S, Sun J, Chen Q, Radinsky R et al. Soluble c-Met receptors inhibit phosphorylation of c-Met and growth of hepatocyte growth factor: c-Met-dependent tumors in animal models. Mol Cancer Ther 2009; 8: 1119-1125.

8 De Bacco F, Casanova E, Medico E, Pellegatta S, Orzan F, Albano R et al. The MET oncogene is a functional marker of a glioblastoma stem cell subtype. Cancer Res 2012; 72: 4537-4550.

9 Ferracini R, Longati P, Naldini L, Vigna E, Comoglio P M. Identification of the major autophosphorylation site of the Met/hepatocyte growth factor receptor tyrosine kinase. J Biol Chem 1991; 266: 19558-19564.

10 Foucquier J, Guedj M. Analysis of drug combinations: current methodological landscape. Pharmacol Res Perspect 2015; 3: e00149.

11 Gallo S, Gatti S, Sala V, Albano R, Costelli P, Casanova E et al. Agonist antibodies activating the Met receptor protect cardiomyoblasts from cobalt chloride-induced apoptosis and autophagy. Cell Death Dis 2014; 5: e1185.

12 Gastaldi S, Sassi F, Accornero P, Torti D, Galimi F, Migliardi G et al. Met signaling regulates growth, repopulating potential and basal cell-fate commitment of mammary luminal progenitors: implications for basal-like breast cancer. Oncogene 2013; 32: 1428-1440.

13 Gherardi E, Love C A, Esnouf R M, Jones E Y. The sema domain. Curr Opin Struct Biol 2004; 14: 669-678.

14 Lennerz J K, Kwak E L, Ackerman A, Michael M, Fox S B, Bergethon K et al. MET amplification identifies a small and aggressive subgroup of esophagogastric adenocarcinoma with evidence of responsiveness to crizotinib. J Clin Oncol 2011; 29: 4803-4810.

15 Luraghi P, Reato G, Cipriano E, Sassi F, Orzan F, Bigatto V et al. MET signaling in colon cancer stem-like cells blunts the therapeutic response to EGFR inhibitors. Cancer Res 2014; 74: 1857-1869.

16 Maione F, Capano S, Regano D, Zentilin L, Giacca M, Casanovas O et al. Semaphorin 3A overcomes cancer hypoxia and metastatic dissemination induced by antiangiogenic treatment in mice. J Clin Invest 2012; 122: 1832-1848.

17 Michieli P, Mazzone M, Basilico C, Cavassa S, Sottile A, Naldini L et al. Targeting the tumor and its microenvironment by a dual-function decoy Met receptor. Cancer Cell 2004; 6: 61-73.

18 Migliardi G, Sassi F, Torti D, Galimi F, Zanella E R, uscarino M et al. Inhibition of MEK and PI3K/mTOR suppresses tumor growth but does not cause tumor regression in patient-derived xenografts of RAS-mutant colorectal carcinomas. Clin Cancer Res 2012; 18: 2515-2525.
19 Ou S H, Kwak E L, Siwak-Tapp C, Dy J, Bergethon K, Clark J W et al. Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol 2011; 6: 942-946.
20 Pennacchietti S, Cazzanti M, Bertotti A, Rideout W M, Han M, Gyuris J et al. Microenvironment-derived HGF overcomes genetically determined sensitivity to anti-MET drugs. Cancer Res 2014; 74: 6598-6609.
21 Petrelli A, Circosta P, Granziero L, Mazzone M, Pisacane A, Fenoglio S et al. Ab-induced ectodomain shedding mediates hepatocyte growth factor receptor down-regulation and hampers biological activity. Proc Natl Acad Sci USA 2006; 103: 5090-5095.
22 Ponzetto C, Bardelli A, Zhen Z, Maina F, dalla Zonca P, Giordano S et al. A multifunctional docking site mediates signaling and transformation by the hepatocyte growth factor/scatter factor receptor family. Cell 1994; 77: 261-271.
23 Prat M, Crepaldi T, Pennacchietti S, Bussolino F, Comoglio P M. Agonistic monoclonal antibodies against the Met receptor dissect the biological responses to HGF. J Cell Sci 1998; 111 (Pt 2): 237-247.
24 Rong S, Oskarsson M, Faletto D, Tsarfaty I, Resau J H, Nakamura T et al. Tumorigenesis induced by coexpression of human hepatocyte growth factor and the human met protooncogene leads to high levels of expression of the ligand and receptor. Cell Growth Differ 1993; 4: 563-569.
25 Serio G, Margaria V, Jensen S, Oldani A, Bartek J, Bussolino F et al. Small GTPase Rab5 participates in chromosome congression and regulates localization of the centromere-associated protein CENP-F to kinetochores. Proc Natl Acad Sci USA 2011; 108: 17337-17342.
26 Tiran Z, Oren A, Hermesh C, Rotman G, Levine Z, Amitai H et al. A novel recombinant soluble splice variant of Met is a potent antagonist of the hepatocyte growth factor/scatter factor-Met pathway. Clin Cancer Res 2008; 14: 4612-4621.
27 Vermeulen L, De Sousa E Melo F, van der Heijden M, Cameron K, de Jong J H, Borovski T et al. Wnt activity defines colon cancer stem cells and is regulated by the microenvironment. Nat Cell Biol 2010; 12: 468-476.
28 Vigna E, Chiriaco C, Cignetto S, Fontani L, Basilico C, Petronzelli F et al. Inhibition of ligand-independent constitutive activation of the Met oncogenic receptor by the engineered chemically-modified antibody DN30. Mol Oncol 2015; 9: 1760-1772.
29 Vigna E, Comoglio P M. Targeting the oncogenic Met receptor by antibodies and gene therapy. Oncogene 2015; 34: 1883-1889.
30 Zhang Y W, Su Y, Lanning N, Gustafson M, Shinomiya N, Zhao P et al. Enhanced growth of human met-expressing xenografts in a new strain of immunocompromised mice transgenic for human hepatocyte growth factor/scatter factor. Oncogene 2005; 24: 101-106.

The invention claimed is:

1. A fusion protein comprising in the N- to C-terminal direction:

an anti-HGFR antibody fragment, a linker, and an extracellular portion of human HGFR; or (ii) an extracellular portion of human HGFR, a linker, and an anti-HGFR antibody fragment, wherein the anti-HGFR antibody fragment (1) has only one paratope able to bind to human HGFR and (2) comprises one light chain variable domain (VL) and one heavy chain variable domain (VH), wherein the light chain variable domain comprises Complementarity Determining Regions (CDRs) having the amino acid sequences set forth in SEQ ID No.: 1 to 3, and the heavy chain variable domain comprises CDRs having the amino acid sequences set forth in SEQ ID No.: 4 to 6, and wherein the extracellular portion of human HGFR (1) comprises the SEMA, PSI, IPT-1, IPT-2, IPT-3 and IPT-4 domains of human HGFR, (2) comprises a glutamate at the residue corresponding to position 842 of SEQ ID NO: 19, and (3) is capable of binding to Hepatocyte Growth Factor (HGF) in a stable manner.

2. The fusion protein according to claim 1, wherein the fusion protein comprises an amino acid sequence selected from any one of SEQ ID No.: 23 to 28.

3. A nucleic acid molecule encoding the fusion protein according to claim 1.

4. A pharmaceutical composition comprising the fusion protein according to claim 1 and a pharmaceutically acceptable vehicle.

5. A pharmaceutical composition comprising the nucleic acid molecule according to claim 3 and a pharmaceutically acceptable vehicle.

6. The fusion protein according to claim 1, wherein the anti-HGFR antibody fragment further comprises one human light chain constant domain and one human heavy chain CH1 constant domain, the light chain variable domain being fused to the human light chain constant domain in the N- to C-terminal direction, and the heavy chain variable domain being fused to the human heavy chain CH1 constant domain in the N- to C-terminal direction.

7. The fusion protein according to claim 1, wherein the anti-HGFR antibody fragment is a single-chain Fab fragment.

8. The fusion protein according to claim 1, wherein the extracellular portion of human HGFR corresponds to the sequence as set forth in residues 25-932 of SEQ ID No.: 19, wherein at least one of the amino acids between position 797 and position 875 of SEQ ID No.: 19 are mutated in order to prevent binding of the anti-HGFR antibody fragment thereto.

9. The fusion protein according to claim 1, wherein the extracellular portion of human HGFR has the sequence set forth in residues 25-932 of SEQ ID No.: 20.

10. The fusion protein of claim 7, wherein the single-chain Fab fragment comprises a linker between the light chain (VL-CL) and the heavy chain (VH-CH1).

11. The fusion protein of claim 7, wherein the linker is flexible and rich in glycine/serine residues.

12. The fusion protein of claim 1, wherein the linker is rigid and rich in alanine and charged residues.

13. The fusion protein of claim 1, wherein the linker is flexible and rich in glycine/serine residues.

14. The fusion protein of claim 1, wherein the linker a combination of flexible and rigid regions.

15. The fusion protein of claim 1, wherein the VH and VL are a humanized VH and VL.

16. A fusion protein comprising in the N- to C-terminal direction:
(i) an anti-HGFR antibody fragment, a linker, and an extracellular portion of human HGFR; or
(ii) an extracellular portion of human HGFR, a linker, and an anti-HGFR antibody fragment,
wherein the anti-HGFR antibody fragment (a) has only one paratope able to bind to human HGFR and (b) comprises one light chain variable domain (VL) and one heavy chain variable domain (VH), wherein the light chain variable domain comprises Complementarity Determining Regions (CDRs) having the amino acid sequences set forth in SEQ ID No.: 1 to 3, and the heavy chain variable domain comprises CDRs having the amino acid sequences set forth in SEQ ID No.: 4 to 6, and
wherein the extracellular portion of human HGFR comprises the SEMA, PSI, IPT-1, IPT-2, IPT-3 and IPT-4 domains of human HGFR, is capable of binding to Hepatocyte Growth Factor (HGF) in a stable manner and contains at least one amino acid mutation within the region corresponding to residues 797-875 of SEQ ID No.: 19 to prevent binding of the anti-HGFR antibody fragment thereto.

17. A fusion protein comprising in the N- to C-terminal direction:
(i) an anti-HGFR antibody fragment, a linker, and an extracellular portion of human HGFR; or
(ii) an extracellular portion of human HGFR, a linker, and an anti-HGFR antibody fragment,
wherein the anti-HGFR antibody fragment (a) has only one paratope able to bind to human HGFR and (b) comprises the light chain variable domain (VL) and heavy chain variable domain (VH) of the DN30 antibody, and
wherein the extracellular portion of human HGFR comprises the SEMA, PSI, IPT-1, IPT-2, IPT-3 and IPT-4 domains of human HGFR, is capable of binding to Hepatocyte Growth Factor (HGF) in a stable manner and contains at least one amino acid mutation within the region corresponding to residues 797-875 of SEQ ID No.: 19 to prevent binding of the anti-HGFR antibody fragment thereto.

18. A method for treatment of a patient suffering from a tumor and/or metastasis, comprising administering to the patient in need thereof a therapeutically effective amount of the fusion protein according to claim 1, wherein the fusion protein is either (a) in a protein form or (b) in a nucleic acid form.

19. The method according to claim 18, wherein the anti-HGFR antibody fragment further comprises one human light chain constant domain and one human heavy chain CH1 constant domain, the light chain variable domain being fused to the human light chain constant domain in the N- to C-terminal direction, and the heavy chain variable domain being fused to the human heavy chain CH1 constant domain in the N- to C-terminal direction.

20. The method according to claim 19, wherein the anti-HGFR antibody fragment is a single-chain Fab fragment.

21. The method according to claim 18, wherein the extracellular portion of human HGFR corresponds to the sequence as set forth in residues 25-932 of SEQ ID No.: 19.

22. The method according to claim 18, wherein the extracellular portion of human HGFR comprises the sequence set forth in residues 25-932 of SEQ ID No.: 20.

23. The method according to claim 18, wherein the anti-HGFR antibody fragment and the extracellular portion of human HGFR are in a nucleic acid form.

24. The method according to claim 18, wherein the fusion protein comprises an amino acid sequence selected from SEQ ID No.: 23, 24, 25, 26, 27 and 28.

25. The method according to claim 18, wherein the patient carries a wild-type MET oncogene.

26. The method according to claim 23, wherein:
the anti-HGFR antibody fragment-linker-extracellular portion of human HGFR fusion protein comprises an amino acid sequence selected from SEQ ID No.: 26, 27 and 28; or
(ii) the extracellular portion of human HGFR-linker-anti-HGFR antibody fragment fusion protein comprises an amino acid sequence selected from SEQ ID No.: 23, 24 and 25.

27. The method according to claim 18, wherein the VH and VL are a humanized VH and VL.

* * * * *

SEQUENCE LISTING

<160> NUMBER OF SEQ ID NOS: 46

<210> SEQ ID NO 1
<211> LENGTH: 10
<212> TYPE: PRT
<213> ORGANISM: artificial
<220> FEATURE:
<223> OTHER INFORMATION: VL-CDR1

<400> SEQUENCE: 1

Gln Ser Val Asp Tyr Asp Gly Gly Ser Tyr
1               5                   10

<210> SEQ ID NO 2
<211> LENGTH: 3
<212> TYPE: PRT
<213> ORGANISM: artificial
<220> FEATURE:
<223> OTHER INFORMATION: VL-CDR2

<400> SEQUENCE: 2

Ala Ala Ser
1

<210> SEQ ID NO 3
<211> LENGTH: 9
<212> TYPE: PRT
<213> ORGANISM: artificial
<220> FEATURE:
<223> OTHER INFORMATION: VL-CDR3

<400> SEQUENCE: 3

Gln Gln Ser Tyr Glu Asp Pro Leu Thr
1               5

```
<210> SEQ ID NO 4
<211> LENGTH: 8
<212> TYPE: PRT
<213> ORGANISM: artificial
<220> FEATURE:
<223> OTHER INFORMATION: VH-CDR1

<400> SEQUENCE: 4

Gly Tyr Thr Phe Thr Ser Tyr Trp
1               5

<210> SEQ ID NO 5
<211> LENGTH: 8
<212> TYPE: PRT
<213> ORGANISM: artificial
<220> FEATURE:
<223> OTHER INFORMATION: VH-CDR2

<400> SEQUENCE: 5

Ile Asn Pro Ser Ser Gly Arg Thr
1               5

<210> SEQ ID NO 6
<211> LENGTH: 5
<212> TYPE: PRT
<213> ORGANISM: artificial
<220> FEATURE:
<223> OTHER INFORMATION: VH-CDR3

<400> SEQUENCE: 6

Ala Ser Arg Gly Tyr
1               5

<210> SEQ ID NO 7
<211> LENGTH: 238
<212> TYPE: PRT
<213> ORGANISM: artificial
<220> FEATURE:
<223> OTHER INFORMATION: aa sequence of VL-CL light chain

<400> SEQUENCE: 7

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
    50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 8
<211> LENGTH: 281
<212> TYPE: PRT
<213> ORGANISM: artificial
<220> FEATURE:
<223> OTHER INFORMATION: aa sequence of VH-CH1 heavy chain

<400> SEQUENCE: 8

Met Gly Trp Ser Tyr Ile Ile Leu Phe Leu Val Ala Thr Ala Thr Asp
1               5                   10                  15

Gly His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Lys Gln Arg Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Val Thr Val Asp Lys Ser Ser Thr
                85                  90                  95

Thr Ala Tyr Met Gln Leu Ser Asn Leu Thr Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Gly
225                 230                 235                 240

Ala Ala Trp Ser His Pro Gln Phe Glu Lys Gly Ala Ala Trp Ser His
                245                 250                 255

Pro Gln Phe Glu Lys Gly Ala Ala Trp Ser His Pro Gln Phe Glu Lys
            260                 265                 270

Gly Ala Ala His His His His His His
        275                 280
```

<210> SEQ ID NO 9
<211> LENGTH: 30
<212> TYPE: DNA
<213> ORGANISM: artificial
<220> FEATURE:
<223> OTHER INFORMATION: VL-CDR1 nucleotide

<400> SEQUENCE: 9
caaagtgttg attatgatgg tggtagttat                              30

<210> SEQ ID NO 10
<211> LENGTH: 9
<212> TYPE: DNA
<213> ORGANISM: artificial
<220> FEATURE:
<223> OTHER INFORMATION: VL-CDR2 nucleotide

<400> SEQUENCE: 10 gctgcatcc                                                      9

<210> SEQ ID NO 11
<211> LENGTH: 27
<212> TYPE: DNA
<213> ORGANISM: artificial
<220> FEATURE:
<223> OTHER INFORMATION: VL-CDR3 nucleotide

<400> SEQUENCE: 11
cagcaaagtt atgaagaccc gctcacg                                 27

<210> SEQ ID NO 12
<211> LENGTH: 24
<212> TYPE: DNA
<213> ORGANISM: artificial
<220> FEATURE:
<223> OTHER INFORMATION: VH-CDR1 nucleotide

<400> SEQUENCE: 12
ggctacacct tcaccagtta ctgg                                    24

<210> SEQ ID NO 13
<211> LENGTH: 24
<212> TYPE: DNA
<213> ORGANISM: artificial
<220> FEATURE:
<223> OTHER INFORMATION: VH-CDR2 nucleotide

<400> SEQUENCE: 13
attaatccta gcagcggtcg tact                                    24

<210> SEQ ID NO 14
<211> LENGTH: 15
<212> TYPE: DNA
<213> ORGANISM: artificial
<220> FEATURE:
<223> OTHER INFORMATION: VH-CDR3 nucleotide

<400> SEQUENCE: 14
gcaagtaggg gctac                                              15

<210> SEQ ID NO 15
<211> LENGTH: 717
<212> TYPE: DNA
<213> ORGANISM: artificial
<220> FEATURE:
<223> OTHER INFORMATION: VL-CL light chain nucleotide

<400> SEQUENCE: 15

```
atggagacag acacaatcct gctatgggtg ctgctgctct gggttccagg ctccactggt    60
gacattgtgc tgacccaatc tccagcttct ttggctgtgt ctctagggca gagggccacc   120
atctcctgca aggccagcca aagtgttgat tatgatggtg gtagttatat gagttggttc   180
caacagagac caggacagcc acccaaactc ctcatctctg ctgcatccaa ccttgaatct   240
ggcatcccag ccaggtttag tggcagtggc tctgggacag acttcaccct caatatccat   300
cctgtggagg aggaggatgt tgcaacctat tactgtcagc aaagttatga agacccgctc   360
acgttcggtg ctggtaccaa ggtggagatc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc tgcgaagtc    660
acccatcagg gcctgagctc gcccgtcaca aagagcttca caggggaga gtgttaa     717
```

<210> SEQ ID NO 16
<211> LENGTH: 846
<212> TYPE: DNA
<213> ORGANISM: artificial
<220> FEATURE:
<223> OTHER INFORMATION: VH-CH1 heavy chain nucleotide

<400> SEQUENCE: 16

```
atgggatgga gctatatcat cctcttttg gtagcaacag ctacagatgg ccactcccag     60
gtccaactgc aacagcctgg gactgaactg gtgaagcctg gggcttcagt gaagctgtcc   120
tgcaaggctt ctggctacac cttcaccagt tactggatac actgggtgaa gcagaggcct   180
ggacaaggcc ttgagtggat tggagagatt aatcctagca gcggtcgtac taactacaac   240
gagaaattca agaacaaggt cacagtgact gtagacaaat cttccaccac agcctacatg   300
caactcagca acctgacatc tgaggactct gcggtctatt actgtgcaag tagggctac   360
tggggccaag gcaccactct cacagtctcc tcagctagca cgaagggccc atcggtcttc   420
cccctggcac cctcctccaa gagcacctct ggggggcacag cggccctggg ctgcctggtc   480
aaggactact cccccgaacc ggtgacggtg tcgtggaact caggcgccct gaccagcggc   540
gtgcacacct tcccggctgt cctacagtcc tcaggactct actccctcag cagcgtggtg   600
accgtgccct ccagcagctt gggcacccag acctacatct gcaacgtgaa tcacaagccc   660
agcaacacca aggtggacaa gaaagttgag cccaaatctt gtgacaaaac tcacacaggt   720
gccgcatgga gcaccccca gttcgaaaaa ggggccgcat ggagccaccc ccagttcgaa   780
aaggggccg catggagcca ccccagttc gaaaaagggg ccgcacacca tcaccatcac   840
cattag                                                               846
```

<210> SEQ ID NO 17
<211> LENGTH: 562
<212> TYPE: PRT
<213> ORGANISM: artificial
<220> FEATURE:
<223> OTHER INFORMATION: scFab

<400> SEQUENCE: 17

```
Met Glu Thr Asp Thr Ile Leu Leu Trp Val Leu Leu Leu Trp Val Pro
1               5                   10                  15
```

-continued

```
Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
 50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys Gly Gly
225                 230                 235                 240

Ser Ser Gly Ser Gly Ser Gly Ser Thr Gly Thr Ser Ser Gly Thr
                245                 250                 255

Gly Thr Ser Ala Gly Thr Thr Gly Thr Ser Ala Ser Thr Ser Gly Ser
            260                 265                 270

Gly Ser Gly Gly Gly Gly Ser Gly Gly Gly Ser Ala Gly Gly
        275                 280                 285

Thr Ala Thr Ala Gly Ala Ser Ser Gly Ser Gln Leu Gln Gln Pro Gly
290                 295                 300

Thr Glu Leu Val Lys Pro Gly Ala Ser Val Lys Leu Ser Cys Lys Ala
305                 310                 315                 320

Ser Gly Tyr Thr Phe Thr Ser Tyr Trp Ile His Trp Val Lys Gln Arg
                325                 330                 335

Pro Gly Gln Gly Leu Glu Trp Ile Gly Glu Ile Asn Pro Ser Ser Gly
            340                 345                 350

Arg Thr Asn Tyr Asn Glu Lys Phe Lys Asn Lys Val Thr Val Thr Val
        355                 360                 365

Asp Lys Ser Ser Thr Thr Ala Tyr Met Gln Leu Ser Asn Leu Thr Ser
370                 375                 380

Glu Asp Ser Ala Val Tyr Tyr Cys Ala Ser Arg Gly Tyr Trp Gly Gln
385                 390                 395                 400

Gly Thr Thr Leu Thr Val Ser Ser Ala Ser Thr Lys Gly Pro Ser Val
                405                 410                 415

Phe Pro Leu Ala Pro Ser Ser Lys Ser Thr Ser Gly Gly Thr Ala Ala
            420                 425                 430
```

| | | | | | | | | | | | | |
|---|---|---|---|---|---|---|---|---|---|---|---|---|
|Leu|Gly|Cys|Leu|Val|Lys|Asp|Tyr|Phe|Pro|Glu|Pro|Val|Thr|Val|Ser|
| | |435| | | |440| | | |445| | | | | |
|Trp|Asn|Ser|Gly|Ala|Leu|Thr|Ser|Gly|Val|His|Thr|Phe|Pro|Ala|Val|
| |450| | | | |455| | | | |460| | | | |
|Leu|Gln|Ser|Ser|Gly|Leu|Tyr|Ser|Leu|Ser|Ser|Val|Val|Thr|Val|Pro|
|465| | | | |470| | | | |475| | | | |480|
|Ser|Ser|Ser|Leu|Gly|Thr|Gln|Thr|Tyr|Ile|Cys|Asn|Val|Asn|His|Lys|
| | | | |485| | | | |490| | | | |495| |
|Pro|Ser|Asn|Thr|Lys|Val|Asp|Lys|Lys|Val|Glu|Pro|Lys|Ser|Cys|Asp|
| | | |500| | | | |505| | | | |510| | |
|Lys|Thr|His|Thr|Thr|Gly|Thr|Arg|Gly|Ala|Ala|Trp|Ser|His|Pro|Gln|
| | |515| | | |520| | | |525| | | | | |
|Phe|Glu|Lys|Gly|Ala|Ala|Trp|Ser|His|Pro|Gln|Phe|Glu|Lys|Gly|Ala|
| |530| | | | |535| | | | |540| | | | |
|Ala|Trp|Ser|His|Pro|Gln|Phe|Glu|Lys|Gly|Ala|Ala|His|His|His|His|
|545| | | | |550| | | | |555| | | | |560|
|His|His| | | | | | | | | | | | | | |

<210> SEQ ID NO 18
<211> LENGTH: 1692
<212> TYPE: DNA
<213> ORGANISM: artificial
<220> FEATURE:
<223> OTHER INFORMATION: scFv nucleotide

<400> SEQUENCE: 18

```
atggagacag acacaatcct gctatgggtg ctgctgctct ggttccagg  ctccactggt      60 gacattgtgc tgacccaatc tccagcttct ttggctgtgt ctctagggca gagggccacc     120
atctcctgca aggccagcca agtgttgat  tatgatggtg gtagttatat gagttggttc     180
caacagagac aggacagcc  acccaaactc ctcatctctg ctgcatccaa ccttgaatct     240
ggcatcccag ccaggtttag tggcagtggc tctgggacag acttcaccct caatatccat     300
cctgtggagg aggaggatgt tgcaacctat tactgtcagc aaagttatga agacccgctc     360
acgttcggtc tggtaccaa  gtggagatc  aaacgaactg tggctgcacc atctgtcttc     420
atcttcccgc atctgatga  gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc  ctgcgaagtc     660 acccatcagg gcctgagctc gcccgtcaca aagagcttca caggggaga  gtgtggtggt     720 tcttcgggtt caggctcggg ctccacaggt acatcgtcat cgggtacagg tacttcagct     780
ggcacaacgg gtacctccgc atctacttcc ggttcaggct ccggaggcgg cggcggctcg     840
ggtggtggtg gatctgccgg cggaaccgca accgcaggcg cttcttctgg ttccgtccaa     900
ctgcagcagc tgggactga  actggtgaag cctggggctt cagtgaagct gtcctgcaag     960
gcttctggct acaccttcac cagttactgg atacactggg tgaagcagag gcctggacaa    1020
ggccttgagt ggattggaga gattaatcct agcagcggtc gtactaacta caacgagaaa    1080
ttcaagaaca aggtcacagt gactgtagac aaatcttcca ccacagccta catgcaactc    1140
agcaacctga catctgagga ctctgcggtc tattactgtg caagtagggg ctactggggc    1200
caaggcacca ctctcacagt ctcctcagct agcacgaagg gcccatcggt cttccccctg    1260
gcaccctcct ccaagagcac ctctgggggc acagcggccc tgggctgcct ggtcaaggac    1320
```

```
tacttccccg aacccgtgac ggtgtcgtgg aactcaggcg ccctgaccag cggcgtgcac    1380 accttccccgg ctgtcctaca gtcctcagga ctctactccc tcagcagcgt ggtgaccgtg    1440
ccctccagca gcttgggcac ccagacctac atctgcaacg tgaatcacaa gcccagcaac    1500
accaaggtgg acaagaaagt tgagcccaaa tcttgtgaca aaactcacac aaccggtacg    1560
cgtggtgccg catggagcca cccccagttc gaaaagggg ccgcatggag ccaccccag    1620 ttcgaaaaag gggccgcatg gagccacccc cagttcgaaa aggggccgc acaccatcac    1680 catcaccatt ag                                                        1692
```

<210> SEQ ID NO 19
<211> LENGTH: 976
<212> TYPE: PRT
<213> ORGANISM: homo sapiens

<400> SEQUENCE: 19

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300
```

```
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720
```

```
Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
        915                 920                 925

Gln Asn Phe Thr Ala Ser Gly Ala Ala Trp Ser His Pro Gln Phe Glu
        930                 935                 940

Lys Gly Ala Ala Trp Ser His Pro Gln Phe Glu Lys Gly Ala Ala Trp
945                 950                 955                 960

Ser His Pro Gln Phe Glu Lys Gly Ala Ala His His His His His His
                965                 970                 975
```

<210> SEQ ID NO 20
<211> LENGTH: 976
<212> TYPE: PRT
<213> ORGANISM: artificial
<220> FEATURE:
<223> OTHER INFORMATION: mutated extracelluair portion of human HGFR

<400> SEQUENCE: 20

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110
```

-continued

```
Lys Asp Asn Ile Asn Met Ala Leu Val Val Asp Thr Tyr Asp Asp
            115                 120                 125
Gln Leu Ile Ser Cys Gly Ser Val Asn Arg Gly Thr Cys Gln Arg His
            130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                    165                 170                 175
Val Ser Ala Leu Gly Ala Lys Val Leu Ser Ser Val Lys Asp Arg Phe
            180                 185                 190
Ile Asn Phe Phe Val Gly Asn Thr Ile Asn Ser Ser Tyr Phe Pro Asp
            195                 200                 205
His Pro Leu His Ser Ile Ser Val Arg Arg Leu Lys Glu Thr Lys Asp
210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                    245                 250                 255
Asn Phe Ile Tyr Phe Leu Thr Val Gln Arg Glu Thr Leu Asp Ala Gln
                260                 265                 270
Thr Phe His Thr Arg Ile Ile Arg Phe Cys Ser Ile Asn Ser Gly Leu
        275                 280                 285
His Ser Tyr Met Glu Met Pro Leu Glu Cys Ile Leu Thr Glu Lys Arg
        290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
        450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
```

-continued

```
            530                 535                 540
Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Glu Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Ala Ser Gly Ala Ala Trp Ser His Pro Gln Phe Glu
        930                 935                 940

Lys Gly Ala Ala Trp Ser His Pro Gln Phe Glu Lys Gly Ala Ala Trp
945                 950                 955                 960
```

Ser His Pro Gln Phe Glu Lys Gly Ala Ala His His His His His
            965                 970                 975

<210> SEQ ID NO 21
<211> LENGTH: 2931
<212> TYPE: DNA
<213> ORGANISM: homo sapiens

<400> SEQUENCE: 21

| | | | | | |
|---|---|---|---|---|---|
| atgaaggccc | ccgctgtgct | tgcacctggc | atcctcgtgc | tcctgtttac | cttggtgcag | 60 |
| aggagcaatg | gggagtgtaa | agaggcacta | gcaaagtccg | agatgaatgt | gaatatgaag | 120 |
| tatcagcttc | ccaacttcac | cgcggaaaca | cccatccaga | atgtcattct | acatgagcat | 180 |
| cacattttcc | ttggtgccac | taactacatt | tatgttttaa | atgaggaaga | ccttcagaag | 240 |
| gttgctgagt | acaagactgg | gcctgtgctg | aacacccag | attgtttccc | atgtcaggac | 300 |
| tgcagcagca | aagccaattt | atcaggaggt | gtttggaaag | ataacatcaa | catggctcta | 360 |
| gttgtgtgaca | cctactatga | tgatcaactc | attagctgtg | gcagcgtcaa | cagagggacc | 420 |
| tgccagcgac | atgtctttcc | ccacaatcat | actgctgaca | tacagtcgga | ggttcactgc | 480 |
| atattctccc | cacagataga | agagcccagc | cagtgtcctg | actgtgtggt | gagcgccctg | 540 |
| ggagccaaag | tcctttcatc | tgtaaaggac | cggttcatca | acttctttgt | aggcaatacc | 600 |
| ataaattctt | cttatttccc | agatcatcca | ttgcattcga | tatcagtgag | aaggctaaag | 660 |
| gaaacgaaag | atggttttat | gttttgacg | gaccagtcct | acattgatgt | tttacctgag | 720 |
| ttcagagatt | cttaccccat | taagtatgtc | catgcctttg | aaagcaacaa | ttttatttac | 780 |
| ttcttgacgg | tccaaaggga | aactctagat | gctcagactt | tcacacaag | aataatcagg | 840 |
| ttctgttcca | taaactctgg | attgcattcc | tacatggaaa | tgcctctgga | gtgtattctc | 900 |
| acagaaaaga | gaaaaagag | atccacaaag | aaggaagtgt | taatatact | tcaggctgcg | 960 |
| tatgtcagca | agcctggggc | ccagcttgct | agacaaatag | gagccagcct | gaatgatgac | 1020 |
| attcttttcg | gggtgttcgc | acaaagcaag | ccagattctg | ccgaaccaat | ggatcgatct | 1080 |
| gccatgtgtg | cattccctat | caaatatgtc | aacgacttct | tcaacaagat | cgtcaacaaa | 1140 |
| aacaatgtga | gatgtctcca | gcattttac | ggacccaatc | atgagcactg | ctttaatagg | 1200 |
| acacttctga | gaaattcatc | aggctgtgaa | gcgcgccgtg | atgaatatcg | aacagagttt | 1260 |
| accacagctt | tgcagcgcgt | tgacttattc | atgggtcaat | tcagcgaagt | cctcttaaca | 1320 |
| tctatatcca | ccttcattaa | aggagacctc | accatagcta | tcttgggac | atcagagggt | 1380 |
| cgcttcatgc | aggttgtggt | ttctcgatca | ggaccatcaa | cccctcatgt | gaattttctc | 1440 |
| ctggactccc | atccagtgtc | tccagaagtg | attgtggagc | atacattaaa | ccaaatggc | 1500 |
| tacacactgg | ttatcactgg | gaagaagatc | acgaagatcc | cattgaatgg | cttgggttgc | 1560 |
| agacatttcc | agtcttgcag | tcaatgcctc | tctgccccac | cctttgttca | gtgtggctgg | 1620 |
| tgccacgaca | aatgtgtgcg | atcggaggaa | tgcctgagcg | gacatggac | tcaacagatc | 1680 |
| tgtctgcctg | caatctacaa | ggttttccca | aatagtgcac | cccttgaagg | agggacaagg | 1740 |
| ctgaccatat | gtggctggga | ctttggattt | cggaggaata | taaatttga | tttaaagaaa | 1800 |
| actagagttc | tccttggaaa | tgagagctgc | accttgactt | aagtgagag | cacgatgaat | 1860 |
| acattgaaat | gcacagttgg | tcctgccatg | aataagcatt | tcaatatgtc | cataattatt | 1920 |
| tcaaatggcc | acgggacaac | acaatacagt | acattctcct | atgtcgatcc | tgtaataaca | 1980 |
| agtatttcgc | cgaaatacgg | tcctatggct | ggtggcactt | tacttacttt | aactggaaat | 2040 |

-continued

```
tacctaaaca gtgggaactc tagacacatt tcaattggtg gaaaaacatg tactttaaaa      2100
agtgtgtcaa acagtattct tgaatgttat accccagccc aaaccatttc aactgagttt      2160
gctgttaaat tgaaaattga cttagccaac cgagagacaa gcatcttcag ttaccgtgaa      2220
gatcccattg tctatgaaat tcatccaacc aaatctttta ttagtggtgg gagcacaata      2280
acaggtgttg ggaaaaacct gaactcagtt agtgtcccga gaatggtcat aaatgtgcat      2340
gaagcaggaa ggaactttac agtggcatgt caacatcgct ctaattcaga gataatctgt      2400
tgtaccactc cttccctgca acagctgaat ctgcaactcc ccctgaaaac caaagccttt      2460
ttcatgttag atggcatcct ttccaaatac tttgatctca tttatgtaca taatcctgtg      2520
tttaagcctt ttgaaaagcc agtgatgatc tcaatgggca tgaaaatgt actggaaatt       2580 aagggaaatg atattgaccc tgaagcagtt aaaggtgaag tgttaaaagt tggaaataag      2640
agctgtgaga atatacactt acattctgaa gccgttttat gcacggtccc caatgacctg      2700
ctgaaattga acagcgagct aaatatagag tggaagcaag caatttcttc aaccgtcctt      2760
ggaaaagtaa tagttcaacc agatcagaat ttcacagcta gcggtgccgc atggagccac      2820
ccccagttcg aaaaggggc cgcatggagc caccccagt tcgaaaaagg ggccgcatgg        2880
agccaccccc agttcgaaaa aggggccgca caccatcacc atcaccatta g               2931
```

<210> SEQ ID NO 22
<211> LENGTH: 2931
<212> TYPE: DNA
<213> ORGANISM: artificial
<220> FEATURE:
<223> OTHER INFORMATION: mutated extracellular portion of human HGFR nucleotide

<400> SEQUENCE: 22

```
atgaaggccc ccgctgtgct tgcacctggc atcctcgtgc tcctgtttac cttggtgcag        60
aggagcaatg gggagtgtaa agaggcacta gcaaagtccg agatgaatgt gaatatgaag       120
tatcagcttc ccaacttcac cgcggaaaca cccatccaga atgtcattct acatgagcat       180
cacattttcc ttggtgccac taactacatt tatgttttaa atgaggaaga ccttcagaag       240
gttgctgagt acaagactgg gcctgtgctg aacacccag attgtttccc atgtcaggac        300
tgcagcagca agccaatttt atcaggaggt gtttggaaag ataacatcaa catggctcta       360
gttgtggaca cctactatga tgatcaactc attagctgtg gcagcgtcaa cagagggacc       420
tgccagcgac atgtctttcc ccacaatcat actgctgaca tacagtcgga ggttcactgc       480
atattctccc cacagataga agagcccagc cagtgtcctg actgtgtggt gagcgccctg       540
ggagccaaag tcctttcatc tgtaaaggac cggttcatca acttctttgt aggcaatacc       600
ataaattctt cttatttccc agatcatcca ttgcattcga tatcagtgag aaggctaaag       660
gaaacgaaag atggttttat gttttttgacg gaccagtcct acattgatgt tttacctgag       720
ttcagagatt cttaccccat taagtatgtc catgcctttg aaagcaacaa ttttatttac       780
ttcttgacgg tccaaaggga aactctagat gctcagactt tcacacaag aataatcagg       840 ttctgttcca taaactctgg attgcattcc tacatggaaa tgcctctgga gtgtattctc       900
acagaaaaga gaaaaaagag atccacaaag aaggaagtgt taatatact tcaggctgcg       960 tatgtcagca agcctggggc ccagcttgct agacaaatag agccagcct gaatgatgac      1020 attctttttcg gggtgttcgc acaaagcaag ccagattctg ccgaaccaat ggatcgatct     1080
gccatgtgtg cattccctat caaatatgtc aacgacttct tcaacaagat cgtcaacaaa     1140
```

-continued

```
aacaatgtga gatgtctcca gcattttttac ggacccaatc atgagcactg ctttaatagg    1200
acacttctga gaaattcatc aggctgtgaa gcgcgccgtg atgaatatcg aacagagttt    1260
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggttgc    1560
agacatttcc agtcttgcag tcaatgcctc tctgccccac cctttgttca gtgtggctgg    1620
tgccacgaca atgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtcgatcc tgtaataaca    1980
agtatttcgc cgaaatacgg tcctatggct ggtggcactt tacttacttt aactggaaat    2040
tacctaaaca gtgggaactc tagacacatt tcaattggtg aaaaacatg tactttaaaa    2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaactcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atggcatcct ttccaaatac tttgatctca tttatgtaca taatcctgtg    2520
tttgagcctt ttgaaaagcc agtgatgatc tcaatgggca atgaaaatgt actgaaatt    2580 aagggaaatg atattgaccc tgaagcagtt aaaggtgaag tgttaaagt tggaaataag    2640 agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacagcta gcggtgccgc atggagccac    2820
ccccagttcg aaaaggggc cgcatggagc caccccagt tcgaaaaagg ggccgcatgg    2880
agccaccccc agttcgaaaa aggggccgca caccatcacc atcaccatta g            2931
```

<210> SEQ ID NO 23
<211> LENGTH: 1518
<212> TYPE: PRT
<213> ORGANISM: artificial
<220> FEATURE:
<223> OTHER INFORMATION: decoyMET-linker-antibody
    aa seq K842E-linker L45-scMvDN30

<400> SEQUENCE: 23

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
```

```
            35                  40                  45
Glu Thr Pro Ile Gln Asn Val Ile Leu His Glu His His Ile Phe Leu
 50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
        210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460
```

-continued

```
Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Glu Pro Phe Glu Lys Pro Val
                835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880
```

```
Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
        915                 920                 925

Gln Asn Phe Thr Ala Glu Ala Ala Lys Glu Ala Ala Lys Glu
    930                 935                 940

Ala Ala Ala Lys Glu Ala Ala Lys Ala Ala Glu Ala Ala Ala
945                 950                 955                 960

Lys Glu Ala Ala Ala Lys Glu Ala Ala Ala Lys Glu Ala Ala Ala Lys
                965                 970                 975

Ala Asp Ile Val Leu Thr Gln Ser Pro Ala Ser Leu Ala Val Ser Leu
            980                 985                 990

Gly Gln Arg Ala Thr Ile Ser Cys Lys Ala Ser Gln Ser Val Asp Tyr
        995                 1000                1005

Asp Gly Gly Ser Tyr Met Ser Trp Phe Gln Gln Arg Pro Gly Gln
    1010                1015                1020

Pro Pro Lys Leu Leu Ile Ser Ala Ala Ser Asn Leu Glu Ser Gly
    1025                1030                1035

Ile Pro Ala Arg Phe Ser Gly Ser Gly Ser Gly Thr Asp Phe Thr
    1040                1045                1050

Leu Asn Ile His Pro Val Glu Glu Asp Val Ala Thr Tyr Tyr
    1055                1060                1065

Cys Gln Gln Ser Tyr Glu Asp Pro Leu Thr Phe Gly Ala Gly Thr
    1070                1075                1080

Lys Val Glu Ile Lys Arg Thr Val Ala Ala Pro Ser Val Phe Ile
    1085                1090                1095

Phe Pro Pro Ser Asp Glu Gln Leu Lys Ser Gly Thr Ala Ser Val
    1100                1105                1110

Val Cys Leu Leu Asn Asn Phe Tyr Pro Arg Glu Ala Lys Val Gln
    1115                1120                1125

Trp Lys Val Asp Asn Ala Leu Gln Ser Gly Asn Ser Gln Glu Ser
    1130                1135                1140

Val Thr Glu Gln Asp Ser Lys Asp Ser Thr Tyr Ser Leu Ser Ser
    1145                1150                1155

Thr Leu Thr Leu Ser Lys Ala Asp Tyr Glu Lys His Lys Val Tyr
    1160                1165                1170

Ala Cys Glu Val Thr His Gln Gly Leu Ser Ser Pro Val Thr Lys
    1175                1180                1185

Ser Phe Asn Arg Gly Glu Cys Gly Gly Ser Ser Gly Ser Gly Ser
    1190                1195                1200

Gly Ser Thr Gly Thr Ser Ser Gly Thr Gly Ser Ala Gly
    1205                1210                1215

Thr Thr Gly Thr Ser Ala Ser Thr Ser Gly Ser Gly Ser Gly Gly
    1220                1225                1230

Gly Gly Gly Ser Gly Gly Gly Gly Ser Ala Gly Thr Ala Thr
    1235                1240                1245

Ala Gly Ala Ser Ser Gly Ser Val Gln Leu Gln Gln Pro Gly Thr
    1250                1255                1260

Glu Leu Val Lys Pro Gly Ala Ser Val Lys Leu Ser Cys Lys Ala
    1265                1270                1275

Ser Gly Tyr Thr Phe Thr Ser Tyr Trp Ile His Trp Val Lys Gln
```

```
            1280                1285                1290
Arg  Pro  Gly  Gln  Gly  Leu  Glu  Trp  Ile  Gly  Ile  Asn  Pro  Ser
     1295                1300                1305

Ser  Gly  Arg  Thr  Asn  Tyr  Asn  Glu  Lys  Phe  Lys  Asn  Lys  Val  Thr
     1310                1315                1320

Val  Thr  Val  Asp  Lys  Ser  Ser  Thr  Thr  Ala  Tyr  Met  Gln  Leu  Ser
     1325                1330                1335

Asn  Leu  Thr  Ser  Glu  Asp  Ser  Ala  Val  Tyr  Tyr  Cys  Ala  Ser  Arg
     1340                1345                1350

Gly  Tyr  Trp  Gly  Gln  Gly  Thr  Leu  Thr  Val  Ser  Ser  Ala  Ser
     1355                1360                1365

Thr  Lys  Gly  Pro  Ser  Val  Phe  Pro  Leu  Ala  Pro  Ser  Ser  Lys  Ser
     1370                1375                1380

Thr  Ser  Gly  Gly  Thr  Ala  Ala  Leu  Gly  Cys  Leu  Val  Lys  Asp  Tyr
     1385                1390                1395

Phe  Pro  Glu  Pro  Val  Thr  Val  Ser  Trp  Asn  Ser  Gly  Ala  Leu  Thr
     1400                1405                1410

Ser  Gly  Val  His  Thr  Phe  Pro  Ala  Val  Leu  Gln  Ser  Ser  Gly  Leu
     1415                1420                1425

Tyr  Ser  Leu  Ser  Ser  Val  Val  Thr  Val  Pro  Ser  Ser  Ser  Leu  Gly
     1430                1435                1440

Thr  Gln  Thr  Tyr  Ile  Cys  Asn  Val  Asn  His  Lys  Pro  Ser  Asn  Thr
     1445                1450                1455

Lys  Val  Asp  Lys  Lys  Val  Glu  Pro  Lys  Ser  Cys  Asp  Lys  Thr  His
     1460                1465                1470

Thr  Thr  Arg  Gly  Ala  Ala  Trp  Ser  His  Pro  Gln  Phe  Glu  Lys  Gly
     1475                1480                1485

Ala  Ala  Trp  Ser  His  Pro  Gln  Phe  Glu  Lys  Gly  Ala  Ala  Trp  Ser
     1490                1495                1500

His  Pro  Gln  Phe  Glu  Lys  Gly  Ala  Ala  His  His  His  His  His  His
     1505                1510                1515

<210> SEQ ID NO 24
<211> LENGTH: 1533
<212> TYPE: PRT
<213> ORGANISM: artificial
<220> FEATURE:
<223> OTHER INFORMATION: decoyMET-linker-antibody
      aa seq K842E-linker L60-scMvDN30

<400> SEQUENCE: 24

Met  Lys  Ala  Pro  Ala  Val  Leu  Ala  Pro  Gly  Ile  Leu  Val  Leu  Leu  Phe
1              5                   10                  15

Thr  Leu  Val  Gln  Arg  Ser  Asn  Gly  Glu  Cys  Lys  Glu  Ala  Leu  Ala  Lys
           20                  25                  30

Ser  Glu  Met  Asn  Val  Asn  Met  Lys  Tyr  Gln  Leu  Pro  Asn  Phe  Thr  Ala
               35                  40                  45

Glu  Thr  Pro  Ile  Gln  Asn  Val  Ile  Leu  His  Glu  His  Ile  Phe  Leu
           50                  55                  60

Gly  Ala  Thr  Asn  Tyr  Ile  Tyr  Val  Leu  Asn  Glu  Glu  Asp  Leu  Gln  Lys
65                  70                  75                  80

Val  Ala  Glu  Tyr  Lys  Thr  Gly  Pro  Val  Leu  Glu  His  Pro  Asp  Cys  Phe
                   85                  90                  95

Pro  Cys  Gln  Asp  Cys  Ser  Ser  Lys  Ala  Asn  Leu  Ser  Gly  Gly  Val  Trp
                   100                 105                 110
```

-continued

```
Lys Asp Asn Ile Asn Met Ala Leu Val Val Asp Thr Tyr Asp Asp
            115                 120                 125
Gln Leu Ile Ser Cys Gly Ser Val Asn Arg Gly Thr Cys Gln Arg His
    130                 135                 140
Val Phe Pro His Asn His Thr Ala Asp Ile Gln Ser Glu Val His Cys
145                 150                 155                 160
Ile Phe Ser Pro Gln Ile Glu Glu Pro Ser Gln Cys Pro Asp Cys Val
                165                 170                 175
Val Ser Ala Leu Gly Ala Lys Val Leu Ser Ser Val Lys Asp Arg Phe
            180                 185                 190
Ile Asn Phe Phe Val Gly Asn Thr Ile Asn Ser Ser Tyr Phe Pro Asp
        195                 200                 205
His Pro Leu His Ser Ile Ser Val Arg Arg Leu Lys Glu Thr Lys Asp
    210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
            260                 265                 270
Thr Phe His Thr Arg Ile Ile Arg Phe Cys Ser Ile Asn Ser Gly Leu
        275                 280                 285
His Ser Tyr Met Glu Met Pro Leu Glu Cys Ile Leu Thr Glu Lys Arg
    290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
        355                 360                 365
Tyr Val Asn Asp Phe Phe Asn Lys Ile Val Asn Lys Asn Asn Val Arg
    370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
    450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
```

```
            530                 535                 540
Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Glu Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
                915                 920                 925

Gln Asn Phe Thr Gly Gly Ser Ser Gly Ser Gly Ser Gly Ser Thr Gly
                930                 935                 940

Thr Ser Ser Ser Gly Thr Gly Thr Ser Ala Gly Thr Thr Gly Thr Ser
945                 950                 955                 960
```

```
Ala Ser Thr Ser Gly Ser Gly Ser Gly Gly Gly Gly Ser Gly Gly
                965             970                 975

Gly Gly Ser Ala Gly Gly Thr Ala Thr Ala Gly Ala Ser Ser Gly Ser
            980             985                 990

Asp Ile Val Leu Thr Gln Ser Pro Ala Ser Leu Ala Val Ser Leu Gly
            995             1000                1005

Gln Arg Ala Thr Ile Ser Cys Lys Ala Ser Gln Ser Val Asp Tyr
        1010            1015            1020

Asp Gly Gly Ser Tyr Met Ser Trp Phe Gln Arg Pro Gly Gln
        1025            1030            1035

Pro Pro Lys Leu Leu Ile Ser Ala Ala Ser Asn Leu Glu Ser Gly
        1040            1045            1050

Ile Pro Ala Arg Phe Ser Gly Ser Gly Ser Gly Thr Asp Phe Thr
        1055            1060            1065

Leu Asn Ile His Pro Val Glu Glu Asp Val Ala Thr Tyr Tyr
        1070            1075            1080

Cys Gln Gln Ser Tyr Glu Asp Pro Leu Thr Phe Gly Ala Gly Thr
        1085            1090            1095

Lys Val Glu Ile Lys Arg Thr Val Ala Ala Pro Ser Val Phe Ile
        1100            1105            1110

Phe Pro Pro Ser Asp Glu Gln Leu Lys Ser Gly Thr Ala Ser Val
        1115            1120            1125

Val Cys Leu Leu Asn Asn Phe Tyr Pro Arg Glu Ala Lys Val Gln
        1130            1135            1140

Trp Lys Val Asp Asn Ala Leu Gln Ser Gly Asn Ser Gln Glu Ser
        1145            1150            1155

Val Thr Glu Gln Asp Ser Lys Asp Ser Thr Tyr Ser Leu Ser Ser
        1160            1165            1170

Thr Leu Thr Leu Ser Lys Ala Asp Tyr Glu Lys His Lys Val Tyr
        1175            1180            1185

Ala Cys Glu Val Thr His Gln Gly Leu Ser Ser Pro Val Thr Lys
        1190            1195            1200

Ser Phe Asn Arg Gly Glu Cys Gly Gly Ser Gly Ser Gly Ser
        1205            1210            1215

Gly Ser Thr Gly Thr Ser Ser Gly Thr Gly Thr Ser Ala Gly
        1220            1225            1230

Thr Thr Gly Thr Ser Ala Ser Thr Ser Gly Ser Gly Ser Gly Gly
        1235            1240            1245

Gly Gly Gly Ser Gly Gly Gly Gly Ser Ala Gly Gly Thr Ala Thr
        1250            1255            1260

Ala Gly Ala Ser Ser Gly Ser Val Gln Leu Gln Gln Pro Gly Thr
        1265            1270            1275

Glu Leu Val Lys Pro Gly Ala Ser Val Lys Leu Ser Cys Lys Ala
        1280            1285            1290

Ser Gly Tyr Thr Phe Thr Ser Tyr Trp Ile His Trp Val Lys Gln
        1295            1300            1305

Arg Pro Gly Gln Gly Leu Glu Trp Ile Gly Glu Ile Asn Pro Ser
        1310            1315            1320

Ser Gly Arg Thr Asn Tyr Asn Glu Lys Phe Lys Asn Lys Val Thr
        1325            1330            1335

Val Thr Val Asp Lys Ser Ser Thr Thr Ala Tyr Met Gln Leu Ser
        1340            1345            1350
```

-continued

```
Asn Leu Thr Ser Glu Asp Ser Ala Val Tyr Tyr Cys Ala Ser Arg
    1355                1360                1365

Gly Tyr Trp Gly Gln Gly Thr Thr Leu Thr Val Ser Ser Ala Ser
1370                1375                1380

Thr Lys Gly Pro Ser Val Phe Pro Leu Ala Pro Ser Ser Lys Ser
1385                1390                1395

Thr Ser Gly Gly Thr Ala Ala Leu Gly Cys Leu Val Lys Asp Tyr
1400                1405                1410

Phe Pro Glu Pro Val Thr Val Ser Trp Asn Ser Gly Ala Leu Thr
    1415                1420                1425

Ser Gly Val His Thr Phe Pro Ala Val Leu Gln Ser Ser Gly Leu
    1430                1435                1440

Tyr Ser Leu Ser Ser Val Val Thr Val Pro Ser Ser Ser Leu Gly
    1445                1450                1455

Thr Gln Thr Tyr Ile Cys Asn Val Asn His Lys Pro Ser Asn Thr
1460                1465                1470

Lys Val Asp Lys Lys Val Glu Pro Lys Ser Cys Asp Lys Thr His
    1475                1480                1485

Thr Thr Arg Gly Ala Ala Trp Ser His Pro Gln Phe Glu Lys Gly
    1490                1495                1500

Ala Ala Trp Ser His Pro Gln Phe Glu Lys Gly Ala Ala Trp Ser
1505                1510                1515

His Pro Gln Phe Glu Lys Gly Ala Ala His His His His His His
    1520                1525                1530
```

<210> SEQ ID NO 25
<211> LENGTH: 1607
<212> TYPE: PRT
<213> ORGANISM: artificial
<220> FEATURE:
<223> OTHER INFORMATION: decoyMET-linker-antibody
      aa seq K842E-linker L134-scMvDN30

<400> SEQUENCE: 25

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175
```

```
Val Ser Ala Leu Gly Ala Lys Val Leu Ser Val Lys Asp Arg Phe
            180                 185                 190
Ile Asn Phe Phe Val Gly Asn Thr Ile Asn Ser Ser Tyr Phe Pro Asp
        195                 200                 205
His Pro Leu His Ser Ile Ser Val Arg Arg Leu Lys Glu Thr Lys Asp
    210                 215                 220
Gly Phe Met Phe Leu Thr Asp Gln Ser Tyr Ile Asp Val Leu Pro Glu
225                 230                 235                 240
Phe Arg Asp Ser Tyr Pro Ile Lys Tyr Val His Ala Phe Glu Ser Asn
                245                 250                 255
Asn Phe Ile Tyr Phe Leu Thr Val Gln Arg Glu Thr Leu Asp Ala Gln
            260                 265                 270
Thr Phe His Thr Arg Ile Ile Arg Phe Cys Ser Ile Asn Ser Gly Leu
        275                 280                 285
His Ser Tyr Met Glu Met Pro Leu Glu Cys Ile Leu Thr Glu Lys Arg
    290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
            340                 345                 350
Ser Ala Glu Pro Met Asp Arg Ser Ala Met Cys Ala Phe Pro Ile Lys
        355                 360                 365
Tyr Val Asn Asp Phe Phe Asn Lys Ile Val Asn Lys Asn Asn Val Arg
    370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
    450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
            580                 585                 590
```

```
Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
        820                 825                 830

Leu Ile Tyr Val His Asn Pro Val Phe Glu Pro Phe Glu Lys Pro Val
    835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
    915                 920                 925

Gln Asn Phe Thr Gly Gly Gly Ser Gly Gly Gly Ser Gly Gly
930                 935                 940

Gly Gly Ser Ala Glu Ala Trp Tyr Asn Leu Gly Asn Ala Tyr Tyr Lys
945                 950                 955                 960

Gln Gly Asp Tyr Gln Lys Ala Ile Glu Tyr Tyr Gln Lys Ala Leu Glu
                965                 970                 975

Leu Asp Pro Asn Asn Ala Glu Ala Trp Tyr Asn Leu Gly Asn Ala Tyr
        980                 985                 990

Tyr Lys Gln Gly Asp Tyr Gln Lys Ala Ile Glu Tyr Tyr Gln Lys Ala
    995                 1000                1005

Leu Glu Leu Asp Pro Asn Asn Ala Glu Ala Trp Tyr Asn Leu Gly
```

```
                1010                1015                1020
Asn Ala Tyr Tyr Lys Gln Gly Asp Tyr Gln Lys Ala Ile Glu Asp
        1025                1030                1035

Tyr Gln Lys Ala Leu Glu Leu Asp Pro Asn Asn Gly Gly Gly Gly
1040                1045                1050

Ser Gly Gly Gly Gly Ser Gly Gly Gly Ser Gly Gly Asp Ile
1055                1060                1065

Val Leu Thr Gln Ser Pro Ala Ser Leu Ala Val Ser Leu Gly Gln
1070                1075                1080

Arg Ala Thr Ile Ser Cys Lys Ala Ser Gln Ser Val Asp Tyr Asp
1085                1090                1095

Gly Gly Ser Tyr Met Ser Trp Phe Gln Gln Arg Pro Gly Gln Pro
1100                1105                1110

Pro Lys Leu Leu Ile Ser Ala Ala Ser Asn Leu Glu Ser Gly Ile
1115                1120                1125

Pro Ala Arg Phe Ser Gly Ser Gly Ser Gly Thr Asp Phe Thr Leu
1130                1135                1140

Asn Ile His Pro Val Glu Glu Asp Val Ala Thr Tyr Tyr Cys
1145                1150                1155

Gln Gln Ser Tyr Glu Asp Pro Leu Thr Phe Gly Ala Gly Thr Lys
1160                1165                1170

Val Glu Ile Lys Arg Thr Val Ala Ala Pro Ser Val Phe Ile Phe
1175                1180                1185

Pro Pro Ser Asp Glu Gln Leu Lys Ser Gly Thr Ala Ser Val Val
1190                1195                1200

Cys Leu Leu Asn Asn Phe Tyr Pro Arg Glu Ala Lys Val Gln Trp
1205                1210                1215

Lys Val Asp Asn Ala Leu Gln Ser Gly Asn Ser Gln Glu Ser Val
1220                1225                1230

Thr Glu Gln Asp Ser Lys Asp Ser Thr Tyr Ser Leu Ser Ser Thr
1235                1240                1245

Leu Thr Leu Ser Lys Ala Asp Tyr Glu Lys His Lys Val Tyr Ala
1250                1255                1260

Cys Glu Val Thr His Gln Gly Leu Ser Ser Pro Val Thr Lys Ser
1265                1270                1275

Phe Asn Arg Gly Glu Cys Gly Gly Ser Ser Gly Ser Gly Ser Gly
1280                1285                1290

Ser Thr Gly Thr Ser Ser Ser Gly Thr Gly Thr Ser Ala Gly Thr
1295                1300                1305

Thr Gly Thr Ser Ala Ser Thr Ser Gly Ser Gly Ser Gly Gly Gly
1310                1315                1320

Gly Gly Ser Gly Gly Gly Gly Ser Ala Gly Gly Thr Ala Thr Ala
1325                1330                1335

Gly Ala Ser Ser Gly Ser Val Gln Leu Gln Gln Pro Gly Thr Glu
1340                1345                1350

Leu Val Lys Pro Gly Ala Ser Val Lys Leu Ser Cys Lys Ala Ser
1355                1360                1365

Gly Tyr Thr Phe Thr Ser Tyr Trp Ile His Trp Val Lys Gln Arg
1370                1375                1380

Pro Gly Gln Gly Leu Glu Trp Ile Gly Glu Ile Asn Pro Ser Ser
1385                1390                1395

Gly Arg Thr Asn Tyr Asn Glu Lys Phe Lys Asn Lys Val Thr Val
1400                1405                1410
```

-continued

```
Thr Val Asp Lys Ser Ser Thr Thr Ala Tyr Met Gln Leu Ser Asn
    1415                1420                1425

Leu Thr Ser Glu Asp Ser Ala Val Tyr Tyr Cys Ala Ser Arg Gly
    1430                1435                1440

Tyr Trp Gly Gln Gly Thr Thr Leu Thr Val Ser Ser Ala Ser Thr
    1445                1450                1455

Lys Gly Pro Ser Val Phe Pro Leu Ala Pro Ser Ser Lys Ser Thr
    1460                1465                1470

Ser Gly Gly Thr Ala Ala Leu Gly Cys Leu Val Lys Asp Tyr Phe
    1475                1480                1485

Pro Glu Pro Val Thr Val Ser Trp Asn Ser Gly Ala Leu Thr Ser
    1490                1495                1500

Gly Val His Thr Phe Pro Ala Val Leu Gln Ser Ser Gly Leu Tyr
    1505                1510                1515

Ser Leu Ser Ser Val Val Thr Val Pro Ser Ser Ser Leu Gly Thr
    1520                1525                1530

Gln Thr Tyr Ile Cys Asn Val Asn His Lys Pro Ser Asn Thr Lys
    1535                1540                1545

Val Asp Lys Lys Val Glu Pro Lys Ser Cys Asp Lys Thr His Thr
    1550                1555                1560

Thr Arg Gly Ala Ala Trp Ser His Pro Gln Phe Glu Lys Gly Ala
    1565                1570                1575

Ala Trp Ser His Pro Gln Phe Glu Lys Gly Ala Ala Trp Ser His
    1580                1585                1590

Pro Gln Phe Glu Lys Gly Ala Ala His His His His His His
    1595                1600                1605

<210> SEQ ID NO 26
<211> LENGTH: 1514
<212> TYPE: PRT
<213> ORGANISM: artificial
<220> FEATURE:
<223> OTHER INFORMATION: antibody-linker-decoyMET
      aa seq scMvDN30-linker L45-K842E

<400> SEQUENCE: 26

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
    50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
                100                 105                 110

Gln Gln Ser Tyr Glu Asp Pro Leu Thr Phe Gly Ala Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
```

```
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
                180                 185                 190
Lys Asp Ser Thr Tyr Ser Leu Ser Ser Thr Leu Thr Leu Ser Lys Ala
                195                 200                 205
Asp Tyr Glu Lys His Lys Val Tyr Ala Cys Glu Val Thr His Gln Gly
                210                 215                 220
Leu Ser Ser Pro Val Thr Lys Ser Phe Asn Arg Gly Glu Cys Gly Gly
225                 230                 235                 240
Ser Ser Gly Ser Gly Ser Gly Ser Thr Gly Thr Ser Ser Gly Thr
                245                 250                 255
Gly Thr Ser Ala Gly Thr Thr Gly Thr Ser Ala Ser Thr Ser Gly Ser
                260                 265                 270
Gly Ser Gly Gly Gly Gly Ser Gly Gly Gly Ser Ala Gly Gly
                275                 280                 285
Thr Ala Thr Ala Gly Ala Ser Ser Gly Ser Val Gln Leu Gln Gln Pro
290                 295                 300
Gly Thr Glu Leu Val Lys Pro Gly Ala Ser Val Lys Leu Ser Cys Lys
305                 310                 315                 320
Ala Ser Gly Tyr Thr Phe Thr Ser Tyr Trp Ile His Trp Val Lys Gln
                325                 330                 335
Arg Pro Gly Gln Gly Leu Glu Trp Ile Gly Glu Ile Asn Pro Ser Ser
                340                 345                 350
Gly Arg Thr Asn Tyr Asn Glu Lys Phe Lys Asn Lys Val Thr Val Thr
                355                 360                 365
Val Asp Lys Ser Ser Thr Thr Ala Tyr Met Gln Leu Ser Asn Leu Thr
                370                 375                 380
Ser Glu Asp Ser Ala Val Tyr Tyr Cys Ala Ser Arg Gly Tyr Trp Gly
385                 390                 395                 400
Gln Gly Thr Thr Leu Thr Val Ser Ser Ala Ser Thr Lys Gly Pro Ser
                405                 410                 415
Val Phe Pro Leu Ala Pro Ser Ser Lys Ser Thr Ser Gly Gly Thr Ala
                420                 425                 430
Ala Leu Gly Cys Leu Val Lys Asp Tyr Phe Pro Glu Pro Val Thr Val
                435                 440                 445
Ser Trp Asn Ser Gly Ala Leu Thr Ser Gly Val His Thr Phe Pro Ala
450                 455                 460
Val Leu Gln Ser Ser Gly Leu Tyr Ser Leu Ser Ser Val Val Thr Val
465                 470                 475                 480
Pro Ser Ser Ser Leu Gly Thr Gln Thr Tyr Ile Cys Asn Val Asn His
                485                 490                 495
Lys Pro Ser Asn Thr Lys Val Asp Lys Val Glu Pro Lys Ser Cys
                500                 505                 510
Asp Lys Thr His Thr Ala Glu Ala Ala Lys Glu Ala Ala Lys
                515                 520                 525
Glu Ala Ala Ala Lys Glu Ala Ala Ala Lys Ala Ala Glu Ala Ala
                530                 535                 540
Ala Lys Glu Ala Ala Ala Lys Glu Ala Ala Ala Lys Glu Ala Ala Ala
545                 550                 555                 560
Lys Ala Glu Cys Lys Glu Ala Leu Ala Lys Ser Glu Met Asn Val Asn
                565                 570                 575
```

-continued

```
Met Lys Tyr Gln Leu Pro Asn Phe Thr Ala Glu Thr Pro Ile Gln Asn
            580                 585                 590

Val Ile Leu His Glu His His Ile Phe Leu Gly Ala Thr Asn Tyr Ile
        595                 600                 605

Tyr Val Leu Asn Glu Glu Asp Leu Gln Lys Val Ala Glu Tyr Lys Thr
    610                 615                 620

Gly Pro Val Leu Glu His Pro Asp Cys Phe Pro Cys Gln Asp Cys Ser
625                 630                 635                 640

Ser Lys Ala Asn Leu Ser Gly Gly Val Trp Lys Asp Asn Ile Asn Met
                645                 650                 655

Ala Leu Val Val Asp Thr Tyr Tyr Asp Asp Gln Leu Ile Ser Cys Gly
            660                 665                 670

Ser Val Asn Arg Gly Thr Cys Gln Arg His Val Phe Pro His Asn His
        675                 680                 685

Thr Ala Asp Ile Gln Ser Glu Val His Cys Ile Phe Ser Pro Gln Ile
    690                 695                 700

Glu Glu Pro Ser Gln Cys Pro Asp Cys Val Val Ser Ala Leu Gly Ala
705                 710                 715                 720

Lys Val Leu Ser Ser Val Lys Asp Arg Phe Ile Asn Phe Phe Val Gly
                725                 730                 735

Asn Thr Ile Asn Ser Ser Tyr Phe Pro Asp His Pro Leu His Ser Ile
            740                 745                 750

Ser Val Arg Arg Leu Lys Glu Thr Lys Asp Gly Phe Met Phe Leu Thr
        755                 760                 765

Asp Gln Ser Tyr Ile Asp Val Leu Pro Glu Phe Arg Asp Ser Tyr Pro
    770                 775                 780

Ile Lys Tyr Val His Ala Phe Glu Ser Asn Asn Phe Ile Tyr Phe Leu
785                 790                 795                 800

Thr Val Gln Arg Glu Thr Leu Asp Ala Gln Thr Phe His Thr Arg Ile
                805                 810                 815

Ile Arg Phe Cys Ser Ile Asn Ser Gly Leu His Ser Tyr Met Glu Met
            820                 825                 830

Pro Leu Glu Cys Ile Leu Thr Glu Lys Arg Lys Lys Arg Ser Thr Lys
        835                 840                 845

Lys Glu Val Phe Asn Ile Leu Gln Ala Ala Tyr Val Ser Lys Pro Gly
    850                 855                 860

Ala Gln Leu Ala Arg Gln Ile Gly Ala Ser Leu Asn Asp Asp Ile Leu
865                 870                 875                 880

Phe Gly Val Phe Ala Gln Ser Lys Pro Asp Ser Ala Glu Pro Met Asp
                885                 890                 895

Arg Ser Ala Met Cys Ala Phe Pro Ile Lys Tyr Val Asn Asp Phe Phe
            900                 905                 910

Asn Lys Ile Val Asn Lys Asn Asn Val Arg Cys Leu Gln His Phe Tyr
        915                 920                 925

Gly Pro Asn His Glu His Cys Phe Asn Arg Thr Leu Leu Arg Asn Ser
    930                 935                 940

Ser Gly Cys Glu Ala Arg Arg Asp Glu Tyr Arg Thr Glu Phe Thr Thr
945                 950                 955                 960

Ala Leu Gln Arg Val Asp Leu Phe Met Gly Gln Phe Ser Glu Val Leu
                965                 970                 975

Leu Thr Ser Ile Ser Thr Phe Ile Lys Gly Asp Leu Thr Ile Ala Asn
            980                 985                 990
```

```
Leu Gly Thr Ser Glu Gly Arg Phe  Met Gln Val Val  Ser Arg Ser
         995                1000               1005

Gly Pro Ser Thr Pro His  Val Asn Phe Leu Leu Asp  Ser His Pro
    1010                1015                1020

Val Ser Pro Glu Val Ile  Val Glu His Thr Leu Asn  Gln Asn Gly
    1025                1030                1035

Tyr Thr Leu Val Ile Thr  Gly Lys Lys Ile Thr Lys  Ile Pro Leu
    1040                1045                1050

Asn Gly Leu Gly Cys Arg  His Phe Gln Ser Cys Ser  Gln Cys Leu
    1055                1060                1065

Ser Ala Pro Pro Phe Val  Gln Cys Gly Trp Cys His  Asp Lys Cys
    1070                1075                1080

Val Arg Ser Glu Glu Cys  Leu Ser Gly Thr Trp Thr  Gln Gln Ile
    1085                1090                1095

Cys Leu Pro Ala Ile Tyr  Lys Val Phe Pro Asn Ser  Ala Pro Leu
    1100                1105                1110

Glu Gly Gly Thr Arg Leu  Thr Ile Cys Gly Trp Asp  Phe Gly Phe
    1115                1120                1125

Arg Arg Asn Asn Lys Phe  Asp Leu Lys Lys Thr Arg  Val Leu Leu
    1130                1135                1140

Gly Asn Glu Ser Cys Thr  Leu Thr Leu Ser Glu Ser  Thr Met Asn
    1145                1150                1155

Thr Leu Lys Cys Thr Val  Gly Pro Ala Met Asn Lys  His Phe Asn
    1160                1165                1170

Met Ser Ile Ile Ile Ser  Asn Gly His Gly Thr Thr  Gln Tyr Ser
    1175                1180                1185

Thr Phe Ser Tyr Val Asp  Pro Val Ile Thr Ser Ile  Ser Pro Lys
    1190                1195                1200

Tyr Gly Pro Met Ala Gly  Gly Thr Leu Leu Thr Leu  Thr Gly Asn
    1205                1210                1215

Tyr Leu Asn Ser Gly Asn  Ser Arg His Ile Ser Ile  Gly Gly Lys
    1220                1225                1230

Thr Cys Thr Leu Lys Ser  Val Ser Asn Ser Ile Leu  Glu Cys Tyr
    1235                1240                1245

Thr Pro Ala Gln Thr Ile  Ser Thr Glu Phe Ala Val  Lys Leu Lys
    1250                1255                1260

Ile Asp Leu Ala Asn Arg  Glu Thr Ser Ile Phe Ser  Tyr Arg Glu
    1265                1270                1275

Asp Pro Ile Val Tyr Glu  Ile His Pro Thr Lys Ser  Phe Ile Ser
    1280                1285                1290

Gly Gly Ser Thr Ile Thr  Gly Val Gly Lys Asn Leu  Asn Ser Val
    1295                1300                1305

Ser Val Pro Arg Met Val  Ile Asn Val His Glu Ala  Gly Arg Asn
    1310                1315                1320

Phe Thr Val Ala Cys Gln  His Arg Ser Asn Ser Glu  Ile Ile Cys
    1325                1330                1335

Cys Thr Thr Pro Ser Leu  Gln Gln Leu Asn Leu Gln  Leu Pro Leu
    1340                1345                1350

Lys Thr Lys Ala Phe Phe  Met Leu Asp Gly Ile Leu  Ser Lys Tyr
    1355                1360                1365

Phe Asp Leu Ile Tyr Val  His Asn Pro Val Phe Glu  Pro Phe Glu
    1370                1375                1380

Lys Pro Val Met Ile Ser  Met Gly Asn Glu Asn Val  Leu Glu Ile
```

```
                    1385                1390                1395

Lys Gly  Asn Asp Ile Asp Pro  Glu Ala Val Lys Gly  Glu Val Leu
        1400                1405                1410

Lys Val  Gly Asn Lys Ser Cys  Glu Asn Ile His Leu  His Ser Glu
        1415                1420                1425

Ala Val  Leu Cys Thr Val Pro  Asn Asp Leu Leu Lys  Leu Asn Ser
        1430                1435                1440

Glu Leu  Asn Ile Glu Trp Lys  Gln Ala Ile Ser Ser  Thr Val Leu
        1445                1450                1455

Gly Lys  Val Ile Val Gln Pro  Asp Gln Asn Phe Thr  Ala Ser Gly
        1460                1465                1470

Ala Ala  Trp Ser His Pro Gln  Phe Glu Lys Gly Ala  Ala Trp Ser
        1475                1480                1485

His Pro  Gln Phe Glu Lys Gly  Ala Ala Trp Ser His  Pro Gln Phe
        1490                1495                1500

Glu Lys  Gly Ala Ala His His  His His His
        1505                1510

<210> SEQ ID NO 27
<211> LENGTH: 1529
<212> TYPE: PRT
<213> ORGANISM: artificial
<220> FEATURE:
<223> OTHER INFORMATION: antibody-linker-decoyMET
      aa seq scMvDN30-linker L60-K842E

<400> SEQUENCE: 27

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
    50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

```
Leu Ser Ser Pro Val Thr Lys Ser Phe Asn Arg Gly Glu Cys Gly Gly
225                 230                 235                 240

Ser Ser Gly Ser Gly Ser Gly Ser Thr Gly Thr Ser Ser Ser Gly Thr
            245                 250                 255

Gly Thr Ser Ala Gly Thr Thr Gly Thr Ser Ala Ser Thr Ser Gly Ser
            260                 265                 270

Gly Ser Gly Gly Gly Gly Ser Gly Gly Gly Ser Ala Gly Gly
        275                 280                 285

Thr Ala Thr Ala Gly Ala Ser Ser Gly Ser Val Gln Leu Gln Gln Pro
        290                 295                 300

Gly Thr Glu Leu Val Lys Pro Gly Ala Ser Val Lys Leu Ser Cys Lys
305                 310                 315                 320

Ala Ser Gly Tyr Thr Phe Thr Ser Tyr Trp Ile His Trp Val Lys Gln
                325                 330                 335

Arg Pro Gly Gln Gly Leu Glu Trp Ile Gly Glu Ile Asn Pro Ser Ser
                340                 345                 350

Gly Arg Thr Asn Tyr Asn Glu Lys Phe Lys Asn Lys Val Thr Val Thr
                355                 360                 365

Val Asp Lys Ser Ser Thr Thr Ala Tyr Met Gln Leu Ser Asn Leu Thr
370                 375                 380

Ser Glu Asp Ser Ala Val Tyr Tyr Cys Ala Ser Arg Gly Tyr Trp Gly
385                 390                 395                 400

Gln Gly Thr Thr Leu Thr Val Ser Ser Ala Ser Thr Lys Gly Pro Ser
                405                 410                 415

Val Phe Pro Leu Ala Pro Ser Ser Lys Ser Thr Ser Gly Gly Thr Ala
                420                 425                 430

Ala Leu Gly Cys Leu Val Lys Asp Tyr Phe Pro Glu Pro Val Thr Val
            435                 440                 445

Ser Trp Asn Ser Gly Ala Leu Thr Ser Gly Val His Thr Phe Pro Ala
            450                 455                 460

Val Leu Gln Ser Ser Gly Leu Tyr Ser Leu Ser Ser Val Val Thr Val
465                 470                 475                 480

Pro Ser Ser Ser Leu Gly Thr Gln Thr Tyr Ile Cys Asn Val Asn His
                485                 490                 495

Lys Pro Ser Asn Thr Lys Val Asp Lys Lys Val Glu Pro Lys Ser Cys
                500                 505                 510

Asp Lys Thr His Thr Gly Gly Ser Gly Ser Gly Ser Gly Ser Gly Thr
            515                 520                 525

Gly Thr Ser Ser Ser Gly Thr Gly Thr Ser Ala Gly Thr Thr Gly Thr
        530                 535                 540

Ser Ala Ser Thr Ser Gly Ser Gly Ser Gly Gly Gly Gly Ser Gly Gly
545                 550                 555                 560

Gly Gly Gly Ser Ala Gly Gly Thr Ala Thr Ala Gly Ala Ser Ser Gly
            565                 570                 575

Ser Glu Cys Lys Glu Ala Leu Ala Lys Ser Glu Met Asn Val Asn Met
                580                 585                 590

Lys Tyr Gln Leu Pro Asn Phe Thr Ala Glu Thr Pro Ile Gln Asn Val
            595                 600                 605

Ile Leu His Glu His His Ile Phe Leu Gly Ala Thr Asn Tyr Ile Tyr
            610                 615                 620

Val Leu Asn Glu Glu Asp Leu Gln Lys Val Ala Glu Tyr Lys Thr Gly
625                 630                 635                 640

Pro Val Leu Glu His Pro Asp Cys Phe Pro Cys Gln Asp Cys Ser Ser
```

```
                645               650                655
Lys Ala Asn Leu Ser Gly Gly Val Trp Lys Asp Asn Ile Asn Met Ala
                660                665                670
Leu Val Val Asp Thr Tyr Tyr Asp Asp Gln Leu Ile Ser Cys Gly Ser
                675                680                685
Val Asn Arg Gly Thr Cys Gln Arg His Val Phe Pro His Asn His Thr
                690                695                700
Ala Asp Ile Gln Ser Glu Val His Cys Ile Phe Ser Pro Gln Ile Glu
705                710                715                720
Glu Pro Ser Gln Cys Pro Asp Cys Val Val Ser Ala Leu Gly Ala Lys
                725                730                735
Val Leu Ser Ser Val Lys Asp Arg Phe Ile Asn Phe Phe Val Gly Asn
                740                745                750
Thr Ile Asn Ser Ser Tyr Phe Pro Asp His Pro Leu His Ser Ile Ser
                755                760                765
Val Arg Arg Leu Lys Glu Thr Lys Asp Gly Phe Met Phe Leu Thr Asp
                770                775                780
Gln Ser Tyr Ile Asp Val Leu Pro Glu Phe Arg Asp Ser Tyr Pro Ile
785                790                795                800
Lys Tyr Val His Ala Phe Glu Ser Asn Asn Phe Ile Tyr Phe Leu Thr
                805                810                815
Val Gln Arg Glu Thr Leu Asp Ala Gln Thr Phe His Thr Arg Ile Ile
                820                825                830
Arg Phe Cys Ser Ile Asn Ser Gly Leu His Ser Tyr Met Glu Met Pro
                835                840                845
Leu Glu Cys Ile Leu Thr Glu Lys Arg Lys Lys Arg Ser Thr Lys Lys
                850                855                860
Glu Val Phe Asn Ile Leu Gln Ala Ala Tyr Val Ser Lys Pro Gly Ala
865                870                875                880
Gln Leu Ala Arg Gln Ile Gly Ala Ser Leu Asn Asp Asp Ile Leu Phe
                885                890                895
Gly Val Phe Ala Gln Ser Lys Pro Asp Ser Ala Glu Pro Met Asp Arg
                900                905                910
Ser Ala Met Cys Ala Phe Pro Ile Lys Tyr Val Asn Asp Phe Phe Asn
                915                920                925
Lys Ile Val Asn Lys Asn Val Arg Cys Leu Gln His Phe Tyr Gly
                930                935                940
Pro Asn His Glu His Cys Phe Asn Arg Thr Leu Leu Arg Asn Ser Ser
945                950                955                960
Gly Cys Glu Ala Arg Arg Asp Glu Tyr Arg Thr Glu Phe Thr Thr Ala
                965                970                975
Leu Gln Arg Val Asp Leu Phe Met Gly Gln Phe Ser Glu Val Leu Leu
                980                985                990
Thr Ser Ile Ser Thr Phe Ile Lys Gly Asp Leu Thr Ile Ala Asn Leu
                995                1000               1005
Gly Thr Ser Glu Gly Arg Phe Met Gln Val Val Ser Arg Ser
                1010               1015               1020
Gly Pro Ser Thr Pro His Val Asn Phe Leu Leu Asp Ser His Pro
                1025               1030               1035
Val Ser Pro Glu Val Ile Val Glu His Thr Leu Asn Gln Asn Gly
                1040               1045               1050
Tyr Thr Leu Val Ile Thr Gly Lys Lys Ile Thr Lys Ile Pro Leu
                1055               1060               1065
```

-continued

```
Asn Gly Leu Gly Cys Arg His Phe Gln Ser Cys Ser Gln Cys Leu
    1070                1075            1080

Ser Ala Pro Pro Phe Val Gln Cys Gly Trp Cys His Asp Lys Cys
    1085                1090            1095

Val Arg Ser Glu Glu Cys Leu Ser Gly Thr Trp Thr Gln Gln Ile
    1100                1105            1110

Cys Leu Pro Ala Ile Tyr Lys Val Phe Pro Asn Ser Ala Pro Leu
    1115                1120            1125

Glu Gly Gly Thr Arg Leu Thr Ile Cys Gly Trp Asp Phe Gly Phe
    1130                1135            1140

Arg Arg Asn Asn Lys Phe Asp Leu Lys Lys Thr Arg Val Leu Leu
    1145                1150            1155

Gly Asn Glu Ser Cys Thr Leu Thr Leu Ser Glu Ser Thr Met Asn
    1160                1165            1170

Thr Leu Lys Cys Thr Val Gly Pro Ala Met Asn Lys His Phe Asn
    1175                1180            1185

Met Ser Ile Ile Ile Ser Asn Gly His Gly Thr Thr Gln Tyr Ser
    1190                1195            1200

Thr Phe Ser Tyr Val Asp Pro Val Ile Thr Ser Ile Ser Pro Lys
    1205                1210            1215

Tyr Gly Pro Met Ala Gly Gly Thr Leu Leu Thr Leu Thr Gly Asn
    1220                1225            1230

Tyr Leu Asn Ser Gly Asn Ser Arg His Ile Ser Ile Gly Gly Lys
    1235                1240            1245

Thr Cys Thr Leu Lys Ser Val Ser Asn Ser Ile Leu Glu Cys Tyr
    1250                1255            1260

Thr Pro Ala Gln Thr Ile Ser Thr Glu Phe Ala Val Lys Leu Lys
    1265                1270            1275

Ile Asp Leu Ala Asn Arg Glu Thr Ser Ile Phe Ser Tyr Arg Glu
    1280                1285            1290

Asp Pro Ile Val Tyr Glu Ile His Pro Thr Lys Ser Phe Ile Ser
    1295                1300            1305

Gly Gly Ser Thr Ile Thr Gly Val Gly Lys Asn Leu Asn Ser Val
    1310                1315            1320

Ser Val Pro Arg Met Val Ile Asn Val His Glu Ala Gly Arg Asn
    1325                1330            1335

Phe Thr Val Ala Cys Gln His Arg Ser Asn Ser Glu Ile Ile Cys
    1340                1345            1350

Cys Thr Thr Pro Ser Leu Gln Gln Leu Asn Leu Gln Leu Pro Leu
    1355                1360            1365

Lys Thr Lys Ala Phe Phe Met Leu Asp Gly Ile Leu Ser Lys Tyr
    1370                1375            1380

Phe Asp Leu Ile Tyr Val His Asn Pro Val Phe Glu Pro Phe Glu
    1385                1390            1395

Lys Pro Val Met Ile Ser Met Gly Asn Glu Asn Val Leu Glu Ile
    1400                1405            1410

Lys Gly Asn Asp Ile Asp Pro Glu Ala Val Lys Gly Glu Val Leu
    1415                1420            1425

Lys Val Gly Asn Lys Ser Cys Glu Asn Ile His Leu His Ser Glu
    1430                1435            1440

Ala Val Leu Cys Thr Val Pro Asn Asp Leu Leu Lys Leu Asn Ser
    1445                1450            1455
```

-continued

```
Glu Leu Asn Ile Glu Trp Lys Gln Ala Ile Ser Ser Thr Val Leu
    1460                1465                1470

Gly Lys Val Ile Val Gln Pro Asp Gln Asn Phe Thr Ala Ser Gly
    1475                1480                1485

Ala Ala Trp Ser His Pro Gln Phe Glu Lys Gly Ala Ala Trp Ser
    1490                1495                1500

His Pro Gln Phe Glu Lys Gly Ala Ala Trp Ser His Pro Gln Phe
    1505                1510                1515

Glu Lys Gly Ala Ala His His His His His His
    1520                1525

<210> SEQ ID NO 28
<211> LENGTH: 1603
<212> TYPE: PRT
<213> ORGANISM: artificial
<220> FEATURE:
<223> OTHER INFORMATION: antibody-linker-decoyMET
      aa seq scMvDN30-linker L134-K842E

<400> SEQUENCE: 28

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
            35                  40                  45

Val Asp Tyr Asp Gly Ser Tyr Met Ser Trp Phe Gln Gln Arg Pro
    50                  55                  60

Gly Gln Pro Pro Lys Leu Leu Ile Ser Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Val Ala Thr Tyr Tyr Cys
            100                 105                 110

Gln Gln Ser Tyr Glu Asp Pro Leu Thr Phe Gly Ala Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Gly Gly
225                 230                 235                 240

Ser Ser Gly Ser Gly Ser Gly Thr Gly Thr Ser Ser Gly Thr
                245                 250                 255

Gly Thr Ser Ala Gly Thr Thr Gly Thr Ser Ala Ser Thr Ser Gly Ser
            260                 265                 270

Gly Ser Gly Gly Gly Gly Ser Gly Gly Gly Ser Ala Gly Gly
        275                 280                 285
```

```
Thr Ala Thr Ala Gly Ala Ser Ser Gly Ser Val Gln Leu Gln Gln Pro
    290                 295                 300
Gly Thr Glu Leu Val Lys Pro Gly Ala Ser Val Lys Leu Ser Cys Lys
305                 310                 315                 320
Ala Ser Gly Tyr Thr Phe Thr Ser Tyr Trp Ile His Trp Val Lys Gln
                325                 330                 335
Arg Pro Gly Gln Gly Leu Glu Trp Ile Gly Glu Ile Asn Pro Ser Ser
            340                 345                 350
Gly Arg Thr Asn Tyr Asn Glu Lys Phe Lys Asn Lys Val Thr Val Thr
        355                 360                 365
Val Asp Lys Ser Ser Thr Thr Ala Tyr Met Gln Leu Ser Asn Leu Thr
    370                 375                 380
Ser Glu Asp Ser Ala Val Tyr Tyr Cys Ala Ser Arg Gly Tyr Trp Gly
385                 390                 395                 400
Gln Gly Thr Thr Leu Thr Val Ser Ser Ala Ser Thr Lys Gly Pro Ser
                405                 410                 415
Val Phe Pro Leu Ala Pro Ser Ser Lys Ser Thr Ser Gly Gly Thr Ala
            420                 425                 430
Ala Leu Gly Cys Leu Val Lys Asp Tyr Phe Pro Glu Pro Val Thr Val
        435                 440                 445
Ser Trp Asn Ser Gly Ala Leu Thr Ser Gly Val His Thr Phe Pro Ala
    450                 455                 460
Val Leu Gln Ser Ser Gly Leu Tyr Ser Leu Ser Ser Val Val Thr Val
465                 470                 475                 480
Pro Ser Ser Ser Leu Gly Thr Gln Thr Tyr Ile Cys Asn Val Asn His
                485                 490                 495
Lys Pro Ser Asn Thr Lys Val Asp Lys Lys Val Glu Pro Lys Ser Cys
            500                 505                 510
Asp Lys Thr His Thr Gly Gly Gly Ser Gly Gly Gly Gly Ser Gly
        515                 520                 525
Gly Gly Gly Ser Ala Glu Ala Trp Tyr Asn Leu Gly Asn Ala Tyr Tyr
    530                 535                 540
Lys Gln Gly Asp Tyr Gln Lys Ala Ile Glu Tyr Tyr Gln Lys Ala Leu
545                 550                 555                 560
Glu Leu Asp Pro Asn Asn Ala Glu Ala Trp Tyr Asn Leu Gly Asn Ala
                565                 570                 575
Tyr Tyr Lys Gln Gly Asp Tyr Gln Lys Ala Ile Glu Tyr Tyr Gln Lys
            580                 585                 590
Ala Leu Glu Leu Asp Pro Asn Asn Ala Glu Ala Trp Tyr Asn Leu Gly
        595                 600                 605
Asn Ala Tyr Tyr Lys Gln Gly Asp Tyr Gln Lys Ala Ile Glu Asp Tyr
    610                 615                 620
Gln Lys Ala Leu Glu Leu Asp Pro Asn Asn Gly Gly Gly Ser Gly
625                 630                 635                 640
Gly Gly Gly Ser Gly Gly Gly Ser Gly Gly Glu Cys Lys Glu Ala
                645                 650                 655
Leu Ala Lys Ser Glu Met Asn Val Asn Met Lys Tyr Gln Leu Pro Asn
            660                 665                 670
Phe Thr Ala Glu Thr Pro Ile Gln Asn Val Ile Leu His Glu His His
        675                 680                 685
Ile Phe Leu Gly Ala Thr Asn Tyr Ile Tyr Val Leu Asn Glu Glu Asp
    690                 695                 700
```

```
Leu Gln Lys Val Ala Glu Tyr Lys Thr Gly Pro Val Leu Glu His Pro
705                 710                 715                 720

Asp Cys Phe Pro Cys Gln Asp Cys Ser Ser Lys Ala Asn Leu Ser Gly
            725                 730                 735

Gly Val Trp Lys Asp Asn Ile Asn Met Ala Leu Val Val Asp Thr Tyr
        740                 745                 750

Tyr Asp Asp Gln Leu Ile Ser Cys Gly Ser Val Asn Arg Gly Thr Cys
        755                 760                 765

Gln Arg His Val Phe Pro His Asn His Thr Ala Asp Ile Gln Ser Glu
    770                 775                 780

Val His Cys Ile Phe Ser Pro Gln Ile Glu Glu Pro Ser Gln Cys Pro
785                 790                 795                 800

Asp Cys Val Val Ser Ala Leu Gly Ala Lys Val Leu Ser Ser Val Lys
            805                 810                 815

Asp Arg Phe Ile Asn Phe Phe Val Gly Asn Thr Ile Asn Ser Ser Tyr
            820                 825                 830

Phe Pro Asp His Pro Leu His Ser Ile Ser Val Arg Arg Leu Lys Glu
            835                 840                 845

Thr Lys Asp Gly Phe Met Phe Leu Thr Asp Gln Ser Tyr Ile Asp Val
    850                 855                 860

Leu Pro Glu Phe Arg Asp Ser Tyr Pro Ile Lys Tyr Val His Ala Phe
865                 870                 875                 880

Glu Ser Asn Asn Phe Ile Tyr Phe Leu Thr Val Gln Arg Glu Thr Leu
                885                 890                 895

Asp Ala Gln Thr Phe His Thr Arg Ile Ile Arg Phe Cys Ser Ile Asn
            900                 905                 910

Ser Gly Leu His Ser Tyr Met Glu Met Pro Leu Glu Cys Ile Leu Thr
        915                 920                 925

Glu Lys Arg Lys Lys Arg Ser Thr Lys Lys Glu Val Phe Asn Ile Leu
    930                 935                 940

Gln Ala Ala Tyr Val Ser Lys Pro Gly Ala Gln Leu Ala Arg Gln Ile
945                 950                 955                 960

Gly Ala Ser Leu Asn Asp Asp Ile Leu Phe Gly Val Phe Ala Gln Ser
            965                 970                 975

Lys Pro Asp Ser Ala Glu Pro Met Asp Arg Ser Ala Met Cys Ala Phe
            980                 985                 990

Pro Ile Lys Tyr Val Asn Asp Phe Phe Asn Lys Ile Val Asn Lys Asn
            995                1000                1005

Asn Val Arg Cys Leu Gln His Phe Tyr Gly Pro Asn His Glu His
    1010                1015                1020

Cys Phe Asn Arg Thr Leu Leu Arg Asn Ser Ser Gly Cys Glu Ala
    1025                1030                1035

Arg Arg Asp Glu Tyr Arg Thr Glu Phe Thr Thr Ala Leu Gln Arg
    1040                1045                1050

Val Asp Leu Phe Met Gly Gln Phe Ser Glu Val Leu Leu Thr Ser
    1055                1060                1065

Ile Ser Thr Phe Ile Lys Gly Asp Leu Thr Ile Ala Asn Leu Gly
    1070                1075                1080

Thr Ser Glu Gly Arg Phe Met Gln Val Val Val Ser Arg Ser Gly
    1085                1090                1095

Pro Ser Thr Pro His Val Asn Phe Leu Leu Asp Ser His Pro Val
    1100                1105                1110

Ser Pro Glu Val Ile Val Glu His Thr Leu Asn Gln Asn Gly Tyr
```

|     |     |     |     |     |     |     |     |     |     |
|-----|-----|-----|-----|-----|-----|-----|-----|-----|-----|
|     |     | 1115 |     |     | 1120 |     |     | 1125 |     |
| Thr | Leu | Val | Ile | Thr | Gly | Lys | Lys | Ile | Thr | Lys | Ile | Pro | Leu | Asn |
|     |     | 1130 |     |     |     | 1135 |     |     |     | 1140 |
| Gly | Leu | Gly | Cys | Arg | His | Phe | Gln | Ser | Cys | Ser | Gln | Cys | Leu | Ser |
|     |     | 1145 |     |     |     | 1150 |     |     |     | 1155 |
| Ala | Pro | Pro | Phe | Val | Gln | Cys | Gly | Trp | Cys | His | Asp | Lys | Cys | Val |
|     |     | 1160 |     |     |     | 1165 |     |     |     | 1170 |
| Arg | Ser | Glu | Glu | Cys | Leu | Ser | Gly | Thr | Trp | Thr | Gln | Gln | Ile | Cys |
|     |     | 1175 |     |     |     | 1180 |     |     |     | 1185 |
| Leu | Pro | Ala | Ile | Tyr | Lys | Val | Phe | Pro | Asn | Ser | Ala | Pro | Leu | Glu |
|     |     | 1190 |     |     |     | 1195 |     |     |     | 1200 |
| Gly | Gly | Thr | Arg | Leu | Thr | Ile | Cys | Gly | Trp | Asp | Phe | Gly | Phe | Arg |
|     |     | 1205 |     |     |     | 1210 |     |     |     | 1215 |
| Arg | Asn | Asn | Lys | Phe | Asp | Leu | Lys | Lys | Thr | Arg | Val | Leu | Leu | Gly |
|     |     | 1220 |     |     |     | 1225 |     |     |     | 1230 |
| Asn | Glu | Ser | Cys | Thr | Leu | Thr | Leu | Ser | Glu | Ser | Thr | Met | Asn | Thr |
|     |     | 1235 |     |     |     | 1240 |     |     |     | 1245 |
| Leu | Lys | Cys | Thr | Val | Gly | Pro | Ala | Met | Asn | Lys | His | Phe | Asn | Met |
|     |     | 1250 |     |     |     | 1255 |     |     |     | 1260 |
| Ser | Ile | Ile | Ile | Ser | Asn | Gly | His | Gly | Thr | Thr | Gln | Tyr | Ser | Thr |
|     |     | 1265 |     |     |     | 1270 |     |     |     | 1275 |
| Phe | Ser | Tyr | Val | Asp | Pro | Val | Ile | Thr | Ser | Ile | Ser | Pro | Lys | Tyr |
|     |     | 1280 |     |     |     | 1285 |     |     |     | 1290 |
| Gly | Pro | Met | Ala | Gly | Gly | Thr | Leu | Leu | Thr | Leu | Thr | Gly | Asn | Tyr |
|     |     | 1295 |     |     |     | 1300 |     |     |     | 1305 |
| Leu | Asn | Ser | Gly | Asn | Ser | Arg | His | Ile | Ser | Ile | Gly | Gly | Lys | Thr |
|     |     | 1310 |     |     |     | 1315 |     |     |     | 1320 |
| Cys | Thr | Leu | Lys | Ser | Val | Ser | Asn | Ser | Ile | Leu | Glu | Cys | Tyr | Thr |
|     |     | 1325 |     |     |     | 1330 |     |     |     | 1335 |
| Pro | Ala | Gln | Thr | Ile | Ser | Thr | Glu | Phe | Ala | Val | Lys | Leu | Lys | Ile |
|     |     | 1340 |     |     |     | 1345 |     |     |     | 1350 |
| Asp | Leu | Ala | Asn | Arg | Glu | Thr | Ser | Ile | Phe | Ser | Tyr | Arg | Glu | Asp |
|     |     | 1355 |     |     |     | 1360 |     |     |     | 1365 |
| Pro | Ile | Val | Tyr | Glu | Ile | His | Pro | Thr | Lys | Ser | Phe | Ile | Ser | Gly |
|     |     | 1370 |     |     |     | 1375 |     |     |     | 1380 |
| Gly | Ser | Thr | Ile | Thr | Gly | Val | Gly | Lys | Asn | Leu | Asn | Ser | Val | Ser |
|     |     | 1385 |     |     |     | 1390 |     |     |     | 1395 |
| Val | Pro | Arg | Met | Val | Ile | Asn | Val | His | Glu | Ala | Gly | Arg | Asn | Phe |
|     |     | 1400 |     |     |     | 1405 |     |     |     | 1410 |
| Thr | Val | Ala | Cys | Gln | His | Arg | Ser | Asn | Ser | Glu | Ile | Ile | Cys | Cys |
|     |     | 1415 |     |     |     | 1420 |     |     |     | 1425 |
| Thr | Thr | Pro | Ser | Leu | Gln | Gln | Leu | Asn | Leu | Gln | Leu | Pro | Leu | Lys |
|     |     | 1430 |     |     |     | 1435 |     |     |     | 1440 |
| Thr | Lys | Ala | Phe | Phe | Met | Leu | Asp | Gly | Ile | Leu | Ser | Lys | Tyr | Phe |
|     |     | 1445 |     |     |     | 1450 |     |     |     | 1455 |
| Asp | Leu | Ile | Tyr | Val | His | Asn | Pro | Val | Phe | Glu | Pro | Phe | Glu | Lys |
|     |     | 1460 |     |     |     | 1465 |     |     |     | 1470 |
| Pro | Val | Met | Ile | Ser | Met | Gly | Asn | Glu | Asn | Val | Leu | Glu | Ile | Lys |
|     |     | 1475 |     |     |     | 1480 |     |     |     | 1485 |
| Gly | Asn | Asp | Ile | Asp | Pro | Glu | Ala | Val | Lys | Gly | Glu | Val | Leu | Lys |
|     |     | 1490 |     |     |     | 1495 |     |     |     | 1500 |
| Val | Gly | Asn | Lys | Ser | Cys | Glu | Asn | Ile | His | Leu | His | Ser | Glu | Ala |
|     |     | 1505 |     |     |     | 1510 |     |     |     | 1515 |

| Val | Leu | Cys | Thr | Val | Pro | Asn | Asp | Leu | Leu | Lys | Leu | Asn | Ser | Glu |
| | | 1520 | | | | 1525 | | | | 1530 | | | | |

| Leu | Asn | Ile | Glu | Trp | Lys | Gln | Ala | Ile | Ser | Ser | Thr | Val | Leu | Gly |
| 1535 | | | | | 1540 | | | | | 1545 | | | | |

| Lys | Val | Ile | Val | Gln | Pro | Asp | Gln | Asn | Phe | Thr | Ala | Ser | Gly | Ala |
| 1550 | | | | | 1555 | | | | | 1560 | | | | |

| Ala | Trp | Ser | His | Pro | Gln | Phe | Glu | Lys | Gly | Ala | Ala | Trp | Ser | His |
| 1565 | | | | | 1570 | | | | | 1575 | | | | |

| Pro | Gln | Phe | Glu | Lys | Gly | Ala | Ala | Trp | Ser | His | Pro | Gln | Phe | Glu |
| 1580 | | | | | 1585 | | | | | 1590 | | | | |

| Lys | Gly | Ala | Ala | His | His | His | His | His | His |
| 1595 | | | | | 1600 | | | | |

<210> SEQ ID NO 29
<211> LENGTH: 4557
<212> TYPE: DNA
<213> ORGANISM: artificial
<220> FEATURE:
<223> OTHER INFORMATION: decoyMET-linker-antibody
      nucleotide seq K842E-linker L45-scMvDN30

<400> SEQUENCE: 29

```
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc caacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg aacacccag attgtttccc atgtcaggac    300
tgcagcagca agccaattt tcaggaggt gtttggaaag ataacatcaa catggctcta    360
gttgtggaca cctactatga tgatcaactc attagctgtg gcagcgtcaa cagagggacc    420
tgccagcgac atgtcttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag aataatcagg    840
ttctgttcca taaactctgg attgcattcc tacatggaaa tgcctctgga gtgtattctc    900
acagaaaaga gaaaaaagag atccacaaag aaggaagtgt taatatact tcaggctgcg    960
tatgtcagca agcctggggc ccagcttgct agacaaatag agccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttttac ggacccaatc atgagcactg ctttaatagg   1200
acacttctga gaaattcatc aggctgtgaa gcgcgccgtg atgaatatcg aacagagttt   1260
accacagctt gcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
```

```
tacacactgg ttatcactgg gaagaagatc acgaagatcc cattgaatgg cttgggttgc    1560
agacatttcc agtcttgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata ataaatttga tttaaagaaa    1800
actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtcgatcc tgtaataaca    1980
agtatttcgc cgaaatacgg tcctatggct ggtggcactt tacttacttt aactggaaat    2040
tacctaaaca gtgggaactc tagacacatt tcaattggtg aaaaacatg tactttaaaa     2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatcttta ttagtggtgg gagcacaata     2280
acaggtgttg ggaaaaacct gaactcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atggcatcct ttccaaatac tttgatctca tttatgtaca taatcctgtg    2520
tttgagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacagctg aagctgcagc caaagaagct    2820
gcagccaaag aggccgcagc taaggaagcc gcagcaaaag ctgctgctga agctgcagcc    2880
aaagaagctg cagccaaaga ggccgcagct aaggaagccg cagcaaaagc tgacattgtg    2940
ctgacccaat ctccagcttc tttggctgtg tctctagggc agagggccac catctcctgc    3000
aaggccagcc aaagtgttga ttatgatggt ggtagttata tgagttggtt ccaacagaga    3060
ccaggacagc cacccaaact cctcatctct gctgcatcca accttgaatc tggcatccca    3120
gccaggttta gtggcagtgg ctctgggaca gacttcaccc tcaatatcca tcctgtggag    3180
gaggaggatg ttgcaaccta ttactgtcag caaagttatg aagacccgct cacgttcggt    3240
gctggtacca aggtggagat caaacgaact gtggctgcac catctgtctt catcttcccg    3300
ccatctgatg agcagttgaa atctggaact gcctctgttg tgtgcctgct gaataacttc    3360
tatcccagag aggccaaagt acagtggaag gtggataacg ccctccaatc gggtaactcc    3420
caggagagtg tcacagagca ggacagcaag gacagcacct acagcctcag cagcaccctg    3480
acgctgagca agcagactac gagaaacac aaagtctacg cctgcgaagt cacccatcag     3540
ggcctgagct cgcccgtcac aaagagcttc aacaggggag agtgtggtgg ttcttcgggt    3600
tcaggctcgg gctccacagg tacatcgtca tcgggtacag gtacttcagc tggcacaacg    3660
ggtacctccg catctacttc cggttcaggc tccggaggcg gcggcggctc gggtggtggt    3720
ggatctgccg gcgaaccgc aaccgcaggc gcttcttctg gttccgtcca actgcagcag    3780
cctgggactg aactggtgaa gcctgggggct tcagtgaagc tgtcctgcaa ggcttctggc    3840
```

| | |
|---|---|
| tacaccttca ccagttactg gatacactgg gtgaagcaga ggcctggaca aggccttgag | 3900 |
| tggattggag agattaatcc tagcagcggt cgtactaact acaacgagaa attcaagaac | 3960 |
| aaggtcacag tgactgtaga caaatcttcc accacagcct acatgcaact cagcaacctg | 4020 |
| acatctgagg actctgcggt ctattactgt gcaagtaggg gctactgggg ccaaggcacc | 4080 |
| actctcacag tctcctcagc tagcacgaag ggcccatcgg tcttcccct ggcaccctcc | 4140 |
| tccaagagca cctctggggg cacagcggcc ctgggctgcc tggtcaagga ctacttcccc | 4200 |
| gaacccgtga cggtgtcgtg aactcaggc gccctgacca gcggcgtgca ccttcccg | 4260 |
| gctgtcctac agtcctcagg actctactcc ctcagcagcg tggtgaccgt gcctccagc | 4320 |
| agcttgggca cccagaccta catctgcaac gtgaatcaca agcccagcaa caccaaggtg | 4380 |
| gacaagaaag ttgagcccaa atcttgtgac aaaactcaca acgcgtgg tgccgcatgg | 4440 |
| agccaccccc agttcgaaaa aggggccgca tggagccacc cccagttcga aaaggggcc | 4500 |
| gcatggagcc accccagtt cgaaaaaggg gccgcacacc atcaccatca ccattag | 4557 |

```
<210> SEQ ID NO 30
<211> LENGTH: 4602
<212> TYPE: DNA
<213> ORGANISM: artificial
<220> FEATURE:
<223> OTHER INFORMATION: decoyMET-linker-antibody
      nucleotide seq K842E-linker L60-scMvDN30

<400> SEQUENCE: 30
```

| | |
|---|---|
| atgaaggccc ccgctgtgct tgcacctggc atcctcgtgc tcctgtttac cttggtgcag | 60 |
| aggagcaatg gggagtgtaa agaggcacta gcaaagtccg agatgaatgt gaatatgaag | 120 |
| tatcagcttc ccaacttcac cgcggaaaca cccatccaga atgtcattct acatgagcat | 180 |
| cacattttcc ttggtgccac taactacatt tatgttttaa atgaggaaga ccttcagaag | 240 |
| gttgctgagt acaagactgg gcctgtgctg aacacccag attgtttccc atgtcaggac | 300 |
| tgcagcagca aagccaattt atcaggaggt gtttggaaag ataacatcaa catggctcta | 360 |
| gttgtggaca cctactatga tgatcaactc attagctgtg gcagcgtcaa cagagggacc | 420 |
| tgccagcgac atgtcttcc ccacaatcat actgctgaca cagtcggag ggttcactgc | 480 |
| atattctccc cacagataga agagcccagc cagtgtcctg actgtgtggt gagcgccctg | 540 |
| ggagccaaag tcctttcatc tgtaaaggac cggttcatca acttctttgt aggcaatacc | 600 |
| ataaattctt cttatttccc agatcatcca ttgcattcga tatcagtgag aaggctaaag | 660 |
| gaaacgaaag atggttttat gttttgacg gaccagtcct acattgatgt tttacctgag | 720 |
| ttcagagatt cttaccccat taagtatgtc catgcctttg aaagcaacaa ttttatttac | 780 |
| ttcttgacgg tccaaaggga aactctagat gctcagactt tcacacaag aataatcagg | 840 |
| ttctgttcca taaactctgg attgcattcc tacatggaaa tgcctctgga gtgtattctc | 900 |
| acagaaaaga gaaaaagag atccacaaag aaggaagtgt taatatact caggctgcg | 960 |
| tatgtcagca agcctggggc ccagcttgct agacaaatag gagccagcct gaatgatgac | 1020 |
| attctttccg gggtgttcgc acaaagcaag ccagattctg ccgaaccaat ggatcgatct | 1080 |
| gccatgtgtg cattccctat caaatatgtc aacgacttct caacaagat cgtcaacaaa | 1140 |
| aacaatgtga gatgtctcca gcatttttac ggacccaatc atgagcactg ctttaatagg | 1200 |
| acacttctga gaaattcatc aggctgtgaa gcgcgcgtg atgaatatcg aacagagttt | 1260 |
| accacagctt tgcagcgcgt tgacttattc atgggtcaat tcagcgaagt cctcttaaca | 1320 |

```
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggttgc   1560
agacatttcc agtcttgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa   1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtcgatcc tgtaataaca   1980
agtatttcgc cgaaatacgg tcctatggct ggtggcactt tacttacttt aactggaaat   2040
tacctaaaca gtgggaactc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaactcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atggcatcct ttccaaatac tttgatctca tttatgtaca taatcctgtg   2520
tttgagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggtg gttcttcggg ttcaggctcg   2820
ggctccacag gtacatcgtc atcgggtaca ggtacttcag ctggcacaac gggtacctcc   2880
gcatctactt ccggttcagg ctccggaggc ggcggcggct cgggtggtgg tggatctgcc   2940
ggcggaaccg caaccgcagg cgcttcttct ggttccgaca ttgtgctgac ccaatctcca   3000
gcttctttgg ctgtgtctct agggcagagg gccaccatct cctgcaaggc cagccaaagt   3060
gttgattatg atggtggtag ttatatgagt tggttccaac agagaccagg acagccaccc   3120
aaactcctca tctctgctgc atccaacctt gaatctggca tcccagccag gtttagtggc   3180
agtggctctg ggacagactt caccctcaat atccatcctg tggaggagga ggatgttgca   3240
acctattact gtcagcaaag ttatgaagac ccgctcacgt tcggtgctgg gaccaaggtg   3300
gagatcaaac gaactgtggc tgcaccatct gtcttcatct tcccgccatc tgatgagcag   3360
ttgaaatctg gaactgcctc tgttgtgtgc ctgctgaata acttctatcc cagagaggcc   3420
aaagtacagt ggaaggtgga taacgccctc caatcgggta actcccagga gagtgtcaca   3480
gagcaggaca gcaaggacag cacctacagc ctcagcagca cctgacgct gagcaaagca   3540 gactacgaga aacacaaagt ctacgcctgc gaagtcaccc atcagggcct gagctcgccc   3600
gtcacaaaga gcttcaacag gggagagtgt ggtggttctt cggttcagg ctcgggctcc   3660 acaggtacat cgtcatcggg tacaggtact tcagctggca caacgggtac ctccgcatct   3720
```

```
acttccggtt caggctccgg aggcggcggc ggctcgggtg gtggtggatc tgccggcgga    3780
accgcaaccg caggcgcttc ttctggttcc gtccaactgc agcagcctgg gactgaactg    3840
gtgaagcctg ggcttcagt gaagctgtcc tgcaaggctt ctggctacac cttcaccagt    3900
tactggatac actgggtgaa gcagaggcct ggacaaggcc ttgagtggat tggagagatt    3960
aatcctagca gcggtcgtac taactacaac gagaaattca agaacaaggt cacagtgact    4020
gtagacaaat cttccaccac agcctacatg caactcagca acctgacatc tgaggactct    4080
gcggtctatt actgtgcaag tagggggctac tggggccaag gcaccactct cacagtctcc    4140
tcagctagca cgaagggccc atcggtcttc cccctggcac cctcctccaa gagcacctct    4200
gggggcacag cggccctggg ctgcctggtc aaggactact ccccgaaccc gtgacggtg    4260 tcgtggaact caggcgccct gaccagcggc gtgcacacct tcccggctgt cctacagtcc    4320
tcaggactct actccctcag cagcgtggtg accgtgccct ccagcagctt gggcacccag    4380
acctacatct gcaacgtgaa tcacaagccc agcaacacca aggtggacaa gaaagttgag    4440
cccaaatctt gtgacaaaac tcacacaacg cgtggtgccg catggagcca ccccagttc    4500 gaaaaggggg ccgcatggag ccaccccag ttcgaaaaag gggccgcatg gagccacccc    4560
cagttcgaaa aggggccgc acaccatcac catcaccatt ag                       4602
```

<210> SEQ ID NO 31
<211> LENGTH: 4824
<212> TYPE: DNA
<213> ORGANISM: artificial
<220> FEATURE:
<223> OTHER INFORMATION: decoyMET-linker-antibody
      nucleotide seq K842E-linker L134-scMvDN30

<400> SEQUENCE: 31

```
atgaaggccc ccgctgtgct tgcacctggc atcctcgtgc tcctgtttac cttggtgcag     60
aggagcaatg ggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg aacacccag attgtttccc atgtcaggac    300
tgcagcagca agccaatttt atcaggaggt gtttggaaag ataacatcaa catggctcta    360
gttgtggaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttttgacg gaccagtcct acattgatgt tttacctgag    720
ttcagagatt cttaccccat taagtatgtc catgcctttg aaagcaacaa tttttatttac    780 ttcttgacgg tccaaaggga aactctagat gctcagactt tcacacaag aataatcagg    840 ttctgttcca taaactctgg attgcattcc tacatggaaa tgcctctgga gtgtattctc    900
acagaaaaga gaaaaaagag atccacaaag aaggaagtgt taatatact tcaggctgcg    960 tatgtcagca agcctgggc ccagcttgct agacaaatag agccagcct gaatgatgac    1020 attctttccg gggtgttcgc acaaagcaag ccagattctg ccgaaccaat ggatcgatct    1080
gccatgtgtg cattccctat caaatatgtc aacgacttct caacaagat cgtcaacaaa    1140
```

```
aacaatgtga gatgtctcca gcattttac ggacccaatc atgagcactg ctttaatagg     1200
acacttctga gaaattcatc aggctgtgaa gcgcgccgtg atgaatatcg aacagagttt     1260
accacagctt tgcagcgcgt tgacttattc atgggtcaat tcagcgaagt cctcttaaca     1320
tctatatcca ccttcattaa aggagacctc accatagcta atcttgggac atcagagggt     1380
cgcttcatgc aggttgtggt ttctcgatca ggaccatcaa cccctcatgt gaattttctc     1440
ctggactccc atccagtgtc tccagaagtg attgtggagc atacattaaa ccaaaatggc     1500
tacacactgg ttatcactgg gaagaagatc acgaagatcc cattgaatgg cttgggttgc     1560
agacatttcc agtcttgcag tcaatgcctc tctgccccac cctttgttca gtgtggctgg     1620
tgccacgaca aatgtgtgcg atcggaggaa tgcctgagcg ggacatggac tcaacagatc     1680
tgtctgcctg caatctacaa ggttttccca aatagtgcac cccttgaagg agggacaagg     1740
ctgaccatat gtggctggga ctttggattt cggaggaata ataaatttga tttaaagaaa     1800
actagagttc tccttggaaa tgagagctgc accttgactt taagtgagag cacgatgaat     1860
acattgaaat gcacagttgg tcctgccatg aataagcatt tcaatatgtc cataattatt     1920
tcaaatggcc acgggacaac acaatacagt acattctcct atgtcgatcc tgtaataaca     1980
agtatttcgc cgaaatacgg tcctatggct ggtggcactt tacttacttt aactggaaat     2040
tacctaaaca gtgggaactc tagacacatt tcaattggtg gaaaaacatg tactttaaaa     2100
agtgtgtcaa acagtattct tgaatgttat accccagccc aaaccatttc aactgagttt     2160
gctgttaaat tgaaaattga cttagccaac cgagagacaa gcatcttcag ttaccgtgaa     2220
gatcccattg tctatgaaat tcatccaacc aaatctttta ttagtggtgg gagcacaata     2280
acaggtgttg ggaaaaacct gaactcagtt agtgtcccga gaatggtcat aaatgtgcat     2340
gaagcaggaa ggaactttac agtggcatgt caacatcgct ctaattcaga gataatctgt     2400
tgtaccactc cttccctgca acagctgaat ctgcaactcc ccctgaaaac caaagccttt     2460
ttcatgttag atggcatcct ttccaaatac tttgatctca tttatgtaca taatcctgtg     2520
tttgagcctt ttgaaaagcc agtgatgatc tcaatgggca atgaaaatgt actggaaatt     2580
aagggaaatg atattgaccc tgaagcagtt aaaggtgaag tgttaaaagt tggaaataag     2640
agctgtgaga atatacactt acattctgaa gccgttttat gcacggtccc caatgacctg     2700
ctgaaattga cagcgagct aaatatagag tggaagcaag caatttcttc aaccgtcctt     2760
ggaaaagtaa tagttcaacc agatcagaat ttcacaggtg gtggtggttc tggtggtggt     2820
ggttcaggcg gcggcggctc ggcagaggca tggtataatc tcgggaacgc atactacaaa     2880
cagggcgatt atcagaaggc tatcgaatac taccaaaaag cactcgaact ggaccccaat     2940
aacgcggagg catggtacaa tctcgggaat gcgtactata gcagggtga ctaccagaag     3000 gccattgaat actaccaaaa ggcgcttgaa ctggacccga caacgccga ggcctggtat     3060 aacctgggga tgcttattca aagcagggg gattatcaaa aggcaataga agactaccag     3120 aaggcctcg aattggaccc taacaatggt ggtggtggtt ctggtggtgg tggttcaggc     3180
ggcggcggct cgggcggaga cattgtgctg acccaatctc cagcttcttt ggctgtgtct     3240
ctagggcaga gggccaccat ctcctgcaag gccagccaaa gtgttgatta tgatggtggt     3300
agttatatga gttggttcca acagagacca ggacagccac ccaaactcct catctctgct     3360
gcatccaacc ttgaatctgg catcccagcc aggtttagtg gcagtggctc tgggacagac     3420 ttcacccctca atatccatcc tgtggaggag gaggatgttg caacctatta ctgtcagcaa     3480
```

| | |
|---|---|
| agttatgaag acccgctcac gttcggtgct ggtaccaagg tggagatcaa acgaactgtg | 3540 |
| gctgcaccat ctgtcttcat cttcccgcca tctgatgagc agttgaaatc tggaactgcc | 3600 |
| tctgttgtgt gcctgctgaa taacttctat cccagagagg ccaaagtaca gtggaaggtg | 3660 |
| gataacgccc tccaatcggg taactcccag gagagtgtca cagagcagga cagcaaggac | 3720 |
| agcacctaca gcctcagcag caccctgacg ctgagcaaag cagactacga gaaacacaaa | 3780 |
| gtctacgcct gcgaagtcac ccatcagggc ctgagctcgc ccgtcacaaa gagcttcaac | 3840 |
| aggggagagt gtggtggttc ttcgggttca ggctcgggct ccacaggtac atcgtcatcg | 3900 |
| ggtacaggta cttcagctgg cacaacgggt acctccgcat ctacttccgg ttcaggctcc | 3960 |
| ggaggcggcg gcggctcggg tggtggtgga tctgccggcg gaaccgcaac cgcaggcgct | 4020 |
| tcttctggtt ccgtccaact gcagcagcct gggactgaac tggtgaagcc tgggggcttca | 4080 |
| gtgaagctgt cctgcaaggc ttctggctac accttcacca gttactggat acactgggtg | 4140 |
| aagcagaggc ctggacaagg ccttgagtgg attggagaga ttaatcctag cagcggtcgt | 4200 |
| actaactaca acgagaaatt caagaacaag gtcacagtga ctgtagacaa atcttccacc | 4260 |
| acagcctaca tgcaactcag caacctgaca tctgaggact ctgcggtcta ttactgtgca | 4320 |
| agtaggggct actggggcca aggcaccact ctcacagtct cctcagctag cacgaagggc | 4380 |
| ccatcggtct tccccctggc accctcctcc aagagcacct ctgggggcac agcggccctg | 4440 |
| ggctgcctgg tcaaggacta cttccccgaa cccgtgacgg tgtcgtggaa ctcaggcgcc | 4500 |
| ctgaccagcg gcgtgcacac cttcccggct gtcctacagt cctcaggact ctactccctc | 4560 |
| agcagcgtgg tgaccgtgcc ctccagcagc ttgggcaccc agacctacat ctgcaacgtg | 4620 |
| aatcacaagc ccagcaacac caaggtggac aagaaagttg agcccaaatc ttgtgacaaa | 4680 |
| actcacacaa cgcgtggtgc cgcatggagc caccccagt tcgaaaaagg ggccgcatgg | 4740 |
| agccacccc agttcgaaaa aggggccgca tggagccacc cccagttcga aaaggggcc | 4800 |
| gcacaccatc accatcacca ttag | 4824 |

<210> SEQ ID NO 32
<211> LENGTH: 4583
<212> TYPE: DNA
<213> ORGANISM: artificial
<220> FEATURE:
<223> OTHER INFORMATION: antibody-linker-decoyMET
    nucleotide seq scMvDN30-linker L45-K842E

<400> SEQUENCE: 32

| | |
|---|---|
| ggatccccg gggccaccat ggagacagac acaatcctgc tatgggtgct gctgctctgg | 60 |
| gttccaggct ccactggtga cattgtgctg acccaatctc cagcttcttt ggctgtgtct | 120 |
| ctagggcaga gggccaccat ctcctgcaag gccagccaaa gtgttgatta tgatggtggt | 180 |
| agttatatga gttggttcca acagagacca ggacagccac ccaaactcct catctctgct | 240 |
| gcatccaacc ttgaatctgg catcccagcc aggtttagtg gcagtggctc tgggacagac | 300 |
| ttcaccctca atatccatcc tgtggaggag gaggatgttg caacctatta ctgtcagcaa | 360 |
| agttatgaag acccgctcac gttcggtgct ggtaccaagg tggagatcaa acgaactgtg | 420 |
| gctgcaccat ctgtcttcat cttcccgcca tctgatgagc agttgaaatc tggaactgcc | 480 |
| tctgttgtgt gcctgctgaa taacttctat cccagagagg ccaaagtaca gtggaaggtg | 540 |
| gataacgccc tccaatcggg taactcccag gagagtgtca cagagcagga cagcaaggac | 600 |
| agcacctaca gcctcagcag caccctgacg ctgagcaaag cagactacga gaaacacaaa | 660 |

```
gtctacgcct gcgaagtcac ccatcagggc ctgagctcgc ccgtcacaaa gagcttcaac    720
aggggagagt gtggtggttc ttcgggttca ggctcgggct ccacaggtac atcgtcatcg    780
ggtacaggta cttcagctgg cacaacgggt acctccgcat ctacttccgg ttcaggctcc    840
ggaggcggcg gcggctcggg tggtggtgga tctgccggcg gaaccgcaac cgcaggcgct    900
tcttctggtt ccgtccaact gcagcagcct gggactgaac tggtgaagcc tggggcttca    960
gtgaagctgt cctgcaaggc ttctggctac accttcacca gttactggat acactgggtg   1020
aagcagaggc ctggacaagg ccttgagtgg attggagaga ttaatcctag cagcggtcgt   1080
actaactaca acgagaaatt caagaacaag gtcacagtga ctgtagacaa atcttccacc   1140
acagcctaca tgcaactcag caacctgaca tctgaggact ctgcggtcta ttactgtgca   1200
agtaggggct actggggcca aggcaccact ctcacagtct cctcagcaag cacgaagggc   1260
ccatcggtct tccccctggc accctcctcc aagagcacct ctgggggcac agcggccctg   1320
ggctgcctgg tcaaggacta cttccccgaa cccgtgacgg tgtcgtggaa ctcaggcgcc   1380
ctgaccagcg gcgtgcacac cttcccggct gtcctacagt cctcaggact ctactccctc   1440
agcagcgtgg tgaccgtgcc ctccagcagc ttgggcaccc agacctacat ctgcaacgtg   1500
aatcacaagc ccagcaacac caaggtggac aagaaagttg agcccaaatc ttgtgacaaa   1560
actcacacag ctgaagctgc agccaaagaa gctgcagcca agaggccgc agctaaggaa    1620 gccgcagcaa aagctgctgc tgaagctgca gccaaagaag ctgcagccaa agaggccgca   1680
gctaaggaag ccgcagcaaa agctgagtgt aaagaggcac tagcaaagtc cgagatgaat   1740
gtgaatatga agtatcagct tcccaacttc accgcgaaa cacccatcca gaatgtcatt    1800
ctacatgagc atcacatttt ccttggtgcc actaactaca tttatgtttt aaatgaggaa   1860
gaccttcaga aggttgctga gtacaagact gggcctgtgc tggaacaccc agattgtttc   1920
ccatgtcagg actgcagcag caaagccaat ttatcaggag gtgtttggaa agataacatc   1980
aacatggctc tagttgtgga cacctactat gatgatcaac tcattagctg tggcagcgtc   2040
aacagaggga cctgccagcg acatgtcttt ccccacaatc atactgctga catacagtcg   2100
gaggttcact gcatattctc cccacagata gaagagccca gccagtgtcc tgactgtgtg   2160
gtgagcgccc tgggagccaa agtcctttca tctgtaaagg accggttcat caacttcttt   2220
gtaggcaata ccataaattc ttcttatttc ccagatcatc cattgcattc gatatcagtg   2280
agaaggctaa aggaaacgaa agatggtttt atgtttttga cggaccagtc ctacattgat   2340 gtittacctg agttcagaga ttcttacccc attaagtatg tccatgcctt tgaaagcaac   2400
aattttattt acttcttgac ggtccaaagg gaaactctag atgctcagac ttttcacaca   2460
agaataatca ggttctgttc cataaactct ggattgcatt cctacatgga aatgcctctg   2520
gagtgtattc tcacagaaaa gagaaaaaag agatccacaa gaaggaagt gtttaatata    2580 cttcaggctg cgtatgtcag caagcctggg gcccagcttg ctagacaaat aggagccagc   2640
ctgaatgatg acattctttt cggggtgttc gcacaaagca agccagattc tgccgaacca   2700
atggatcgat ctgccatgtg tgcattccct atcaaatatg tcaacgactt cttcaacaag   2760
atcgtcaaca aaaacaatgt gagatgtctc cagcattttt acggacccaa tcatgagcac   2820
tgctttaata ggacacttct gagaaattca tcaggctgtg aagcgcgccg tgatgaatat   2880
cgaacagagt ttaccacagc tttgcagcgc gttgacttat tcatgggtca attcagcgaa   2940
gtcctcttaa catctatatc caccttcatt aaaggagacc tcaccatagc taatcttggg   3000
acatcagagg gtcgcttcat gcaggttgtg gtttctcgat caggaccatc aaccccctcat  3060
```

```
gtgaatttc tcctggactc ccatccagtg tctccagaag tgattgtgga gcatacatta    3120
aaccaaaatg gctacacact ggttatcact gggaagaaga tcacgaagat cccattgaat    3180
ggcttgggtt gcagacattt ccagtcttgc agtcaatgcc tctctgcccc acccttttgtt   3240
cagtgtggct ggtgccacga caaatgtgtg cgatcggagg aatgcctgag cgggacatgg    3300
actcaacaga tctgtctgcc tgcaatctac aaggttttcc caaatagtgc accccttgaa    3360
ggagggacaa ggctgaccat atgtggctgg gactttggat ttcggaggaa taataaattt    3420
gatttaaaga aaactagagt tctccttgga aatgagagct gcaccttgac tttaagtgag    3480
agcacgatga atacattgaa atgcacagtt ggtcctgcca tgaataagca tttcaatatg    3540
tccataatta tttcaaatgg ccacgggaca acacaataca gtacattctc ctatgtcgat    3600
cctgtaataa caagtatttc gccgaaatac ggtcctatgg ctggtggcac tttacttact    3660
ttaactggaa attacctaaa cagtgggaac tctagacaca tttcaattgg tggaaaaaca    3720
tgtactttaa aaagtgtgtc aaacagtatt cttgaatgtt ataccccagc ccaaaccatt    3780
tcaactgagt ttgctgttaa attgaaaatt gacttagcca accgagagac aagcatcttc    3840
agttaccgtg aagatcccat tgtctatgaa attcatccaa ccaaatcttt tattagtggt    3900
gggagcacaa taacaggtgt tgggaaaaac ctgaactcag ttagtgtccc gagaatggtc    3960
ataaatgtgc atgaagcagg aaggaacttt acagtggcat gtcaacatcg ctctaattca    4020
gagataatct gttgtaccac tccttccctg caacagctga atctgcaact ccccctgaaa    4080
accaaagcct ttttcatgtt agatggcatc ctttccaaat actttgatct catttatgta    4140
cataatcctg tgtttgagcc ttttgaaaag ccagtgatga tctcaatggg caatgaaaat    4200
gtactgaaaa ttaagggaaa tgatattgac cctgaagcag ttaaaggtga agtgttaaaa    4260
gttggaaata agagctgtga aaatatacac ttacattctg aagccgtttt atgcacggtc    4320
cccaatgacc tgctgaaatt gaacagcgag ctaaatatag agtggaagca agcaattctt    4380
tcaaccgtcc ttggaaaagt aatagttcaa ccagatcaga atttcacagc tagcggtgcc    4440
gcatggagcc accccagtt cgaaaaaggg gccgcatgga gcacccca gttcgaaaaa        4500
ggggccgcat ggagccaccc ccagttcgaa aaagggccg cacaccatca ccatcaccat    4560
taggtcgacc tcgaggcggc cgc                                            4583
```

<210> SEQ ID NO 33
<211> LENGTH: 4628
<212> TYPE: DNA
<213> ORGANISM: artificial
<220> FEATURE:
<223> OTHER INFORMATION: antibody-linker-decoyMET
    nucleotide seq scMvDN30-linker L60-K842E

<400> SEQUENCE: 33

```
ggatccccg gggccaccat ggagacagac acaatcctgc tatgggtgct gctgctctgg     60
gttccaggct ccactggtga cattgtgctg acccaatctc cagcttcttt ggctgtgtct    120
ctagggcaga gggccaccat ctcctgcaag gccagccaaa gtgttgatta tgatggtggt    180
agttatatga gttggttcca acagagacca ggacagccac ccaaactcct catctctgct    240
gcatccaacc ttgaatctgg catcccagcc aggtttagtg gcagtggctc tgggacagac    300
ttcaccctca atatccatcc tgtggaggag gaggatgttg caacctatta ctgtcagcaa    360
agttatgaag acccgctcac gttcggtgct ggtaccaagg tggagatcaa acgaactgtg    420
gctgcaccat ctgtcttcat cttcccgcca tctgatgagc agttgaaatc tggaactgcc    480
```

```
tctgttgtgt gcctgctgaa taacttctat cccagagagg ccaaagtaca gtggaaggtg    540
gataacgccc tccaatcggg taactcccag gagagtgtca cagagcagga cagcaaggac    600
agcacctaca gcctcagcag caccctgacg ctgagcaaag cagactacga gaaacacaaa    660
gtctacgcct gcgaagtcac ccatcagggc ctgagctcgc ccgtcacaaa gagcttcaac    720
aggggagagt gtggtggttc ttcgggttca ggctcgggct ccacaggtac atcgtcatcg    780
ggtacaggta cttcagctgg cacaacgggt acctccgcat ctacttccgg ttcaggctcc    840
ggaggcggcg gcggctcggg tggtggtgga tctgccggcg gaaccgcaac cgcaggcgct    900
tcttctggtt ccgtccaact gcagcagcct gggactgaac tggtgaagcc tggggcttca    960
gtgaagctgt cctgcaaggc ttctggctac accttcacca gttactggat acactgggtg   1020
aagcagaggc ctgacaagg ccttgagtgg attggagaga ttaatcctag cagcggtcgt    1080
actaactaca acgagaaatt caagaacaag gtcacagtga ctgtagacaa atcttccacc   1140
acagcctaca tgcaactcag caacctgaca tctgaggact ctgcggtcta ttactgtgca   1200
agtaggggct actggggcca aggcaccact ctcacagtct cctcagcaag cacgaagggc   1260
ccatcggtct tccccctggc accctcctcc aagagcacct ctgggggcac agcggccctg   1320
ggctgcctgg tcaaggacta cttccccgaa cccgtgacgg tgtcgtggaa ctcaggcgcc   1380
ctgaccagcg gcgtgcacac cttcccggct gtcctacagt cctcaggact ctactccctc   1440
agcagcgtgg tgaccgtgcc ctccagcagc ttgggcaccc agacctacat ctgcaacgtg   1500
aatcacaagc ccagcaacac caaggtggac aagaaagttg agcccaaatc ttgtgacaaa   1560
actcacacag gtggttcttc gggttcaggc tcgggctcca caggtacatc gtcatcgggt   1620
acaggtactt cagctggcac aacgggtacc tccgcatcta cttccggttc aggctccgga   1680
ggcggcggcg gctcgggtgg tggtggatct gccggcggaa ccgcaaccgc aggcgcttct   1740
tctggttccg agtgtaaaga ggcactagca aagtccgaga tgaatgtgaa tatgaagtat   1800
cagcttccca acttcaccgc ggaaacaccc atccagaatg tcattctaca tgagcatcac   1860
attttccttg gtgccactaa ctacatttat gttttaaatg aggaagacct tcagaaggtt   1920
gctgagtaca agactgggcc tgtgctggaa cacccagatt gtttcccatg tcaggactgc   1980
agcagcaaag ccaatttatc aggaggtgtt tggaaagata acatcaacat ggctctagtt   2040
gtggacacct actatgatga tcaactcatt agctgtggca gcgtcaacag agggacctgc   2100
cagcgacatg tctttcccca caatcatact gctgacatac agtcggaggt tcactgcata   2160
ttctccccac agatagaaga gcccagccag tgtcctgact gtgtggtgag cgccctggga   2220
gccaaagtcc tttcatctgt aaaggaccgg ttcatcaact tctttgtagg caataccata   2280
aattcttctt atttcccaga tcatccattg cattcgatat cagtgagaag gctaaaggaa   2340
acgaaagatg gttttatgtt tttgacggac cagtcctaca ttgatgtttt acctgagttc   2400
agagattctt accccattaa gtatgtccat gcctttgaaa gcaacaattt tatttacttc   2460
ttgacggtcc aaagggaaac tctagatgct cagacttttc acacaagaat aatcaggttc   2520
tgttccataa actctggatt gcattcctac atgaaatgc ctctggagtg tattctcaca   2580
gaaaagagaa aaaagagatc cacaaagaag gaagtgttta tatacttca ggctgcgtat   2640
gtcagcaagc ctgggccca gcttgctaga caaataggag ccagcctgaa tgatgacatt   2700
cttttcgggt tgttcgcaca aagcaagcca gattctgccg aaccaatgga tcgatctgcc   2760
atgtgtgcat tccctatcaa atatgtcaac gacttcttca acaagatcgt caacaaaaac   2820
```

-continued

| | |
|---|---|
| aatgtgagat gtctccagca tttttacgga cccaatcatg agcactgctt taataggaca | 2880 |
| cttctgagaa attcatcagg ctgtgaagcg cgccgtgatg aatatcgaac agagtttacc | 2940 |
| acagctttgc agcgcgttga cttattcatg ggtcaattca gcgaagtcct cttaacatct | 3000 |
| atatccacct tcattaaagg agacctcacc atagctaatc ttgggacatc agagggtcgc | 3060 |
| ttcatgcagg ttgtggtttc tcgatcagga ccatcaaccc ctcatgtgaa ttttctcctg | 3120 |
| gactcccatc cagtgtctcc agaagtgatt gtggagcata cattaaacca aaatggctac | 3180 |
| acactggtta tcactgggaa gaagatcacg aagatcccat gaatggctt gggttgcaga | 3240 |
| catttccagt cttgcagtca atgcctctct gccccaccct ttgttcagtg tggctggtgc | 3300 |
| cacgacaaat gtgtgcgatc ggaggaatgc ctgagcggga catggactca acagatctgt | 3360 |
| ctgcctgcaa tctacaaggt tttcccaaat agtgcacccc ttgaaggagg acaaggctg | 3420 |
| accatatgtg gctgggactt tggatttcgg aggaataata aatttgattt aaagaaaact | 3480 |
| agagttctcc ttggaaatga gagctgcacc ttgactttaa gtgagagcac gatgaataca | 3540 |
| ttgaaatgca cagttggtcc tgccatgaat aagcatttca atatgtccat aattatttca | 3600 |
| aatggccacg ggacaacaca atacagtaca ttctcctatg tcgatcctgt aataacaagt | 3660 |
| atttcgccga aatacggtcc tatggctggt ggcactttac ttactttaac tggaaattac | 3720 |
| ctaaacagtg ggaactctag acacatttca attggtggaa aaacatgtac tttaaaaagt | 3780 |
| gtgtcaaaca gtattcttga atgttatacc ccagcccaaa ccatttcaac tgagtttgct | 3840 |
| gttaaattga aaattgactt agccaaccga gagacaagca tcttcagtta ccgtgaagat | 3900 |
| cccattgtct atgaaattca tccaaccaaa tcttttatta gtggtgggag cacaataaca | 3960 |
| ggtgttggga aaacctgaa ctcagttagt gtcccgagaa tggtcataaa tgtgcatgaa | 4020 |
| gcaggaagga actttacagt ggcatgtcaa catcgctcta attcagagat aatctgttgt | 4080 |
| accactcctt ccctgcaaca gctgaatctg caactccccc tgaaaaccaa agccttttc | 4140 |
| atgttagatg gcatcctttc caaatacttt gatctcattt atgtacataa tcctgtgttt | 4200 |
| gagcctttg aaaagccagt gatgatctca atgggcaatg aaaatgtact ggaaattaag | 4260 |
| ggaaatgata ttgaccctga agcagttaaa ggtgaagtgt taaagttgg aaataagagc | 4320 |
| tgtgagaata tacacttaca ttctgaagcc gttttatgca cggtccccaa tgacctgctg | 4380 |
| aaattgaaca gcgagctaaa tatagagtgg aagcaagcaa tttcttcaac cgtccttgga | 4440 |
| aaagtaatag ttcaaccaga tcagaatttc acagctagcg gtgccgcatg gagccacccc | 4500 |
| cagttcgaaa aggggccgc atggagccac cccccagttcg aaaaggggc cgcatggagc | 4560 |
| caccccagt tcgaaaaagg ggccgcacac catcaccatc accattaggt cgacctcgag | 4620 |
| gcggccgc | 4628 |

<210> SEQ ID NO 34
<211> LENGTH: 4850
<212> TYPE: DNA
<213> ORGANISM: artificial
<220> FEATURE:
<223> OTHER INFORMATION: antibody-linker-decoyMET
      nucleotide seq scMvDN30-linker L134-K842E

<400> SEQUENCE: 34

| | |
|---|---|
| ggatccccg gggccaccat ggagacagac acaatcctgc tatgggtgct gctgctctgg | 60 |
| gttccaggct ccactggtga cattgtgctg acccaatctc cagcttcttt ggctgtgtct | 120 |
| ctagggcaga gggccaccat ctcctgcaag gccagccaaa gtgttgatta tgatggtggt | 180 |

```
agttatatga gttggttcca acagagacca ggacagccac ccaaactcct catctctgct    240
gcatccaacc ttgaatctgg catcccagcc aggtttagtg gcagtggctc tgggacagac    300
ttcaccctca atatccatcc tgtggaggag gaggatgttg caacctatta ctgtcagcaa    360
agttatgaag acccgctcac gttcggtgct ggtaccaagg tggagatcaa acgaactgtg    420
gctgcaccat ctgtcttcat cttcccgcca tctgatgagc agttgaaatc tggaactgcc    480
tctgttgtgt gcctgctgaa taacttctat cccagagagg ccaaagtaca gtggaaggtg    540
gataacgccc tccaatcggg taactcccag gagagtgtca cagagcagga cagcaaggac    600
agcacctaca gcctcagcag caccctgacg ctgagcaaag cagactacga gaaacacaaa    660
gtctacgcct gcgaagtcac ccatcagggc ctgagctcgc ccgtcacaaa gagcttcaac    720
aggggagagt gtggtggttc ttcgggttca ggctcgggct ccacaggtac atcgtcatcg    780
ggtacaggta cttcagctgg cacaacgggt acctccgcat ctacttccgg ttcaggctcc    840
ggaggcggcg gcggctcggg tggtggtgga tctgccggcg gaaccgcaac cgcaggcgct    900
tcttctggtt ccgtccaact gcagcagcct gggactgaac tggtgaagcc tggggcttca    960
gtgaagctgt cctgcaaggc ttctggctac accttcacca gttactggat acactgggtg   1020
aagcagaggc ctgacaagg ccttgagtgg attggagaga ttaatcctag cagcggtcgt   1080
actaactaca cgagaaatt caagaacaag gtcacagtga ctgtagacaa atcttccacc   1140
acagcctaca tgcaactcag caacctgaca tctgaggact ctgcggtcta ttactgtgca   1200
agtaggggct actggggcca aggcaccact ctcacagtct cctcagcaag cacgaagggc   1260
ccatcggtct tccccctggc accctcctcc aagagcacct ctgggggcac agcggccctg   1320
ggctgcctgg tcaaggacta cttccccgaa cccgtgacgg tgtcgtggaa ctcaggcgcc   1380
ctgaccagcg gcgtgcacac cttcccggct gtcctacagt cctcaggact ctactccctc   1440
agcagcgtgg tgaccgtgcc ctccagcagc ttgggcaccc agacctacat ctgcaacgtg   1500
aatcacaagc ccagcaacac caaggtggac aagaaagttg agcccaaatc ttgtgacaaa   1560
actcacacag gtggtggtgg ttctggtggt ggtggttcag gcggcggcgg ctcggcagag   1620
gcatggtata atctcgggaa cgcatactac aaacagggcg attatcagaa ggctatcgaa   1680
tactaccaaa aagcactcga actggacccc aataacgcgg aggcatggta caatctcggg   1740
aatgcgtact ataagcaggg tgactaccag aaggccattg aatactacca aaaggcgctt   1800
gaactggacc cgaacaacgc cgaggcctgg tataacctgg ggaatgctta ttacaagcag   1860
ggggattatc aaaaggcaat agaagactac cagaaggccc tcgaattgga ccctaacaat   1920
ggtggtggtg gttctggtgg tggtggttca ggcggcggcg gctcgggcgg agagtgtaaa   1980
gaggcactag caaagtccga gatgaatgtg aatatgaagt atcagcttcc caacttcacc   2040
gcggaaacac ccatccagaa tgtcattcta catgagcatc acattttcct tggtgccact   2100
aactacattt atgttttaaa tgaggaagac cttcagaagg ttgctgagta caagactggg   2160
cctgtgctgg aacacccaga ttgtttccca tgtcaggact gcagcagcaa agccaattta   2220
tcaggaggtg tttggaaaga taacatcaac atggctctag ttgtggacac ctactatgat   2280
gatcaactca ttagctgtgg cagcgtcaac agagggacct gccagcgaca tgtctttccc   2340
cacaatcata ctgctgacat acagtcggag gttcactgca tattctcccc acagatagaa   2400
gagcccagcc agtgtcctga ctgtgtggtg agcgccctgg gagccaaagt cctttcatct   2460
gtaaaggacc ggttcatcaa cttctttgta ggcaatacca taaattcttc ttatttccca   2520
gatcatccat tgcattcgat atcagtgaga aggctaaagg aaacgaaaga tggttttatg   2580
```

```
tttttgacgg accagtccta cattgatgtt ttacctgagt tcagagattc ttaccccatt    2640
aagtatgtcc atgcctttga aagcaacaat tttatttact tcttgacggt ccaaagggaa    2700
actctagatg ctcagacttt tcacacaaga ataatcaggt tctgttccat aaactctgga    2760
ttgcattcct acatggaaat gcctctggag tgtattctca cagaaaagag aaaaaagaga    2820
tccacaaaga aggaagtgtt taatatactt caggctgcgt atgtcagcaa gcctggggcc    2880
cagcttgcta gacaaatagg agccagcctg aatgatgaca ttcttttcgg ggtgttcgca    2940
caaagcaagc cagattctgc cgaaccaatg gatcgatctg ccatgtgtgc attccctatc    3000
aaatatgtca acgacttctt caacaagatc gtcaacaaaa acaatgtgag atgtctccag    3060
cattttacg gacccaatca tgagcactgc tttaatagga cacttctgag aaattcatca    3120
ggctgtgaag cgcgccgtga tgaatatcga acagagttta ccacagcttt gcagcgcgtt    3180
gacttattca tgggtcaatt cagcgaagtc ctcttaacat ctatatccac cttcattaaa    3240
ggagacctca ccatagctaa tcttgggaca tcagagggtc gcttcatgca ggttgtggtt    3300
tctcgatcag gaccatcaac ccctcatgtg aattttctcc tggactccca tccagtgtct    3360
ccagaagtga ttgtggagca tacattaaac caaaatggct acacactggt tatcactggg    3420
aagaagatca cgaagatccc attgaatggc ttgggttgca gacatttcca gtcttgcagt    3480
caatgcctct ctgccccacc ctttgttcag tgtggctggt gccacgacaa atgtgtgcga    3540
tcggaggaat gcctgagcgg gacatggact caacagatct gtctgcctgc aatctacaag    3600
gttttcccaa atagtgcacc ccttgaagga gggacaaggc tgaccatatg tggctgggac    3660
tttggatttc ggaggaataa taaatttgat ttaaagaaaa ctagagttct ccttggaaat    3720
gagagctgca ccttgacttt aagtgagagc acgatgaata cattgaaatg cacagttggt    3780
cctgccatga ataagcattt caatatgtcc ataattattt caaatggcca cgggacaaca    3840
caatacagta cattctccta tgtcgatcct gtaataacaa gtatttcgcc gaaatacggt    3900
cctatggctg gtggcacttt acttacttta actggaaatt acctaaacag tgggaactct    3960
agacacattt caattggtgg aaaaacatgt acttttaaaa gtgtgtcaaa cagtattctt    4020
gaatgttata ccccagccca aaccatttca actgagtttg ctgttaaatt gaaaattgac    4080
ttagccaacc gagagacaag catcttcagt taccgtgaag atcccattgt ctatgaaatt    4140
catccaacca aatcttttat tagtggtggg agcacaataa caggtgttgg gaaaaacctg    4200
aactcagtta gtgtcccgag aatggtcata aatgtgcatg aagcaggaag gaactttaca    4260
gtggcatgtc aacatcgctc taattcagag ataatctgtt gtaccactcc ttccctgcaa    4320
cagctgaatc tgcaactccc cctgaaaacc aaagccttt tcatgttaga tggcatcctt    4380
tccaaatact ttgatctcat ttatgtacat aatcctgtgt ttgagccttt tgaaaagcca    4440
gtgatgatct caatgggcaa tgaaaatgta ctggaaatta agggaaatga tattgaccct    4500
gaagcagtta aggtgaagt gttaaaagtt ggaaataaga gctgtgagaa tatcacttta    4560
cattctgaag ccgttttatg cacggtcccc aatgacctgc tgaaattgaa cagcgagcta    4620
aatatagagt ggaagcaagc aatttcttca accgtccttg gaaaagtaat agttcaacca    4680
gatcagaatt tcacagctag cggtgccgca tggagccacc cccagttcga aaagggggcc    4740
gcatggagcc accccagtt cgaaaagggg gccgcatgga gccacccca gttcgaaaaa    4800
ggggccgcac accatcacca tcaccattag gtcgacctcg aggcggccgc           4850
```

<210> SEQ ID NO 35

```
<211> LENGTH: 45
<212> TYPE: PRT
<213> ORGANISM: artificial
<220> FEATURE:
<223> OTHER INFORMATION: linker L45

<400> SEQUENCE: 35

Ala Glu Ala Ala Ala Lys Glu Ala Ala Ala Lys Glu Ala Ala Ala Lys
1               5                   10                  15

Glu Ala Ala Ala Lys Ala Ala Ala Glu Ala Ala Ala Lys Glu Ala Ala
            20                  25                  30

Ala Lys Glu Ala Ala Ala Lys Glu Ala Ala Ala Lys Ala
        35                  40                  45

<210> SEQ ID NO 36
<211> LENGTH: 60
<212> TYPE: PRT
<213> ORGANISM: artificial
<220> FEATURE:
<223> OTHER INFORMATION: linker L60

<400> SEQUENCE: 36

Gly Gly Ser Ser Gly Ser Gly Ser Gly Ser Thr Gly Thr Ser Ser Ser
1               5                   10                  15

Gly Thr Gly Thr Ser Ala Gly Thr Thr Gly Thr Ser Ala Ser Thr Ser
            20                  25                  30

Gly Ser Gly Ser Gly Gly Gly Gly Ser Gly Gly Gly Ser Ala
        35                  40                  45

Gly Gly Thr Ala Thr Ala Gly Ala Ser Ser Gly Ser
        50                  55                  60

<210> SEQ ID NO 37
<211> LENGTH: 134
<212> TYPE: PRT
<213> ORGANISM: artificial
<220> FEATURE:
<223> OTHER INFORMATION: linker L134

<400> SEQUENCE: 37

Gly Gly Gly Gly Ser Gly Gly Gly Ser Gly Gly Gly Gly Ser Ala
1               5                   10                  15

Glu Ala Trp Tyr Asn Leu Gly Asn Ala Tyr Tyr Lys Gln Gly Asp Tyr
            20                  25                  30

Gln Lys Ala Ile Glu Tyr Tyr Gln Lys Ala Leu Glu Leu Asp Pro Asn
        35                  40                  45

Asn Ala Glu Ala Trp Tyr Asn Leu Gly Asn Ala Tyr Tyr Lys Gln Gly
    50                  55                  60

Asp Tyr Gln Lys Ala Ile Glu Tyr Tyr Gln Lys Ala Leu Glu Leu Asp
65                  70                  75                  80

Pro Asn Asn Ala Glu Ala Trp Tyr Asn Leu Gly Asn Ala Tyr Tyr Lys
                85                  90                  95

Gln Gly Asp Tyr Gln Lys Ala Ile Glu Asp Tyr Gln Lys Ala Leu Glu
            100                 105                 110

Leu Asp Pro Asn Asn Gly Gly Gly Ser Gly Gly Gly Ser Gly
        115                 120                 125

Gly Gly Gly Ser Gly Gly
        130

<210> SEQ ID NO 38
<211> LENGTH: 135
```

```
<212> TYPE: DNA
<213> ORGANISM: artificial
<220> FEATURE:
<223> OTHER INFORMATION: linker L45

<400> SEQUENCE: 38
gctgaagctg cagccaaaga agctgcagcc aaagaggccg cagctaagga agccgcagca      60
aaagctgctg ctgaagctgc agccaaagaa gctgcagcca agaggccgc agctaaggaa      120 gccgcagcaa aagct                                                     135

<210> SEQ ID NO 39
<211> LENGTH: 180
<212> TYPE: DNA
<213> ORGANISM: artificial
<220> FEATURE:
<223> OTHER INFORMATION: linker L60

<400> SEQUENCE: 39
ggtggttctt cgggttcagg ctcgggctcc acaggtacat cgtcatcggg tacaggtact      60
tcagctggca acgggtac ctccgcatct acttccggtt caggctccgg aggcggcggc      120
ggctcgggtg gtggtggatc tgccggcgga accgcaaccg caggcgcttc ttctggttcc      180

<210> SEQ ID NO 40
<211> LENGTH: 402
<212> TYPE: DNA
<213> ORGANISM: artificial
<220> FEATURE:
<223> OTHER INFORMATION: linker L134

<400> SEQUENCE: 40
ggtggtggtg gttctggtgg tggtggttca ggcggcggcg gctcggcaga ggcatggtat      60
aatctcggga acgcatacta caaacagggc gattatcaga aggctatcga atactaccaa      120
aaagcactcg aactggaccc caataacgcg gaggcatggt acaatctcgg gaatgcgtac      180
tataagcagg gtgactacca aaaggccatt gaatactacc aaaaggcgct tgaactggac      240
ccgaacaacg ccgaggcctg gtataacctg gggaatgctt attacaagca ggggattat      300 caaaaggcaa tagaagacta ccagaaggcc ctcgaattgg accctaacaa tgtggtggt      360 ggttctggtg gtggtggttc aggcggcggc ggctcgggcg ga                       402

<210> SEQ ID NO 41
<211> LENGTH: 39
<212> TYPE: DNA
<213> ORGANISM: artificial
<220> FEATURE:
<223> OTHER INFORMATION: primer K842E sense

<400> SEQUENCE: 41
gtacataatc ctgtgtttga gccttttgaa aagccagtg                            39

<210> SEQ ID NO 42
<211> LENGTH: 39
<212> TYPE: DNA
<213> ORGANISM: artificial
<220> FEATURE:
<223> OTHER INFORMATION: primer K842E antisense

<400> SEQUENCE: 42
cactggcttt tcaaaaggct caaacacagg attatgtac                            39

<210> SEQ ID NO 43
```

```
<211> LENGTH: 36
<212> TYPE: DNA
<213> ORGANISM: artificial
<220> FEATURE:
<223> OTHER INFORMATION: primer Q807K sense

<400> SEQUENCE: 43
ccactccttc cctgaaacag ctgaatctgc aactcc                                36

<210> SEQ ID NO 44
<211> LENGTH: 36
<212> TYPE: DNA
<213> ORGANISM: artificial
<220> FEATURE:
<223> OTHER INFORMATION: primer Q807K antisense

<400> SEQUENCE: 44
ggagttgcag attcagctgt ttcagggaag gagtgg                                36

<210> SEQ ID NO 45
<211> LENGTH: 44
<212> TYPE: DNA
<213> ORGANISM: artificial
<220> FEATURE:
<223> OTHER INFORMATION: primer D864N sense

<400> SEQUENCE: 45
ctggaaatta agggaaataa tattgaccct gaagcagtta aagg                       44

<210> SEQ ID NO 46
<211> LENGTH: 44
<212> TYPE: DNA
<213> ORGANISM: artificial
<220> FEATURE:
<223> OTHER INFORMATION: primer D864N antisense

<400> SEQUENCE: 46
cctttaactg cttcagggtc aatattattt cccttaattt ccag                       44
```